(12) United States Patent
Johnson

(10) Patent No.: US 11,905,562 B2
(45) Date of Patent: *Feb. 20, 2024

(54) SEROTONIN TRANSPORTER GENE AND TREATMENT OF OPIOID-RELATED DISORDERS

(71) Applicant: University of Virginia Patent Foundation, Charlottesville, VA (US)

(72) Inventor: Bankole A. Johnson, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/301,660

(22) Filed: Apr. 9, 2021

(65) Prior Publication Data

US 2021/0301346 A1 Sep. 30, 2021

Related U.S. Application Data

(60) Continuation of application No. 16/807,379, filed on Mar. 3, 2020, now Pat. No. 10,995,374, which is a continuation of application No. 16/276,479, filed on Feb. 14, 2019, now Pat. No. 10,619,209, which is a continuation of application No. 16/133,234, filed on Sep. 17, 2018, now Pat. No. 10,533,226, which is a continuation of application No. 15/783,676, filed on Oct. 13, 2017, now abandoned, which is a continuation of application No. 15/417,933, filed on Jan. 27, 2017, now abandoned, which is a continuation of application No. 15/243,682, filed on Aug. 22, 2016, now abandoned, which is a continuation of application No. 14/886,691, filed on Oct. 19, 2015, now abandoned, which is a continuation of application No. 14/189,746, filed on Feb. 25, 2014, now abandoned, which is a division of application No. 12/919,905, filed as application No. PCT/US2009/035420 on Feb. 27, 2009, now Pat. No. 8,697,361.

(60) Provisional application No. 61/146,440, filed on Jan. 22, 2009, provisional application No. 61/059,301, filed on Jun. 6, 2008, provisional application No. 61/032,263, filed on Feb. 28, 2008.

(51) Int. Cl.
| | |
|---|---|
| *C12Q 1/6883* | (2018.01) |
| *A61K 45/06* | (2006.01) |
| *G01N 33/68* | (2006.01) |
| *G01N 33/94* | (2006.01) |
| *A61K 31/4178* | (2006.01) |

(52) U.S. Cl.
CPC ........ *C12Q 1/6883* (2013.01); *A61K 31/4178* (2013.01); *A61K 45/06* (2013.01); *G01N 33/6872* (2013.01); *G01N 33/942* (2013.01); *C12Q 2600/106* (2013.01); *C12Q 2600/118* (2013.01); *C12Q 2600/156* (2013.01); *C12Q 2600/158* (2013.01); *G01N 2800/307* (2013.01); *G01N 2800/50* (2013.01)

(58) Field of Classification Search
None
See application file for complete search history.

(56) References Cited

U.S. PATENT DOCUMENTS

| | | |
|---|---|---|
| 5,550,021 A | 8/1996 | Blum et al. |
| 6,169,105 B1 | 1/2001 | Wong et al. |
| 6,323,236 B2 | 11/2001 | McElroy |
| 7,033,771 B2 | 4/2006 | Brooks |
| 8,697,361 B2 | 4/2014 | Johnson |
| 8,753,815 B2 | 6/2014 | Johnson |
| 9,539,242 B2 | 1/2017 | Johnson |
| 10,533,226 B2 | 1/2020 | Johnson |
| 10,603,307 B2 | 3/2020 | Johnson |
| 10,619,209 B2 | 4/2020 | Johnson |
| 10,995,374 B2 | 5/2021 | Johnson |
| 10,997,121 B1 | 5/2021 | Jones et al. |
| 11,116,753 B2 | 9/2021 | Johnson |
| 11,324,723 B2 | 5/2022 | Johnson |
| 11,351,154 B2 | 6/2022 | Johnson |

(Continued)

FOREIGN PATENT DOCUMENTS

| | | |
|---|---|---|
| AT | E608888 T1 | 4/2013 |
| AU | 2011274355 B1 | 2/2017 |

(Continued)

OTHER PUBLICATIONS

Liu (J Hum Genet 2005 Vol 50 pp. 62-68).*

(Continued)

*Primary Examiner* — Amanda Haney

(74) *Attorney, Agent, or Firm* — Schwegman Lundberg & Woessner, P.A.

(57) ABSTRACT

The gene responsible for encoding SERT has a functional polymorphism at the 5'-regulatory promoter region, which results in two forms, long (L) and short (S). The LL-genotype is hypothesized to play a key role in the early onset of alcohol use. The present invention discloses the differences in treatment and diagnosis based on the L or short genotypes as well as on a single nucleotide polymorphism of the SERT gene, the 3' UTR SNP rs1042173. The present invention demonstrates the efficacy of using the drug ondansetron and similar drugs for treatment based on variations in the polymorphisms of the SERT gene as well as methods for diagnosing susceptibility to abuse of alcohol and other addiction-related diseases and disorders.

19 Claims, 4 Drawing Sheets

Specification includes a Sequence Listing.

(56) References Cited

U.S. PATENT DOCUMENTS

| | | |
|---|---|---|
| 2001/0023254 A1 | 9/2001 | McElroy |
| 2002/0091320 A1 | 7/2002 | Crutchfield et al. |
| 2003/0100479 A1 | 5/2003 | Dow et al. |
| 2003/0114475 A1 | 6/2003 | Fox et al. |
| 2003/0153590 A1 | 8/2003 | Kurkela et al. |
| 2004/0167164 A1 | 8/2004 | Pozuelo |
| 2005/0089890 A1 | 4/2005 | Cubicciotti |
| 2005/0245461 A1 | 11/2005 | Ehrich et al. |
| 2006/0286594 A1 | 12/2006 | Mundo et al. |
| 2007/0072899 A1 | 3/2007 | Johnson et al. |
| 2007/0088100 A1 | 4/2007 | Ahmed et al. |
| 2007/0167423 A1 | 7/2007 | Bergauer et al. |
| 2007/0196841 A1 | 8/2007 | Ruano et al. |
| 2007/0275970 A1 | 11/2007 | Weber |
| 2007/0292880 A1 | 12/2007 | Philibert et al. |
| 2008/0004291 A1 | 1/2008 | Singh |
| 2008/0228824 A1 | 9/2008 | Kenedy et al. |
| 2009/0269773 A1 | 10/2009 | Fantl et al. |
| 2010/0041689 A1 | 2/2010 | Johnson et al. |
| 2010/0076006 A1 | 3/2010 | Johnson et al. |
| 2010/0093762 A1 | 4/2010 | Wu |
| 2011/0065628 A1 | 3/2011 | Johnson et al. |
| 2011/0112159 A1 | 5/2011 | Johnson |
| 2011/0264374 A1 | 10/2011 | Johnson et al. |
| 2012/0115149 A1 | 5/2012 | Johnson |
| 2012/0302592 A1 | 11/2012 | Johnson et al. |
| 2013/0012559 A1 | 1/2013 | Johnson |
| 2013/0096173 A1 | 4/2013 | Johnson et al. |
| 2014/0206734 A1 | 7/2014 | Johnson |
| 2014/0288139 A1 | 9/2014 | Johnson |
| 2016/0139161 A1 | 5/2016 | Johnson |
| 2016/0331728 A1 | 11/2016 | Johnson |
| 2016/0376658 A1 | 12/2016 | Johnson |
| 2017/0226585 A1 | 8/2017 | Johnson |
| 2017/0239222 A1 | 8/2017 | Johnson |
| 2018/0251840 A1 | 9/2018 | Johnson |
| 2018/0344701 A1 | 12/2018 | Johnson |
| 2019/0002984 A1 | 1/2019 | Johnson |
| 2019/0249255 A1 | 8/2019 | Johnson |
| 2020/0199679 A1 | 6/2020 | Johnson |
| 2020/0316028 A1 | 10/2020 | Johnson |
| 2021/0000797 A1 | 1/2021 | Johnson |
| 2021/0023058 A1 | 1/2021 | Johnson |
| 2023/0014787 A1 | 1/2023 | Johnson |
| 2023/0241032 A1 | 8/2023 | Johnson |
| 2023/0263776 A1 | 8/2023 | Johnson |

FOREIGN PATENT DOCUMENTS

| | | |
|---|---|---|
| CA | 219554 A | 6/1922 |
| CA | 2716498 C | 12/2020 |
| EA | 019200 B1 | 1/2014 |
| EA | 024450 B1 | 9/2016 |
| EA | 027743 B1 | 8/2017 |
| EP | 0945133 A1 | 9/1999 |
| EP | 1262196 A2 | 12/2002 |
| EP | 2801625 A1 | 11/2017 |
| HK | 1151091 B1 | 1/2012 |
| JP | 2010513569 A | 4/2010 |
| JP | 2010537990 A | 12/2010 |
| RU | 2075978 C1 | 3/1997 |
| UA | 116615 C2 | 4/2018 |
| WO | WO-0050639 A2 | 8/2000 |
| WO | WO-03097873 A2 | 11/2003 |
| WO | WO-03100091 A1 | 12/2003 |
| WO | WO-2007009691 A2 | 1/2007 |
| WO | WO-2007039123 A2 | 4/2007 |
| WO | WO-2007095580 A2 | 8/2007 |
| WO | WO-2008077092 A2 | 6/2008 |
| WO | WO-2008095086 A2 | 8/2008 |
| WO | WO-2008095086 A3 | 8/2008 |
| WO | WO-2009010837 A2 | 1/2009 |
| WO | WO-2009026381 A2 | 2/2009 |
| WO | WO-2009026381 A3 | 2/2009 |
| WO | WO-2009029308 A1 | 3/2009 |
| WO | WO-2009108837 A2 | 9/2009 |
| WO | WO-2009108837 A3 | 9/2009 |
| WO | WO-2010126603 A1 | 11/2010 |
| WO | WO-2012003462 A1 | 1/2012 |
| WO | WO-2012003462 A4 | 1/2012 |
| WO | WO-2013036721 A1 | 3/2013 |

OTHER PUBLICATIONS

Dahmen (Psuchiatric Genetics 2005 vol. 15 pp. 13-16).*

Herman (Alcohol and Alcoholism vol. 38 No. 5 pp. 446-449, 2003).*

"Israel Application Serial No. 278149, Office Action dated Jul. 28, 2022", w/ English translation, 7 pgs.

"U.S. Appl. No. 12/520,095, Advisory Action dated Mar. 7, 2012", 4 pgs.

"U.S. Appl. No. 12/520,095, Final Office Action dated Sep. 1, 2011", 25 pgs.

"U.S. Appl. No. 12/520,095, Non Final Office Action dated Feb. 18, 2011", 25 pgs.

"U.S. Appl. No. 12/520,095, Non Final Office Action dated Aug. 21, 2013", 23 pgs.

"U.S. Appl. No. 12/520,095, Preliminary Amendment filed Jun. 19, 2009", 11 pgs.

"U.S. Appl. No. 12/520,095, Response filed Jan. 17, 2012 to Final Office Action dated Sep. 1, 2011", 13 pgs.

"U.S. Appl. No. 12/520,095, Response filed Feb. 29, 2012 to Final Office dated Sep. 1, 2011", 13 pgs.

"U.S. Appl. No. 12/520,095, Response filed Jun. 20, 2011 to Non Final Office Action dated Feb. 18, 2011", 14 pgs.

"U.S. Appl. No. 12/520,095, Response filed Dec. 6, 2010 to Restriction Requirement dated Aug. 5, 2010", 14 pgs.

"U.S. Appl. No. 12/520,095, Restriction Requirement dated Aug. 5, 2010", 8 pgs.

"U.S. Appl. No. 12/525,320, Non Final Office Action dated Feb. 8, 2012", 25 pgs.

"U.S. Appl. No. 12/525,320, Preliminary Amendment filed Jul. 31, 2009", 9 pgs.

"U.S. Appl. No. 12/525,320, Response filed Jan. 17, 2012 to Restriction Requirement dated Nov. 17, 2011", 9 pgs.

"U.S. Appl. No. 12/525,320, Restriction Requirement dated Nov. 17, 2011", 10 pgs.

"U.S. Appl. No. 12/674,348, Final Office Action dated Sep. 10, 2012", 17 pgs.

"U.S. Appl. No. 12/674,348, Non Final Office Action dated Dec. 13, 2011", 16 pgs.

"U.S. Appl. No. 12/674,348, Preliminary Amendment filed Feb. 19, 2010", 3 pgs.

"U.S. Appl. No. 12/674,348, Response filed May 14, 2012 to Non Final Office Action dated Dec. 13, 2011", 13 pgs.

"U.S. Appl. No. 12/675,486, Non Final Office Action dated Apr. 23, 2013", 22 pgs.

"U.S. Appl. No. 12/675,486, Preliminary Amendment filed Feb. 26, 2010", 16 pgs.

"U.S. Appl. No. 12/675,486, Response filed Aug. 24, 2012 to Restriction Requirement dated May 7, 2012", 15 pgs.

"U.S. Appl. No. 12/675,486, Restriction Requirement dated May 7, 2012", 6 pgs.

"U.S. Appl. No. 12/919,905, Advisory Action dated Jul. 16, 2013", 3 pgs.

"U.S. Appl. No. 12/919,905, Examiner Interview Summary dated Jul. 15, 2013", 3 pgs.

"U.S. Appl. No. 12/919,905, Final Office Action dated May 10, 2013", 16 pgs.

"U.S. Appl. No. 12/919,905, Non Final Office Action dated Feb. 1, 2013", 16 pgs.

"U.S. Appl. No. 12/919,905, Notice of Allowance dated Nov. 20, 2013", 9 pgs.

"U.S. Appl. No. 12/919,905, Preliminary Amendment dated Aug. 27, 2010", 11 pgs.

"U.S. Appl. No. 12/919,905, PTO Response to 312 Communication dated Feb. 26, 2014", 2 pgs.

(56) References Cited

OTHER PUBLICATIONS

"U.S. Appl. No. 12/919,905, Response filed Jan. 11, 2013 to Restriction Requirement dated Dec. 12, 2012", 12 pgs.
"U.S. Appl. No. 12/919,905, Response filed May 1, 2013 to Non Final Office Action dated Feb. 1, 2013", 10 pgs.
"U.S. Appl. No. 12/919,905, Response filed Jul. 10, 2013 to Final Office Action dated May 10, 2013", 12 pgs.
"U.S. Appl. No. 12/919,905, Restriction Requirement dated Dec. 12, 2012", 9 pgs.
"U.S. Appl. No. 12/919,905, Supplemental Preliminary Amendment dated Jan. 11, 2011", 3 pgs.
"U.S. Appl. No. 12/919,905, Supplemental Preliminary Amendment dated Mar. 17, 2011", 3 pgs.
"U.S. Appl. No. 13/318,179, Non Final Office Action dated Apr. 29, 2013", 16 pgs.
"U.S. Appl. No. 13/318,179, Preliminary Amendment filed Oct. 31, 2011", 8 pgs.
"U.S. Appl. No. 13/318,179, Response filed Mar. 6, 2013 to Restriction Requirement dated Feb. 14, 2013", 7 pgs.
"U.S. Appl. No. 13/318,179, Restriction Requirement dated Feb. 14, 2013", 7 pgs.
"U.S. Appl. No. 13/318,179, Supplemental Preliminary Amendment filed Jan. 16, 2012", 4 pgs.
"U.S. Appl. No. 13/569,465, Preliminary Amendment filed Aug. 8, 2012", 9 pgs.
"U.S. Appl. No. 13/569,465, Restriction Requirement dated Dec. 21, 2012", 10 pgs.
"U.S. Appl. No. 13/589,603, Examiner Interview Summary dated Jul. 12, 2013", 3 pgs.
"U.S. Appl. No. 13/589,603, Final Office Action dated Oct. 18, 2013", 9 pgs.
"U.S. Appl. No. 13/589,603, Non Final Office Action dated Apr. 29, 2013", 15 pgs.
"U.S. Appl. No. 13/589,603, Notice of Allowance dated Jan. 27, 2014", 11 pgs.
"U.S. Appl. No. 13/589,603, Preliminary Amendment filed Aug. 20, 2012", 4 pgs.
"U.S. Appl. No. 13/589,603, Response filed Jan. 7, 2013 to Restriction Requirement dated Dec. 7, 2012", 11 pgs.
"U.S. Appl. No. 13/589,603, Response filed Jan. 7, 2014 to Final Office Action dated Oct. 18, 2013", 14 pgs.
"U.S. Appl. No. 13/589,603, Response filed Jul. 26, 2013 to Non Final Office Action dated Apr. 29, 2013", 12 pgs.
"U.S. Appl. No. 13/589,603, Restriction Requirement dated Dec. 7, 2012", 8 pgs.
"U.S. Appl. No. 13/606,271, Advisory Action dated Feb. 16, 2016", 5 pgs.
"U.S. Appl. No. 13/606,271, Advisory Action dated Mar. 1, 2016", 8 pgs.
"U.S. Appl. No. 13/606,271, Advisory Action dated Apr. 25, 2014", 10 pgs.
"U.S. Appl. No. 13/606,271, Advisory Action dated Jul. 10, 2014", 3 pgs.
"U.S. Appl. No. 13/606,271, Examiner Interview Summary dated Apr. 25, 2014", 2 pgs.
"U.S. Appl. No. 13/606,271, Final Office Action dated Oct. 13, 2015", 18 pgs.
"U.S. Appl. No. 13/606,271, Final Office Action dated Dec. 18, 2013", 54 pgs.
"U.S. Appl. No. 13/606,271, Non Final Office Action dated Mar. 6, 2015", 42 pgs.
"U.S. Appl. No. 13/606,271, Non Final Office Action dated Jun. 10, 2013", 48 pgs.
"U.S. Appl. No. 13/606,271, Pre Appeal Brief Request filed Jun. 18, 2014", 5 pgs.
"U.S. Appl. No. 13/606,271, Response filed Apr. 17, 2014 to Final Office Action dated Dec. 18, 2013", 18 pgs.
"U.S. Appl. No. 13/606,271, Response filed May 1, 2013 to Restriction Requirement dated Apr. 4, 2013", 11 pgs.
"U.S. Appl. No. 13/606,271, Response filed Aug. 18, 2014 to Advisory Action dated Jul. 10, 2014", 18 pgs.
"U.S. Appl. No. 13/606,271, Response filed Sep. 8, 2015 to Non Final Office Action dated Mar. 6, 2015", 10 pgs.
"U.S. Appl. No. 13/606,271, Response filed Nov. 11, 2013 to Non Final Office Action dated Jun. 10, 2013", 13 pgs.
"U.S. Appl. No. 13/606,271, Restriction Requirement dated Apr. 4, 2013", 8 pgs.
"U.S. Appl. No. 13/606,271, Supplemental Amendment filed Jun. 18, 2014", 4 pgs.
"U.S. Appl. No. 13/606,271, Response filed Feb. 16, 2016 to Final Office Action dated Oct. 13, 2015", 12 pgs.
"U.S. Appl. No. 14/064,615, Preliminary Amendment dated Oct. 29, 2013", 6 pgs.
"U.S. Appl. No. 14/189,746, Non Final Office Action dated Apr. 27, 2015", 20 pgs.
"U.S. Appl. No. 14/189,746, Preliminary Amendment filed Feb. 26, 2014", 9 pgs.
"U.S. Appl. No. 14/266,313, Non Final Office Action dated Mar. 10, 2016", 6 pgs.
"U.S. Appl. No. 14/266,313, Notice of Allowability dated Oct. 17, 2016", 5 pgs.
"U.S. Appl. No. 14/266,313, Notice of Allowance dated Aug. 30, 2016", 8 pgs.
"U.S. Appl. No. 14/266,313, Preliminary Amendment filed May 30, 2014", 5 pgs.
"U.S. Appl. No. 14/266,313, Response filed Aug. 10, 2016 to Non Final Office Action dated Mar. 10, 2016", 7 pgs.
"U.S. Appl. No. 14/886,691, Non Final Office Action dated Mar. 22, 2016", 21 pgs.
"U.S. Appl. No. 15/096,675, Non Final Office Action dated Jun. 22, 2017", 42 pgs.
"U.S. Appl. No. 15/096,675, Preliminary Amendment Filed Jul. 28, 2016", 5 pgs.
"U.S. Appl. No. 15/096,675, Response filed May 1, 2017 to Restriction Requirement dated Jan. 30, 2017", 6 pgs.
"U.S. Appl. No. 15/096,675, Restriction Requirement dated Jan. 30, 2017", 7 pgs.
"U.S. Appl. No. 15/243,682, Final Office Action dated Oct. 27, 2016", 21 pgs.
"U.S. Appl. No. 15/397,076, Final Office Action dated Jun. 24, 2019", 8 pgs.
"U.S. Appl. No. 15/397,076, Non Final Office Action dated Jan. 25, 2019", 12 pgs.
"U.S. Appl. No. 15/397,076, Notice of Allowance dated Nov. 6, 2019", 10 pgs.
"U.S. Appl. No. 15/397,076, Response filed Oct. 10, 2018 to Restriction Requirement dated Jun. 13, 2018", 8 pgs.
"U.S. Appl. No. 15/397,076, Response filed Oct. 24, 2019 to Final Office Action dated Jun. 24, 2019", 7 pgs.
"U.S. Appl. No. 15/397,076, Response filed May 21, 2019 to Non Final Office Action dated Jan. 25, 2019", 9 pgs.
"U.S. Appl. No. 15/397,076, Restriction Requirement dated Jun. 13, 2018", 8 pgs.
"U.S. Appl. No. 15/417,933, Final Office Action dated Jun. 16, 2017", 21 pgs.
"U.S. Appl. No. 15/417,933,, Examiner Interview Summary filed Oct. 13, 2017", 2 pgs.
"U.S. Appl. No. 15/783,676, Final Office Action dated Jun. 13, 2018", 20 pgs.
"U.S. Appl. No. 15/848,079, Final Office Action dated Apr. 20, 2020", 26 pgs.
"U.S. Appl. No. 15/848,079, Final Office Action dated Jul. 23, 2019", 27 pgs.
"U.S. Appl. No. 15/848,079, Non Final Office Action dated Feb. 19, 2019", 24 pgs.
"U.S. Appl. No. 15/848,079, Response Filed Nov. 25, 2019 to Final Office Action dated Jul. 23, 2019", 11 pgs.
"U.S. Appl. No. 15/848,079, Response filed Dec. 21, 2018 to Restriction Requirement dated Oct. 22, 2018", 7 pgs.
"U.S. Appl. No. 15/848,079, Response filed May 21, 2019 to Non Final Office Action dated Feb. 19, 2019", 10 pgs.

(56) References Cited

OTHER PUBLICATIONS

"U.S. Appl. No. 15/848,079, Restriction Requirement dated Oct. 22, 2018", 5 pgs.
"U.S. Appl. No. 16/133,234, Final Office Action dated Jun. 5, 2019", 11 pgs.
"U.S. Appl. No. 16/133,234, Non Final Office Action dated Nov. 23, 2018", 16 pgs.
"U.S. Appl. No. 16/133,234, Notice of Allowance dated Aug. 27, 2019", 9 pgs.
"U.S. Appl. No. 16/133,234, Preliminary Amendment filed Sep. 18, 2018", 9 pgs.
"U.S. Appl. No. 16/133,234, Response filed Feb. 14, 2019 to Non Final Office Action dated Nov. 23, 2018", 7 pgs.
"U.S. Appl. No. 16/133,234, Response filed Jul. 23, 2019 to Final Office Action dated Jun. 5, 2019", 5 pgs.
"U.S. Appl. No. 16/276,479, Final Office Action dated Oct. 31, 2019", 14 pgs.
"U.S. Appl. No. 16/276,479, Non Final Office Action dated Jun. 12, 2019", 14 pgs.
"U.S. Appl. No. 16/276,479, Notice of Allowance dated Nov. 22, 2019", 7 pgs.
"U.S. Appl. No. 16/276,479, Preliminary Amendment Filed Feb. 15, 2019", 9 pgs.
"U.S. Appl. No. 16/276,479, Response filed Oct. 14, 2019 to Non-Final Office Action dated Jun. 12, 2019", 7 pgs.
"U.S. Appl. No. 16/276,479, Response filed Nov. 12, 2019 to Final Office Action dated Oct. 31, 2019", 7 pgs.
"U.S. Appl. No. 16/784,051 Preliminary Amendment filed Feb. 10, 2020", 5 pgs.
"U.S. Appl. No. 16/807,379 Preliminary Amendment filed Mar. 5, 2020", 4 pgs.
"U.S. Appl. No. 16/807,379, Non Final Office Action dated Sep. 17, 2020", 14 pgs.
"U.S. Appl. No. 16/807,379, Notice of Allowance dated Jan. 1, 2021", 7 pgs.
"U.S. Appl. No. 16/807,379, Response filed Dec. 16, 2020 to Non Final Office Action dated Sep. 17, 2020", 9 pgs.
"U.S. Appl. No. 16/931,813, Non Final Office Action dated Apr. 19, 2021", 23 pgs.
"U.S. Appl. No. 16/931,813, Preliminary Amendment filed Sep. 29, 2020", 5 pgs.
"U.S. Appl. No. 16/931,813, Response filed Jan. 12, 2021 to Restriction Requirement dated Oct. 14, 2020", 7 pgs.
"U.S. Appl. No. 16/931,813, Restriction Requirement dated Oct. 14, 2020", 6 pgs.
"U.S. Appl. No. 17/061,749, Examiner Interview Summary dated May 7, 2021", 3 pgs.
"U.S. Appl. No. 17/061,749, Non Final Office Action dated Feb. 8, 2021", 10 pgs.
"U.S. Appl. No. 17/061,749, Notice of Allowance dated May 20, 2021", 7 pgs.
"U.S. Appl. No. 17/061,749, Response filed May 5, 2021 to Non Final Office Action dated Feb. 8, 2021", 7 pgs.
"U.S. Appl. No. 17/061,749, Response filed Dec. 30, 2020 to Restriction Requirement Received—Prioritized Examination dated Dec. 24, 2020", 6 pgs.
"U.S. Appl. No. 17/061,749, Restriction Requirement Received—Prioritized Examination dated Dec. 24, 2020", 5 pgs.
"U.S. Appl. No. 17/061,749, Supplemental Notice of Allowability dated Aug. 18, 2021", 2 pgs.
"Australian Application Serial No. 2007333656, Office Action dated Jun. 21, 2012", 4 pgs.
"Australian Application Serial No. 2007333656, Office Action dated Dec. 13, 2012", 4 pgs.
et al., "Australian Application Serial No. 2007333656, Response filed Oct. 25, 2012 to Office Action dated Jun. 21, 2012", 27 pgs.
"Australian Application Serial No. 2009219174, First Examiner Report dated Jan. 8, 2014", 3 pgs.
"Australian Application Serial No. 2009219174, Response filed Feb. 28, 2014 to Office Action dated Jan. 8, 2014", 41 pgs.
"Australian Application Serial No. 2011274355, First Examiner Report dated Nov. 6, 2015", 6 pgs.
"Australian Application Serial No. 2011274355, Response filed Jun. 1, 2016 to Office Action dated Nov. 6, 2015", 21 pgs.
"Australian Application Serial No. 2011274355, Response filed Oct. 7, 2016 to Subsequent Examiners Report dated Jun. 29, 2016", 13 pgs.
"Australian Application Serial No. 2011274355, Subsequent Examiners Report dated Jun. 29, 2016", 5 pgs.
"Brazilian Application Serial No. PI 0908425-8, Office Action dated Feb. 12, 2020", w/ English Translation, 7 pgs.
"Brazilian Application Serial No. PI 0908425-8, Response filed May 18, 2020 to Office Action dated Feb. 12, 2020", w/ English Claims, 191 pgs.
"Canadian Application Serial No. 2,673,481, Office Action dated Sep. 12, 2013", 5 pgs.
"Canadian Application Serial No. 2,716,498, Office Action dated Feb. 25, 2016", 4 pgs.
"Canadian Application Serial No. 2,716,498, Office Action dated Mar. 31, 2017", 3 pgs.
"Canadian Application Serial No. 2,716,498, Office Action dated May 7, 2019", 3 pgs.
"Canadian Application Serial No. 2,716,498, Office Action dated Dec. 31, 2014", 4 pgs.
"Canadian Application Serial No. 2,716,498, Response filed Jun. 30, 2015 to Office Action dated Dec. 31, 2014", 34 pgs.
"Canadian Application Serial No. 2,716,498, Response filed Sep. 3, 2016 to Office Action dated Feb. 25, 2016", (English Translation of Claims), 21 pgs.
"Canadian Application Serial No. 2,716,498, Response filed Oct. 2, 2017 to Office Action dated Mar. 31, 2017", 31 pgs.
"Canadian Application Serial No. 2,716,498, Response filed Nov. 7, 2019 to Office Action dated May 7, 2019", 22 pgs.
"Canadian Application Serial No. 2,848,211, Office Action dated Jan. 4, 2021", 6 pgs.
"Canadian Application Serial No. 2,848,211, Office Action dated Apr. 18, 2018", 5 pgs.
"Canadian Application Serial No. 2,848,211, Office Action dated Jun. 3, 2019", 4 pgs.
"Canadian Application Serial No. 2,848,211, Response filed May 3, 2021 to Office Action dated Jan. 4, 2021", 18 pgs.
"Canadian Application Serial No. 2,848,211, Response filed Oct. 18, 2018 to Office Action dated Apr. 18, 2018", 26 pgs.
"Canadian Application Serial No. 2,848,211, Response filed Dec. 3, 2019 to Office Action dated Jun. 3, 2019", 24 pgs.
"Chinese Application Serial No. 200780051498.2, Non Final Office Action dated Apr. 13, 2011", 14 pgs.
"Chinese Application Serial No. 200780051498.2, Office Action dated Jan. 6, 2012", 10 pgs.
"Chinese Application Serial No. 200780051498.2, Office Action dated Jul. 30, 2012", w/ English Translation, 7 pgs.
"Chinese Application Serial No. 200780051498.2, Office Action Response filed Oct. 28, 2011", 6 pgs.
"Chinese Application Serial No. 200780051498.2, Response filed May 18, 2012 to Office Action mailed Jan. 6, 2012", 5 pgs.
"Chinese Application Serial No. 200780051498.2, Response filed Oct. 10, 2012 to Office Action dated Jul. 30, 2012", With English Claims, 6 pgs.
"Chinese Application Serial No. 200980115220.6, Amendment filed Jul. 29, 2011", (w/ English Translation), 41 pgs.
"Chinese Application Serial No. 200980115220.6, Notice of Reexamination dated Sep. 14, 2016", (English Translation), 7 pgs.
"Chinese Application Serial No. 200980115220.6, Office Action dated Jan. 14, 2013", (w/ English Translation), 15 pgs.
"Chinese Application Serial No. 200980115220.6, Office Action dated Aug. 2, 2013", 6 pgs.
"Chinese Application Serial No. 200980115220.6, Office Action dated Aug. 5, 2014", (w/ English Translation), 20 pgs.
"Chinese Application Serial No. 200980115220.6, Office Action dated Dec. 3, 2014", w/ English Claims, 47 pgs.
"Chinese Application Serial No. 200980115220.6, Office Action dated Dec. 18, 2013", (w/ English Translation), 13 pgs.

(56) References Cited

OTHER PUBLICATIONS

"Chinese Application Serial No. 200980115220.6, Office Action dated Jun. 3, 2015", w/ English Translation, 9 pgs.
"Chinese Application Serial No. 200980115220.6, Response filed Apr. 30, 2014 to Office Action dated Dec. 18, 2013", (w/ English Translation of Amended Claims), 59 pgs.
"Chinese Application Serial No. 200980115220.6, Response filed May 29, 2013 to Office Action dated Jan. 14, 2013", (Amendments not filed), 3 pgs.
"Chinese Application Serial No. 200980115220.6, Response filed Oct. 17, 2013 to Office Action dated Oct. 7, 2013", (Amendments not filed), 30 pgs.
"Chinese Application Serial No. 200980115220.6, Response filed Oct. 20, 2014 to Office Action dated Aug. 5, 2014", (w/ English Translation of Amended Claims), 66 pgs.
"Chinese Application Serial No. 200980115220.6, Response filed Apr. 20, 2015 to Office Action dated Dec. 3, 2014", in English, 30 pgs.
"Costa Rican Application Serial No. 10938, Office Action dated Apr. 8, 2010", 6 pgs.
"Costa Rican Application Serial No. 10938, Response to Opposition filed May 12, 2010", 6 pgs.
"DbSNP-rs1176719", Reference SNP (rs) Report, [Online]. [Archived Feb. 27, 2019]. Retrieved from the Internet: <URL: https://www.ncbi.nlm.nih.gov/snp/rs1176719>, (Released Oct. 2, 2018), 10 pgs.
"DbSNP-rs1150226", Reference SNP (rs) Report, [Online]. [Accessed Feb. 7, 2019]. Retrieved from the Internet: <URL: https://www.ncbi.nlm.nih.gov/snp/rs1150226>, (Released Oct. 2, 2018), 7 pgs.
"Definition of Sequela", Merriam-Webster, [Online]. Retrieved from Internet: <URL: http://www.merriam-webster.com/dictionary/sequelae>, (Jan. 31, 2013), 2 pgs.
"Eurasian Application Serial No. 2010001389, Office Action dated Sep. 19, 2012", With English Translation, 2 pgs.
"Eurasian Application Serial No. 201001389, Response filed Feb. 12, 2013 to Office Action dated Sep. 19, 2012", 51 pgs.
"Eurasian Application Serial No. 201390017, Office Action dated Nov. 13, 2014", w/ English Translation, 3 pgs.
"Eurasian Application Serial No. 201390017, Response filed May 15, 2015 to Office Action dated Nov. 13, 2014", w/ English Claims, 24 pgs.
"Eurasian Application Serial No. 201490548, Notice of Allowance dated Jan. 19, 2017", w/English Claims, 8 pgs.
"Eurasian Application Serial No. 201490548, Office Action dated Mar. 10, 2016", W/ English Translation, 2 pgs.
"Eurasian Application Serial No. 201490548, Office Action dated May 15, 2014", w/ English Translation, 2 pgs.
"Eurasian Application Serial No. 201490548, Response filed Aug. 4, 2016 to Office Action dated Mar. 10, 2016", w/English Claims, 89 pgs.
"Eurasian Application Serial No. 201490548, Response filed Sep. 15, 2014 to Office Action dated May 15, 2014", not in English, 1 pg.
"European Application Serial No. 09714591.6, Response filed Sep. 21, 2012 to Office Action dated Jun. 28, 2012", 14 pgs.
"European Application Serial No. 07869501.2, Office Action Filed Mar. 24, 2011", 3 pgs.
"European Application Serial No. 07869501.2, Office Action dated May 31, 2010", 1 pg.
"European Application Serial No. 07869501.2, Response filed Mar. 15, 2011 to Noting of Loss of Rights mailed Jan. 18, 2011", 5 pgs.
"European Application Serial No. 07869501.2, Response filed Aug. 31, 2009 to Communication dated Aug. 11, 2009", 5 pgs.
"European Application Serial No. 07869501.2, Supplemental European Search Report dated Feb. 25, 2010", 15 pgs.
"European Application Serial No. 09714591.6, Office Action dated Oct. 5, 10", 2 pgs.
"European Application Serial No. 09714591.6, Office Action dated Jun. 28, 2012", 6 pgs.
"European Application Serial No. 09714591.6, Response filed Jan. 5, 2012 to Extended Search Report dated Aug. 25, 2011", 15 pgs.
"European Application Serial No. 09714591.6, Response filed Nov. 2, 2010 to Office Action dated Oct. 5, 2010", 8 pgs.
"European Application Serial No. 10717322.1, Office Action dated Aug. 29, 2012", 5 pgs.
"European Application Serial No. 11801503.1, Extended European Search Report dated Nov. 27, 2013", 11 pgs.
"European Application Serial No. 12170027.2, Extended European Search Report dated Jan. 14, 2013", 6 pgs.
"European Application Serial No. 12830779.0, Extended European Search Report dated May 6, 2015", 13 pgs.
"European Application Serial No. 12830779.0, Office Action dated Apr. 9, 2014", 3 pgs.
"European Application Serial No. 12830779.0, Response filed Sep. 25, 2014 to Office Action dated Apr. 9, 2014", 9 pgs.
"European Application Serial No. 14173142.2, Communication Pursuant to Article 94(3) EPC dated May 13, 2016", 3 pgs.
"European Application Serial No. 14173142.2, Communication pursuant to Rule 69 EPC dated Nov. 17, 2014", 4 pgs.
"European Application Serial No. 14173142.2, Extended European Search Report dated Oct. 10, 2014", 9 pgs.
"European Application Serial No. 14173142.2, Response filed May 11, 2015 to Communication pursuant to Rule 69 EPC dated Nov. 17, 2014", 10 pgs.
"European Application Serial No. 15197075.3, Extended European Search Report dated Aug. 12, 2016", 15 pgs.
"European Application Serial No. 09714591.6, Extended European Search Report dated Jul. 28, 2011", 10 pgs.
"Friday Abstracts ED—Sanacora Gerard; Duman Ronald S", Biological Psychiatry, Elsevier Science, New York vol. 65, No. 8, (Apr. 15, 2009), 82S-162S.
"Hypnotic cure for Drunkards in Clinic", New York Times, (Dec. 1908), 1 pg.
"Indian Application Serial No. 4727/DELNP/2009, Office Action dated Sep. 29, 2014", 2 pgs.
"Indian Application Serial No. 6807/DELNP/2010, First Examiner Report dated Dec. 22, 2016", 14 pgs.
"International Application Serial No. PCT.US2011/0223481, Written Opinion dated Jul. 27, 2011", 5 pgs.
"International Application Serial No. PCT/US07/88100, International Search Report dated May 16, 2008", 1 pg.
"International Application Serial No. PCT/US07/88100, Written Opinion dated May 16, 2008", 11 pgs.
"International Application Serial No. PCT/US08/52628, International Search Report dated Aug. 19, 2008", 3 pgs.
"International Application Serial No. PCT/US08/52628, Written Opinion dated Aug. 19, 2008", 5 pgs.
"International Application Serial No. PCT/US09/35420, International Search Report dated Oct. 5, 2009", 5 pgs.
"International Application Serial No. PCT/US09/35420, Written Opinion dated Oct. 5, 2009", 20 pgs.
"International Application Serial No. PCT/US2008/052628, International Preliminary Report on Patentability dated Aug. 4, 2009", 6 pgs.
"International Application Serial No. PCT/US2008/064232, International Search Report dated Aug. 15, 2008", 1 pg.
"International Application Serial No. PCT/US2008/064232, Written Opinion dated Aug. 15, 2008", 8 pgs.
"International Application Serial No. PCT/US2008/073738, International Preliminary Report on Patentability dated Feb. 24, 2010", 6 pgs.
"International Application Serial No. PCT/US2008/073738, Written Opinion dated Nov. 12, 2008", 5 pgs.
"International Application Serial No. PCT/US2009/035420, International Preliminary Report on Patentability dated Sep. 10, 2010", 21 pgs.
"International Application Serial No. PCT/US2010/001273, International Preliminary Report on Patentability dated Jan. 4, 2011", 16 pgs.
"International Application Serial No. PCT/US2010/001273, Search Report dated Aug. 24, 2010", 10 pgs.
"International Application Serial No. PCT/US2010/001273, Written Opinion dated Aug. 24, 2010", 13 pgs.

(56) References Cited

OTHER PUBLICATIONS

"International Application Serial No. PCT/US2011/023481, International Preliminary Report on Patentability dated Jul. 27, 2011", 10 pgs.
"International Application Serial No. PCT/US2011/023481, International Search Report dated Jul. 27, 2011", 3 pgs.
"International Application Serial No. PCT/US2011/042823, International Preliminary Report on Patentability dated Jan. 17, 2013", 7 pgs.
"International Application Serial No. PCT/US2011/042823, International Search Report dated Dec. 6, 2011", 4 pgs.
"International Application Serial No. PCT/US2011/042823, Written Opinion dated Dec. 6, 2011", 5 pgs.
"International Application Serial No. PCT/US2012/054090, International Preliminary Report on Patentability dated Mar. 20, 2014", 7 pgs.
"International Application Serial No. PCT/US2012/054090, International Search Report dated Feb. 5, 2013", 5 pgs.
"International Application Serial No. PCT/US2012/054090, Invitation to Pay Additional Fees mailed Nov. 15, 2012", 2 pgs.
"International Application Serial No. PCT/US2012/054090, Written Opinion dated Feb. 5, 2013", 5 pgs.
"Israel Application Serial No. 223996, Office Action dated May 4, 2017", English Translation, 3 pgs.
"Israel Application Serial No. 223996, Office Action dated Jun. 7, 2018", w/ English translation, 5 pgs.
"Israel Application Serial No. 223996, Response filed Oct. 2, 2017 to Office Action dated May 4, 2017", 5 pgs.
"Israel Application Serial No. 223996, Response filed 10-04-28 to Office Action dated Jun. 7, 2018", w/o Translation, 6 pgs.
"Israel Application Serial No. 262874, Office Action dated Mar. 14, 2019", w/ English translation, 9 pgs.
"Israel Application Serial No. 262874, Office Action dated Jun. 3, 2020", w/o English Translation, 3 pgs.
"Israel Application Serial No. 278149, Office Action dated Jun. 20, 2021", 8 pgs.
"Israeli Application Serial No. 207822, Non Final Office Action dated Aug. 25, 2011", 3 pgs.
"Israeli Application Serial No. 207822, Office Action dated Jan. 20, 2014", 1 pg.
"Israeli Application Serial No. 207822, Office Action dated Jul. 9, 2013", English Translation, 2 pgs.
"Israeli Application Serial No. 207822, Office Action dated Sep. 21, 2014", 2 pg.
"Israeli Application Serial No. 207822, Office Action dated Nov. 13, 2012", 2 pgs.
"Israeli Application Serial No. 207822, Response filed Mar. 19, 2015 to Office Action dated Sep. 21, 2014", 2 pgs.
"Israeli Application Serial No. 207822, Response filed Apr. 7, 2013 to Office Action dated Nov. 13, 2012", English Translation, 9 pgs.
"Israeli Application Serial No. 207822, Response filed Jun. 19, 2014 to Office Action dated Jan. 20, 2014", 9 pgs.
"Israeli Application Serial No. 207822, Response filed Oct. 29, 2013 to Office Action dated Jul. 9, 2013", English Translation, 5 pgs.
"Israeli Application Serial No. 223996, Notification Prior to Examination dated Dec. 15, 2014", w/ English Translation, 3 pgs.
"Israeli Application Serial No. 223996, Office Action dated Oct. 13, 2015", 3 pgs.
"Israeli Application Serial No. 223996, Response filed Apr. 13, 2016 to Office Action dated Oct. 13, 2015", 15 pgs.
"Israeli Application Serial No. 262874, Response filed Jul. 14, 2019 to Office Action dated Mar. 14, 2019", w/English Claims, 4 pgs.
"Japanese Application Serial No. 2009-543177, Amendment filed Dec. 1, 2011", 2 pgs.
"Japanese Application Serial No. 2009-543177, Office Action dated Dec. 10, 2012", 5 pgs.
"Japanese Application Serial No. 2010-522982, Amendment filed May 10, 2011", 8 pgs.
"Japanese Application Serial No. 2010-548893, Amendment filed Feb. 21, 2012", 61 pgs.
"Japanese Application Serial No. 2010-548893, Examiners Decision of Final Refusal dated Apr. 8, 2014", 3 pgs.
"Japanese Application Serial No. 2010-548893, Office Action dated Nov. 27, 2013", w/English Translation, 9 pgs.
"Japanese Application Serial No. 2010-548893, Response filed Feb. 21, 14 to Office Action dated Nov. 27, 2013", w/English Claims, 28 pgs.
"Korean Application Serial No. 10-2010-7021452, Office Action dated Feb. 22, 2016", 7 pgs.
"Korean Application Serial No. 10-2010-7021452, Response filed Apr. 22, 2016 to Office Action dated Feb. 22, 2016", w/English Claims, 18 pgs.
"Mexican Application Serial No. MX/a/2009/006672, Office Action dated Apr. 12, 2012", 3 pgs.
"Mexican Application Serial No. MX/a/2009/006672, Office Action dated Sep. 6, 2011", 2 pgs.
"Mexican Application Serial No. MX/a/2009/006672, Office Action dated Dec. 17, 2012", 3 pgs.
"Mexican Application Serial No. MX/a/2009/006672, Response filed Jan. 31, 2012 to Office Action dated Sep. 6, 2011", 3 pgs.
"Mexican Application Serial No. MX/a/2009/006672, Response filed Aug. 15, 2012 to Non Final Office Action dated Apr. 16, 2012", w/ English Claims, 4 pgs.
"Mexican Application Serial No. MX/a/2010/009509, Office Action dated Mar. 13, 2013", 3 pgs.
"Mexican Application Serial No. MX/a/2010/009509, Response filed May 17, 2013 to Office Action dated Mar. 13, 2013", 12 pgs.
"NCBI Reference Cluster Report 17614942", Retrieved Nov. 28, 2011, [Online]. Retrieved from the Internet: <URL: http://ncbi.nlm.nih.gov>, (Aug. 2004), 2 pgs.
"NCBI Reference SNP Cluster Report 10160548", Retrieved Nov. 28, 2011, [Online]. Retrieved from the Internet: <URL: http://ncbi.nlm.nih.gov>, (Nov. 2003), 3 pgs.
"NCBI Reference SNP Cluster Report 1176746", Retrieved Nov. 28, 2011, [Online]. Retrieved from the Internet: <URL: http://www.ncbi.nlm.nih.gov>, (Oct. 2000), 3 pgs.
"NCBI Reference SNP Cluster Report 12270070", Retrieved Nov. 28, 2011, [Online]. Retrieved from the Internet: <URL: http://www.ncbi.nlm.nih.gov>, (Feb. 2004), 2 pgs.
"New Zealand Application Serial No. 588037, Office Action Response Filed May 28, 2012", 41 Pgs.
"New Zealand Application Serial No. 588037, Response filed Jul. 16, 2012 to Examiner Report dated Jun. 22, 2012", 40 pgs.
"New Zealand Application Serial No. 588037, Second Examination Report dated Jun. 22, 2012", 2 pgs.
"New Zealand Application Serial No. 605709, First Examiner Report dated Sep. 12, 2013", 2 pgs.
"New Zealand Application Serial No. 605709, Office Action dated Feb. 21, 2014", 1 pg.
"New Zealand Application Serial No. 605709, Response filed Feb. 18, 2014 to First Examiner Report dated Sep. 12, 2013", 158 pgs.
"New Zealand Application Serial No. 605709, Response filed Feb. 18, 2014 to Office Action", 158 pgs.
"New Zealand Application Serial No. 621352, First Examiner's Report dated Feb. 21, 2014", 2 pgs.
"New Zealand Application Serial No. 621352, Response filed Apr. 10, 2015 to First Examiner's Report dated Feb. 21, 2014", 155 pgs.
"New Zealand Application Serial No. 621356, First Examiner's Report dated Feb. 21, 2014", 2 pgs.
"New Zealand Application Serial No. 621356, Response filed Apr. 10, 2015 to First Examiner's Report dated Feb. 21, 2014", 157 pgs.
"New Zealand Application Serial No. 588037, First Examiner Report dated Mar. 21, 2011", 2 Pgs.
"Nicaragua Application Serial No. 2009-000124, Office Action dated Jun. 25, 2012", 5 pgs.
"SLC6A4 gene", Genetics Home Reference, [Online]. [Accessed Feb. 7, 2019]. Retrieved from the Internet: <URL: https://ghr.nlm.nih.gov/gene/SLC6A4>, (Feb. 5, 2019), 3 pgs.
"South African Application Serial No. 2010/06485, Amendment filed Nov. 10, 2013", 33 pgs.

(56) References Cited

OTHER PUBLICATIONS

"SS23605662", (for rsl 150226, NCBI, dbSNP), [Online]. Retrieved from the Internet: <URL: http://www.ncbi.nlm.nih.gov/projects/SNP/snp_ss.cgi?subsnp_id=23605662>, (2004), 2 pgs.
"Ukraine Application Serial No. A201300520, Office Action dated Jan. 3, 2017", 12 pgs.
"Ukraine Application Serial No. A201300520, Office Action dated Oct. 21, 2015", 14 pgs.
"Ukraine Application Serial No. A201300520, Response filed Jun. 15, 2016 to Office Action dated Oct. 22, 2015", w/English Claims, 9 pgs.
"Ukraine Application Serial No. A201300520, Response filed Sep. 5, 2017 to Office Action dated Jan. 3, 2017", W/English Claims, 9 pgs.
"Ukrainian Application Serial No. 201011545, Office Action dated May 30, 2013", English Translation, 7 pgs.
"Ukrainian Application Serial No. 201011545, Response filed Jul. 11, 2013 to Office Action dated May 30, 2013", w/English Claims, 35 pgs.
"Ukrainian Application Serial No. A201300520, Voluntary Amendment dated Jul. 17, 2014", w/ English Claims, 7 pgs.
Ait-Daoud, Nassima, et al., "Combining ondansetron and naltrexone reduces craving among biologically predisposed alcoholics: preliminary clinical evidence", Psychopharmacology, 154(1), (Feb. 2001), 23-27.
Anton, R. F., et al., "Structured Psychosocial Interventions Focused on Adherence Combined with Naltrexone Make Drinking Relapse Less Likely", Annals of Internal Medicine, 134(5), (2001), 388-389.
Balldin, J, et al., "A 6-Month Controlled Naltrexone Study: Combined Effect With Cognitive Behavioral Therapy in Outpatient Treatment of Alcohol Dependence", Alcoholism: Clinical and Experimental Research, vol. 27(7) Abstract only, (2003), 1142-1149.
Bankole, Johnson A, et al., "Determination of genotype combinations that can predict the outcome of the treatment of alcohol dependence using the 5-HT(3) antagonist ondansetron", The American Journal of Psychiatry, 170, (Sep. 1, 2013), 1020-1031.
Basu, A., et al., "Effect of Type 2 Diabetes on Meal Glucose Fluxes and Insulin Secretion", Diabetes, 53(suppl. 2), (2004), A579.
Benner, et al., "Evolution, language and analogy in functional genomics", Trends in Genetics, vol. 17, (2001), 414-418.
Bergman, R. N, et al., "Assessment of insulin sensitivity in vivo", Endocr Rev., 6(1), (Winter, 1985), 45-86.
Bergman, R. N, "The minimal model of glucose regulation: a biography", Adv Exp Med Biol., 537, (2003), 1-19.
Bergman, Richard, et al., "Minimal Model-Based Insulin Sensitivity Has Greater Heritability and a Different Genetic Basis Than Homeostasis Model Assessment or Fasting Insulin", Diabetes 52, (2003), 2168-2174.
Bergman, Richard, et al., "Quantitative estimation of insulin sensitivity", Am J Physiol., 236, (Jun. 1979), E667-E677.
Breda, E, et al., "Oral glucose tolerance test minimal model indexes of beta-cell function and insulin sensitivity", Diabetes 50, (2001), 150-158.
Castro, L. A, et al., "The pharmacologic treatment of the alcohol dependence", Rev Bras Psiquiatr., 26(Suppl 1), (May 2004), S43-6.
Caumo, Andrea, et al., "Insulin sensitivity from meal tolerance tests in normal subjects: A Minimal Model Index", Journal of Clinical Endocrinology & Metabolism 85, (2000), 4396-4402.
Chan, Eric, et al., "Integrating Transcriptomics and Proteomics", G&P magazine vol. 6 No. 3, (2006), 20-26.
Chen, G., et al., "Discordant Protein and mRNA Expression in Lung Adenocarcinomas", Molecular & Cellular Proteomics 1(4), (2002), 304-313.
Cheung, V. G., et al., "Natural variation in human gene expression assessed in lymphoblastoid cells", Nature Genetics, 33(3), (Mar. 2003), 422-425.
Chorbov, V. M, et al., "Relationship of 5-HTTLPR Genotypes and Depression Risk in the Presence of Trauma in a Female Twin Sample", American Journal of Medical Genetics, Part B: Neuropsychiatric Genetics, vol. 144B, (2007), 830-832.

Clausen, Jesper O, "Insulin Sensitivity Index, Acute Insulin Response, and Glucose Effectiveness in a Population-based Sample of 380 Young Healthy Caucasians", Journal of Clinical Investigation 98, (1996), 1195-1209.
Cobb, J P, et al., "Sepsis gene expression profiling: Murine splenic compared with hepatic responses determined by using complementary DNA microarrays", Crit Care Med, 30(12), (2002), 2711-2721.
Corley, R P, et al., "Association of candidate genes with antisocial drug dependence in adolescents", Drug and Alcohol Dependence, Elsevier Scientific Publisher vol. 96, No. 1-2, (Jul. 1, 2008), 90-98.
Corrao, et al., "A meta-analysis of alcohol consumption and the risk of 15 diseases", Preventive Medicine, vol. 38, (2004), 613-619.
Cortot, A., et al., "Gastric emptying and gastrointestinal absorption of alcohol ingested with a meal", Dig Dis Sci., 31(4), (Apr. 1986), 343-8.
Dahmen, Norbert, et al., "Tyrosine hydroxylase Val-81-Met polymorphism associated with early-onset alcoholism", Psychiatric Genetics, vol. 15, (2005), 13-16.
Dalla, Man C, et al., "Measurement of selective effect of insulin on glucose disposal from labeled glucose oral test minimal model", Am J Physiol Endocrinol Metab. 289(5), (2005), E909-14.
Dalla, Man C, et al., "Minimal Model Estimation of Glucose Absorption and Insulin Sensitivity from Oral Test: Validation with a Tracer Method", Am. J. Physiol. Endocrinol. Metab. 287, (2004), E637-E643.
Dalla Man, C., et al., "The oral glucose minimal model: estimation of insulin sensitivity from a meal test", IEEE Trans Biomed Eng., 49(5), (May 2002), 419-29.
Dawes, M, et al., "Drinking histories in alcohol-use-disordered youth: preliminary findings on relationships to platelet serotonin transporter expression with genotypes of the serotonin transporter", Journal of Studies on Alcohol and Drugs vol. 70, No. 6, (Nov. 2009), 899-907.
Dawes, M. A., et al., "A prospective, open-label trial of ondansetron in adolescents with alcohol dependence", Addictive Behaviors, 30, (2005), 1077-1085.
Defronzo, RA, "Glucose clamp technique: a method for quantifying insulin secretion and resistance", Am J Physiol. 237(3), (1979), E214-23.
Dick, D, et al., "Association analyses of the serotonin transporter gene with lifetime depression and alcohol dependence in the Collaborative Study on the Genetics of Alcoholism (COGA) sample", Psychiatric Genetics, vol. 17, No. 1, (Feb. 2007), 35-38.
Ducci, F, et al., "HTR3B is associated with alcoholism with antisocial behavior and alpha EEG power—an intermediate phenotype for alcoholism and co-morbid behaviors", Alcohol, Pergamon Press London GB, vol. 43, No. 1, (Feb. 1, 2009), 73-84.
Elahi, D, "In praise of the hyperglycemic clamp: A method for assessment of beta-cell sensitivity and insulin resistance", Diabetes Care 19, (1996), 278-286.
Enard, Wolfgang, et al., "Intra- and Interspecific Variation in Primate Gene Expression Patterns", Science, vol. 296, (2002), 340-343.
Enoch, et al., "Functional genetic variants that increase synaptic serotonin and 5-HT3 receptor sensitivity predict alcohol and drug dependence", Molecular Psychiatry, vol. 16, (Sep. 14, 2010), 1139-1146.
Enoch, et al., "Variation in genes encoding 5-HT3 receptors influences alcoholism vulnerability in diverse populations", Alcoholism: Clinical and Experimental Research, vol. 33, (Abstract Only), (2009), 295A.
Enoch, M. A, et al., "Genetics of Alcoholism Using Intermediate Phenotypes", Alcohol Clin Exp Res., 27(2), (Feb. 2003), 169-176.
Enoch, Mary-Anne, "Pharmacogenomics of Alcohol Response and Addiction", Am J Pharmacogenomics 2003; 3 (4): 217-232, (2003), 16 pgs.
Feinn, R, et al., "Meta-analysis of the association of a functional serotonin transporter promoter polymorphism with alcohol dependence", American Journal of Medical Genetics. Part B, Neuropsychiatric Genetics, vol. 133B, No. 1, (Feb. 5, 2005), 79-84.

(56) References Cited

OTHER PUBLICATIONS

Flier, Jeffrey S, "Chapter 140—Syndromes of Insulin Resistance", Principles and practice of endocrinology and metabolism, editor, Kenneth L. Becker; Published Philadelphia : J.B. Lippincott Co., (1995), 1249-1259.

Fraser, A G, et al., "Inter-individual and intra-individual variability of ethanol concentration-time profiles: comparison of ethanol ingestion before or after an evening meal", Br J Clin Pharmacol. 40(4), (1995), 387-392.

Grant, S A, et al., "Blood Alcohol Concentration and Psychomotor Effects", British Journal of Anesthesia, 85(3), (2000), 401-406.

Gu, Bo, et al., "Association between a polymorphism of the HTR3A gene and therapeutic response to risperidone treatment in drug-naive Chinese schizophrenia patients", Pharmacogenetics and Genomics, vol. 88(8), (2008), 721-727.

Hartman, B. J, "Hypnotherapeutic approaches to the treatment of alcoholism", J Natl Med Assoc., 68(2), (Mar. 1976), 101-3, 147.

Hegele, Robert A, "SNP Judgments and Freedom of Association", Arterioscler Thromb Vase Biology, vol. 22, (2002), 1058-1061.

Herman, Aryeh I, et al., "Serotonin Transporter Promoter Polymorphism and Differences in Alcohol Consumption Behavior in a College Student Population", Alcohol and Alcoholism, vol. 38, No. 5, (2003), 446-449.

Hirschhorn, J. N, et al., "A Comprehensive review of genetic association studies", Genetics in Medicine, 4 (2), (Mar. 2002), 45-61.

Hoshikawa, Y., et al., "Hypoxia induces different genes in the lungs of rats compared with mice", Physiol Genomics, 12(3), (2003), 209-219.

Ioannidis, John P.A, et al., "Replication validity of genetic association studies", Nature Genetics, vol. 29; 306-309, (Nov. 2001), 4 pgs.

Ji, Xiaofei, et al., "An Association between serotonin receptor 3B Gene (HTR3B) and Treatment-Resistant Schizophrenia (TRS) in a Japanese Population", Nagoya J Med Sci, vol. 70, (2008), 11-17.

Johnson, et al., "Oral Topiramate for Treatment of Alcohol Dependence: A Randomised Controlled Trial", The Lancet, vol. 361, (May 2003), 1677-1685.

Johnson, B A, et al., "Understanding and treating alcohol dependence", Alcohol Clin Exp Res., 30(3), (Mar. 2006), 567-84.

Johnson, B., "An Overview of the Development of Medications Including Novel Anticonvulsants for the Treatment of Alcohol Dependence", Expert Opinion, Pharmacother: 5(9), (2004), 1943-1955.

Johnson, B. A., et al., "Can serotonin transporter genotype predict serotonergic function, chronicity, and severity of drinking?", Progress in Neuro-Psychopharmacology & Biological Psychiatry, 32, (2008), 209-216.

Johnson, B. A, "Effects of GR 68755 on d-amphetamine-induced changes in mood, cognitive performance, appetite, food preference, and caloric and macronutrient intake in humans", Behav. Pharmacol., 7(3), (May 1996), 216-227.

Johnson, B. A, et al., "Pharmacogenetic approach at the serotonin transporter gene as a method of reducing the severity of alcohol drinking", Am J Psychiatry, 168(3), (Mar. 2011), 265-75.

Johnson, Bankole A, et al., "Age of onset as a discriminator between alcoholic subtypes in a treatment-seeking outpatient population", Am J Addict., 9(1), (Winter, 2000), 17-27.

Johnson, Bankole A., et al., "Combining Ondansetron and Naltrexone Effectively Treats Biologically Predisposed Alcoholics: From Hypotheses to Preliminary Clinical Evidence", Alcoholism: Clinical and Experimental Research, 24(5), (May 2000), 737-742.

Johnson, Bankole A, et al., "Determination of Genotype Combinations That Can Predict the Outcome of the Treatment of Alcohol Dependence using the 5-HT3 Antagonist Ondansetron", Am J Psychiatry, 170(9), (2013), 20 pgs.

Johnson, Bankole A, et al., "Development of novel pharmacotherapies for the treatment of alcohol dependence: focus on antiepileptics", Alcohol Clin Exp Res., 28(2), (Feb. 2004), 295-301.

Johnson, Bankole A, et al., "Improvement of physical health and quality of life of alcohol-dependent individuals with topiramate treatment: US multisite randomized controlled trial", Arch Intern Med., 168(11), (Jun. 9, 2008), 1188-99.

Johnson, Bankole A, et al., "Neuropharmacological treatments for alcoholism: scientific basis and clinical findings", Psychopharmacology (Berl), 149(4), (May 2000), 327-44.

Johnson, Bankole A., et al., "Ondansetron for Reduction of Drinking Among Biologically Predisposed Alcoholic Patients: A Randomized Controlled Trial", JAMA, vol. 284, No. 8, (Aug. 2000), 963-971.

Johnson, Bankole, "Progress in the Development of Topiramate for Treating Alcohol Dependence: From a Hypothesis to a Proof-of-Concept Study", Alcoholism: Clinical and Experimental Research vol. 28, Issue 8, (Aug. 2004), 1137-1144.

Johnson, Bankole A, "Serotonergic agents and alcoholism treatment: rebirth of the subtype concept—an hypothesis", Alcohol Clin Exp Res., 24(10), (Oct. 2000), 1597-601.

Johnson, Bankole A, et al., "Topiramate for Treating Alcohol Dependence: A Randomized Controlled Trial", JAMA, 298(14), (Oct. 10, 2007), 1641-51.

Kaysen, D., et al., "Domestic Violence and Alcohol Use: Trauma-related Symptoms and Motives for Drinking", Addict Behav., vol. 32(6), (2007), 1272-1283.

Kenna, G, "A within-group design of nontreatment seeking 5-HT-TLPR genotyped alcohol-dependent subjects receiving ondansetron and sertraline", Alcoholism, Clinical and Experimental Research vol. 33, No. 2, (Feb. 2009), 315-323.

Kenna, G. A., et al., "Pharmacotherapy, pharmacogenomics, and the future of alcohol dependence treatment, part 1", Am. J. Health-Syst. Pharm., 61, (Nov. 1, 2004), 2272-2279.

Kenna, G. A., et al., "Pharmacotherapy, pharmacogenomics, and the future of alcohol dependence treatment, part 2", Am. J. Health-Syst. Pharm., 61, (Nov. 15, 2004), 2380-2390.

Kenna, George A., "Pharmacotherapy of Alcohol Dependence: Targeting a Complex Disorder", Drug Discovery Today: Therapeutic Strategies, vol. 2, No. 1, XP004991436., (2005), 71-78.

Kenna, George A, et al., "Pharmacotherapy of Dual Substance Abuse and Dependence", CNS drugs, 21(3), (2007), 213-237.

Kjems, L L, et al., "Quantification of beta-cell function during IVGTT in Type II and non-diabetic subjects: assessment of insulin secretion by mathematical methods", Diabetologia 44, (2001), 1339-1348.

Konishi, T., et al., "ADH1B1, ADH1C2, DRD2 (-141C Ins), and 5-HTTLPR are associated with alcoholism in Mexican American men living in Los Angeles", Alcohol Clin Exp Res., vol. 28(8), (2004), 1145-52.

Kranzler, H. R, et al., "Effects of Ondansetron in Early- Versus Late-onset Alcoholics: A Prospective, Open-Label Study", Alcoholism: Clinical and Experimental Research, 27(7), (Jul. 2003), 1150-1155.

Liang, De-Yong, et al., "5-Hydroxytryptamine Type 3 Receptor Modulates Opioidinduced Hyperalgesia and Tolerance in Mice", Anesthesiology; 114(5): 1180-1189. doi:10.1097/ALN.0b013e31820efb19., (May 2011), 21 pgs.

Liefmann, R, "Endocrine Imbalance in Rheumatoid Arthritis and Rheumatoid Spondylitis: Hyperglycemia Unresponsiveness, Insulin Resistance, Increased Gluconeogenesis and Mesenchymal Tissue Degeneration", Acta Medica Scandinavica, 136(3), (1950), 226-232.

Liu, Y., et al., "Association of habitual smoking and drinking with single nucleotide polymorphism (SNP) in 40 candidate genes: data from random population-based Japanese samples", J Hum Genet., 50(2), (2005), 62-68.

Lucentini, J., "Gene Association Studies Typically Wrong", The Scientist, vol. 18 No. 24, (Dec. 20, 2004), 20 pgs.

Mahesh, et al., "Antidepressant-like activity of (4-phenylpiperazin-1-yl) (quinoxalin-2-yl) methanone (4a), a novel 5-HT3 receptor antagonist: An investigation in behavior-based rodent models of depression", Indian Journal Pharmacology, vol. 44, (2012), 560.

Mannelli, P, et al., "Polymorphism in the serotonin transporter gene and response to treatment in African American cocaine and alcohol-abusing individuals", Addict Biol., 10(3), (Sep. 2005), 261-268.

(56) References Cited

OTHER PUBLICATIONS

Mannelli, P., et al., "Polymorphism in the serotonin transporter gene and moderators of prolactin response to meta-chlorophenylpiperazine in African-American cocaine abusers and controls", Psychiatry Research, 144, (2006), 99-108.
Martin, J., et al., "Mapping regulatory variant for the serotonin transporter gene based on allelic expression imbalance", Molecular Psychiatry, vol. 12, (2007), 421-422.
Matsumoto, H., et al., "Pharmacokinetics of ethanol: a review of the methodology", Addiction Biology, 7(1), (2002), 5-14.
Moak, D. H, "Assessing the efficacy of medical treatments for alcohol use disorders", Expert Opin Pharmacother., 5(10), (Oct. 2004), 2075-89.
Moner, S. E., "Acupuncture and Addiction Treatment", Journal of Addictive Diseases, 15(3), (1996), 79-100.
Mumenthaler, M S, et al., "Ethanol pharmacokinetics in white women: nonlinear model fitting versus zero-order elimination analyses", Alcohol Clin Exp Res., 24(9), (Sep. 2000), 1353-62.
Ni, T C, et al., "Reassessment of glucose effectiveness and insulin sensitivity from minimal model analysis: a theoretical evaluation of the single-compartment glucose distribution assumption", Diabetes, 46(11), (1997), 1813-21.
Ni, Xingqun, et al., "Serotonin genes and gene-gene interactions in borderline personality disorder in a matched case-control study", Progress in Neuro-Psychopharmacology and Biological Psychiatry, vol. 33, (Nov. 12, 2009), 128-133.
Norberg, A, et al., "Role of variability in explaining ethanol pharmacokinetics: research and forensic applications", Clin. Pharmacokinet. 42(1), (2003), 1-31.
Norberg, A., et al., "Within- and between-subject variations in pharmacokinetic parameters of ethanol by analysis of breath, venous blood and urine", Br J Clin Pharmacol., 49(5), (2000), 399-408.
Oneta, C M, "First pass metabolism of ethanol is strikingly influenced by the speed of gastric emptying", Gut, 43(5), (1998), 612-619.
Pettinati, Helen, et al., "Recent advances in the treatment of alcoholism", Clinical Neuroscience Research, 5(2-4), (Nov. 2005), 151-159.
Philibert, "Transcriptional Profiling of Subjects From the Iowa Adoption Studies", Am J Med Genet Part B 144B, (Jul. 2007), 683-690.
Philibert, R A, et al., "The relationship of 5HTT (SLC6A4) methylation and genotype on mRNA expression and liability to major depression and alcohol dependence in subjects from the Iowa Adoption Studies", American Journal of Medical Genetics. Part B, Neuropsychiatric Genetics, vol. 147B, No. 5, (Jul. 5, 2008), 543-549.
Reaven, G M, "Pathophysiology of insulin resistance in human disease", Physiol Rev., 75(3), (1995), 473-86.
Reist, C., et al., "Serotonin Transporter Promoter Polymorphism Is Associated With Attenuated Prolactin Response to Fenfluramine", American Journal of Medicla Genetics (Neuropsychiatric Genetics), 105, (2001), 363-368.
Samochowiec, J., et al., "Family-based and case-control study of DRD2, DAT, 5HTT, COMT genes polymorphisms in alcohol dependence", Neurosci Lett., 410(1), (Dec. 13, 2006), 1-5.
Sander, Thomas, et al., "Serotonin Transporter Gene Variants in Alcohol-Dependent Subjects with Dissocial Disorder", Biol. Psychiatry, 43, (1998), 908-912.
Sellers, E. M, et al., "Clinical efficacy of the 5-HT3 antagonist ondansetron in alcohol abuse and dependence", Alcohol Clin Exp Res., 18(4), (Aug. 1994), 879-85.
Seneviratne, C, et al., "Characterization of a functional polymorphism in the 3' UTR of SLC6A4 and its association with drinking intensity", vol. 33, No. 2,, (Feb. 1, 2009), 332-339.
Seneviratne, C, et al., "Characterization of a functional polymorphism in the 3' UTR of SLC6A4 and its association with drinking intensity", Alcoholism, Clinical and Experimental Research, vol. 33, No. 2, (Feb. 2009), 332-339.

Silverstone, P H, et al., "Ondansetron, a 5-HT3 receptor antagonist, partially attenuates the effects of amphetamine: a pilot study in healthy volunteers", Int Clin Psychopharmacol. 7(1), (1992), 37-43.
Sookoian, S, et al., "Contribution of the functional 5-HTTLPR variant of the SLC6A4 gene to obesity risk in male adults", Obesity, vol. 16, No. 2, (Feb. 2008), 488-491.
Souza, et al., "Are serotonin 3A and 3B receptor genes associated with suicidal behavior in schizophrenia subjects?", Neuroscience Letters, vol. 489, (Dec. 22, 2010), 137-141.
Souza, RP, et al., "Influence of serotonin 3A and 3B receptor genes on clozapine treatment response in schizophrenia", Pharmacognetics and Genomics, vol. 20(4), (Apr. 2010), 274-276.
Steil, Garry M, et al., "Evaluation of insulin sensitivity and beta-cell function indexes obtained from minimal model analysis of a meal tolerance test", Diabetes, 53(5), (2004), 1201-7.
Stoltenberg, S. F., et al., "Serotonergic Agents and Alcoholism Treatment: A Simulation", Alcoholism: Clinical and Experimental Research, 27(12), (Dec. 2003), 1853-1859.
Swift, R., "Topiramate for the Treatment of Alcohol Dependence: Initiating Abstinence", The Lancet, vol. 361, (May 2003), 1666-1667.
Szilagyi, A., et al., "Combined effect of promoter polymorphisms in the dopamine D4 receptor and the serotonin transporter genes in heroin dependence", Neuropsychopharmacol Hung., 7(1), (2005), 28-33.
Toffolo, G, et al., "Beta-cell function during insulin-modified intravenous glucose tolerance test successfully assessed by the C-peptide minimal model", Metabolism, 48(9), (1999), 1162-1166.
Toffolo, G, et al., "Estimation of beta-cell sensitivity from intravenous glucose tolerance test C-peptide data. Knowledge of the kinetics avoids errors in modeling the secretion", Diabetes, 44(7), (1995), 845-854.
Toffolo, Gianna, et al., "Quantitative indexes of ß-cell function during graded up&down glucose infusion from C-peptide minimal models", Am J Physiol Endocrinol Metab., 280(1), (2001), E2-E10.
Umulis, D M, et al., "A physiologically based model for ethanol and acetaldehyde metabolism in human beings", Alcohol, 35(1), (2005), 3-12.
Walstab, Jutta, et al., "5-HT3 receptors: Role in disease and target of drugs", Pharmacology & Therapeutics 128 (2010) 146-169, (Jul. 16, 2010), 146-169.
Ward, R J, et al., "Women and alcohol susceptibility: could differences in alcohol metabolism predispose women to alcohol-related diseases?", Arch Womens Ment Health., 6(4), (2003), 231-8.
Welch, S, et al., "Minimal model analysis of intravenous glucose tolerance test-derived insulin sensitivity in diabetic subjects", J Clin Endocrinol Metab., 71(6), (1990), 1508-1518.
Whitehead, Douglas, et al., "Variation in tissue-specific gene expression among natural populations", Genome Biology vol. 6 Issue 2 Article R13, (2005), R13.1-R13.14.
Williams, S., "Medications for Treating Alcohol Dependence", American Family Physician, vol. 72, No. 9, (Nov. 2005), 1775-1780.
Willms, B, et al., "Gastric emptying, glucose responses, and insulin secretion after a liquid test meal: effects of exogenous glucagon-like peptide-1 (GLP-1)-(7-36) amide in type 2 (noninsulin-dependent) diabetic patients", J Clin Endocrinol Metab., 81(1), (1996), 327-32.
Wise, Roy A, et al., "A Psychomotor stimulant theory of addiction", Psychological Review 94, (1987), 469-492.
Wolff, Manfred E, "Burgers Medicinal Chemistry", 5th ed. Part 1. John Wiley & Sons, (1995), 975-977.
Xu, Li-Ping, "Analysis on the relationship between the polymorphism of serotonin transporter promoter gene and conduct disorder", (w/ English Abstract), Chinese Journal of Behavioral Medical Science, vol. 15, No. 7, (Jul. 2006), 588-590.
"U.S. Appl. No. 16/931,813, Response filed Oct. 19, 2021 to Non Final Office Action dated Apr. 19, 2021", 7 pgs.
"U.S. Appl. No. 16/931,813, Examiner Interview Summary dated Nov. 5, 2021", 2 pgs.
"Israel Application Serial No. 278149, Response filed Nov. 21, 2021 to Office Action dated Jun. 20, 2021", w English Claims, 8 bgs.
"U.S. Appl. No. 16/784,051, Non Final Office Action dated Dec. 6, 2021", 6 pgs.

(56) References Cited

OTHER PUBLICATIONS

"U.S. Appl. No. 16/784,051, Response filed Dec. 14, 2021 to Non Final Office Action dated Dec. 6, 2021", 6 pgs.
"U.S. Appl. No. 16/784,051, Notice of Allowance dated Jan. 12, 2022", 5 pgs.
"Canadian Application Serial No. 2,848,211, Final Examiner's Report dated Dec. 17, 2021", 6 pgs.
"U.S. Appl. No. 16/931,813, Notice of Allowance dated Feb. 4, 2022", 8 pgs.
"Canadian Application Serial No. 2,848,211, Response Filed Apr. 14, 2022 to Final Examiner's Report dated Dec. 17, 2021", 7 pgs.
"Israeli Application Serial No. 278149, Response filed Nov. 20, 2022 to Office Action dated Jul. 28, 2022", w English claims, 8 pgs.
"Canadian Application Serial No. 2,848,211, Voluntary Amendment filed Dec. 13, 2022", 5 pgs.
"U.S. Appl. No. 18/188,755, Restriction Requirement dated Jul. 5, 2023", 5 pgs.
"U.S. Appl. No. 18/188,755, Response filed Sep. 5, 2023 to Restriction Requirement dated Jul. 5, 2023", 7 pgs.

\* cited by examiner

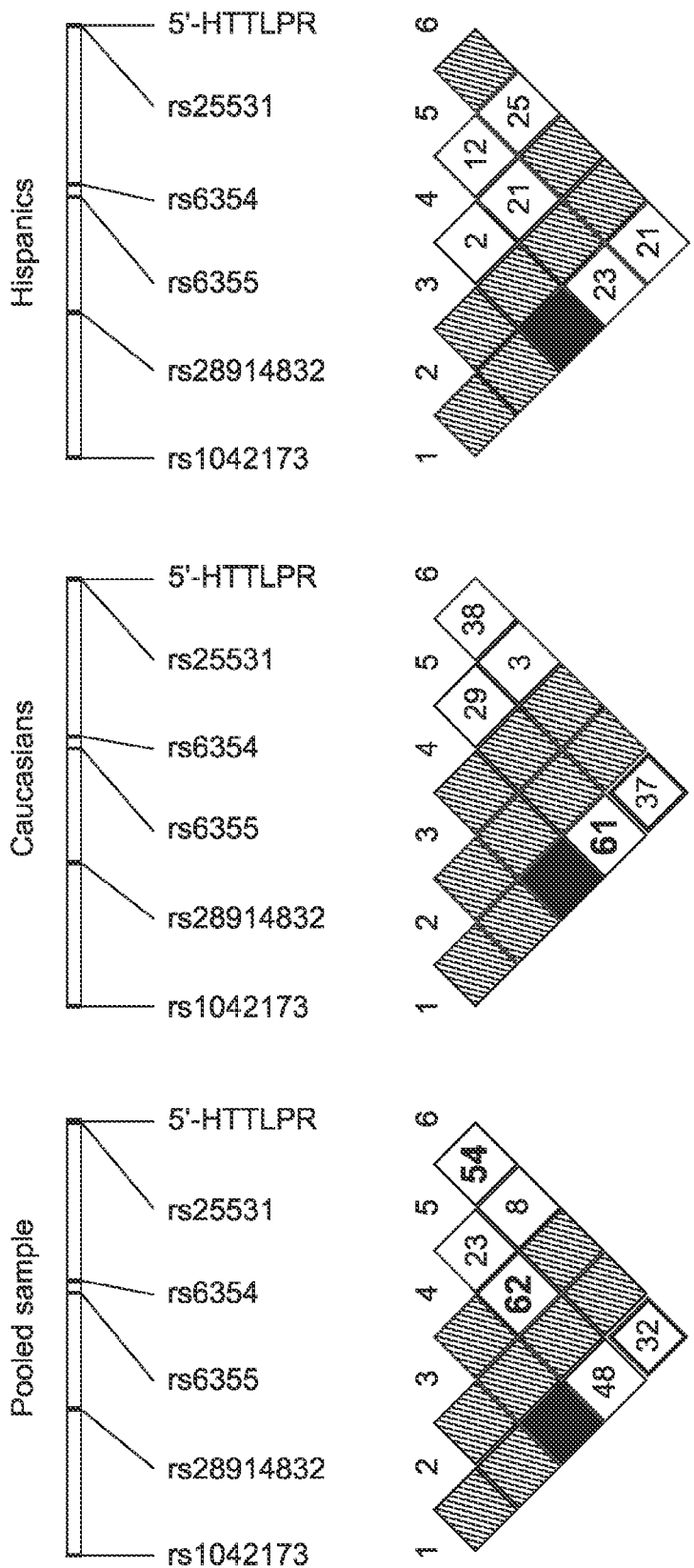
FIG. 1    Haploview-generated LD patterns

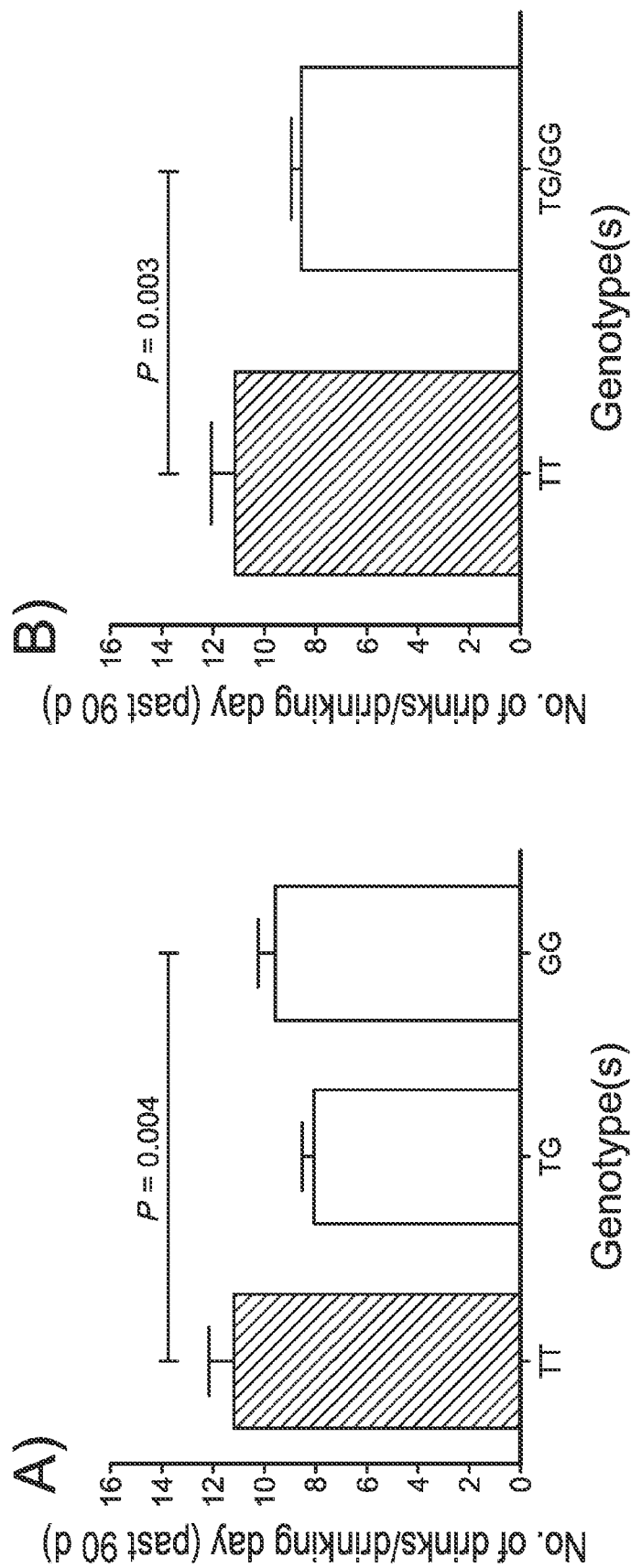
FIG. 2  Amounts of drinking in Caucasians

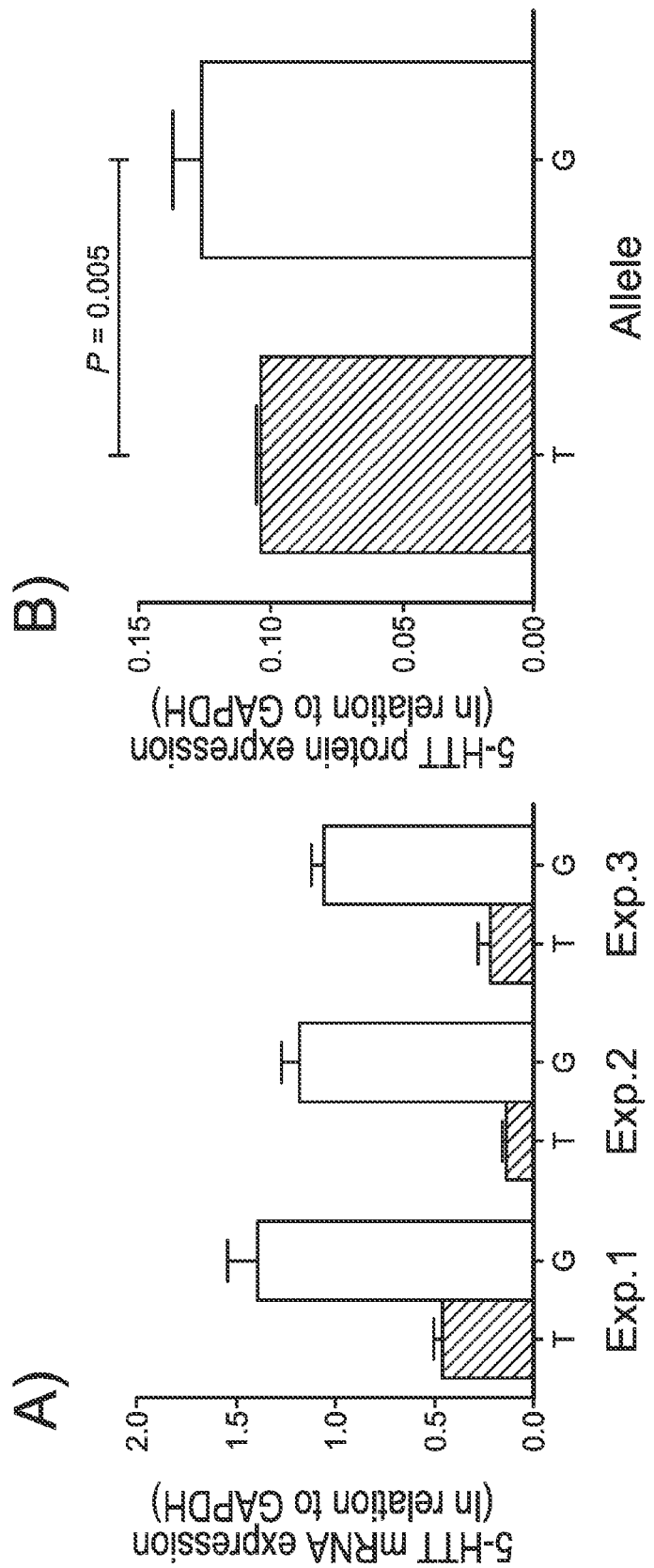
FIG. 3  5-HTT expression assays

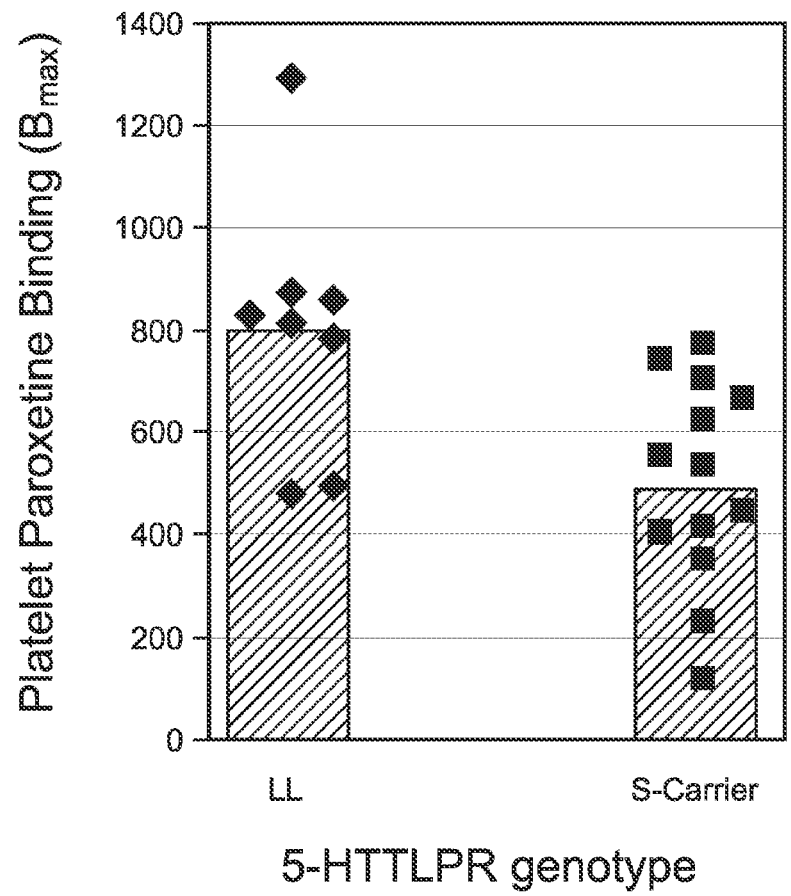
FIG. 4  Bmax vs. Genotype

SEROTONIN TRANSPORTER GENE AND TREATMENT OF OPIOID-RELATED DISORDERS

CROSS REFERENCE TO RELATED APPLICATIONS

This application is entitled to priority pursuant to 35 U.S.C. § 119(e) to U.S. provisional patent application nos. 61/032,263, filed on Feb. 28, 2008, 61/059,301, filed on Jun. 6, 2008, and 61/146,440, filed on Jan. 22, 2009. The entire disclosures of the afore-mentioned provisional patent applications are incorporated herein by reference.

STATEMENT REGARDING FEDERALLY SPONSORED RESEARCH OR DEVELOPMENT

This invention was made in part with United States Government support under Grant Nos. U10 AA011776-10, 1 N01 AA001016-000, 7 R01 AA010522-12, 5 R01 AA012964-06, 5 K23 AA000329-06, 3 R01 DA012844 and 5 R01 DA013783 awarded by the National Institutes of Health. The United States Government therefore has certain rights in the invention.

FIELD OF INVENTION

This invention relates generally to the field of diagnosing the susceptibility to addiction-related diseases and disorders and impulse control disorders, particularly alcohol-related diseases and disorders, as well as monitoring and treating the same.

BACKGROUND

Vulnerability to alcohol dependence is heritable, with a rate ranging from 0.52 to 0.64 (Kendler, 2001). Despite this high heritability rate, only one marker allele (alcohol-metabolizing aldehyde dehydrogenase genes) has been identified consistently to be associated with alcoholism (Kranzler et al, 2002). Of the various neurotransmitter systems through which alcohol mediates its effects, the serotonergic system has been shown to play an important role in alcohol preference and consumption (Johnson, 2004). Synaptic serotonergic neurotransmission is terminated when serotonin (5-HT) is transported back into pre-synaptic neurons by 5-HT transporters (5-HTTs) (Talvenheimo and Rudnick, 1980). Therefore, a major part of the functional capacity of the serotonergic system is regulated by the 5-HTT. Heavy episodic drinking is associated with numerous psychiatric and general medical conditions causing a major public health burden (Cargiulo, 2007). Several studies have reported a dose-response relationship between the extent of heavy drinking and the risk of alcohol related morbidity and mortality among heavy drinkers (Makela and Mustonen, 2007; Gastfriend et al., 2007). Consequently, reduction of heavy drinking is used as an indicator of treatment response in clinical trials aimed at treating alcohol dependence.

Of the various neurotransmitter systems through which alcohol mediates its effects, the serotonergic system has been shown to play an important role in alcohol preference and consumption (Johnson, 2004). Synaptic serotonergic neurotransmission is terminated when serotonin (5-HT) is transported back into pre-synaptic neurons by 5-HT transporters (5-HTTs) (Talvenheimo and Rudnick, 1980) and the degree of 5-HT reuptake depends on the density of 5-HTTs on presynaptic surface. The selective 5-HT reuptake inhibitors that act directly on 5-HTTs have been shown to reduce alcohol consumption in rats (Gill and Amit, 1989). However, in humans SSRIs have been effective at reducing heavy drinking only among some subtypes of alcoholics, more specifically in type A alcoholics but not in type B alcoholics (Dundon et al., 2004; Pettinati et al., 2000) who are considered to be more biologically predisposed to develop alcohol dependence. Therefore, it is reasonable to propose that allelic variations which alter expression levels of SLC6A4 gene can be expected to have an important effect on drinking intensity.

The human 5-HTT is encoded by a single gene (SLC6A4) mapped on chromosome 17q11.1-q12 (Ramamoorthy et al., 1993). The SLC6A4 gene spans ~35 kb and has 14 exons. The protein encoded by this gene, the 5-HTT, is a transmembrane protein containing 630 amino acids (Heils et al., 1996). The expression level of SLC6A4 is regulated by at least three mechanisms: transcription regulatory elements in the promoter (Ramamoorthy et al., 1993), differential splicing (Bradley and Blakely, 1997), and the use of different 3' polyadenylation sites (Battersby et al., 1999). Furthermore, several other polymorphisms that change amino acid sequence (Thr4Ala, Gly56Ala, Glu215Lys, Lys605Asn and Pro612Ser) of 5-HTT have been shown to affect 5-HT uptake function in cell cultures (Prasad et al., 2003).

Although the long (L) and short (S) polymorphism at 5-HTT linked polymorphic region (5-HTTLPR) of SLC6A4 has been extensively studied in the literature, the results are inconclusive. For example, in a meta-analysis of 17 studies, Feinn et al. (2005) showed that S allele was significantly associated with alcohol dependence in subjects with co-occurring serotonergic abnormalities while several other studies reported an association of alcohol dependence with the L allele (Kweon et al., 2005, Hu et al., 2005). On the other hand, numerous studies including the report by our group reveal a differential association between chronic problem-drinking and the density and function of serotonin transporters in alcoholic subjects carrying L and S variants of SLC6A4 (Little et al., 1998, Javors et al., 2005, Johnson et al., 2008). Located in the gene's transcriptional control region, 5-HTTLPR contains 16 tandem repeats of a 20 to 23 bp (G+C)-rich sequence between bp −1376 and bp −1027. Two common forms of this transcriptional control region have been found: a long 528 bp allele (L) with 16 repeats and a short 484 bp allele (S) with a deletion of 44 bp extending from bp −1255 to bp −1212.

Serotonin (5-HT) function has been implicated in the regulation of mood, impulsivity, and alcohol use that includes variation in the age of onset of drinking and onset of alcohol use disorders. The 5-HT system, originating in the raphe nuclei and projecting to cortex, hippocampus, and subcortical brain regions, is thought to influence drinking behavior directly in alcohol-use-disordered individuals by modulating the reinforcing effects of alcohol and/or indirectly by processes regulating impulsivity and affect. Findings from animal studies have shown that pharmacological enhancement of 5-HT activity inhibits alcohol intake. Human studies have shown that low 5-HT turnover is associated with impulsivity], as well as alcohol-seeking behavior and alcoholism. Lower central 5-HT turnover (e.g., 5-hydroxy indole acetic acid in cerebrospinal fluid) has been reported in early-onset alcohol-dependent (EOA) adults compared to late-onset alcohol dependent adults (LOA) and the lowest central 5-HT turnover occurs in EOA adults when both parents have alcohol dependence. Together, these findings support the hypothesis that 5-HT availability and function regulate drinking-related behaviors and drinking history.

Scientific frustration has been promulgated by failures to demonstrate clinical efficacy for selective serotonin reuptake inhibitors (SSRIs) in treating alcoholism. Animal studios show consistently that SSRIs reduce alcohol consumption in various models and across species (for a review, see Johnson and Ait-Daoud 2000). SSRIs augment central serotonergic function and, by tonic inhibition, decrease mesocorticolimbic dopamine (DA) release. DA activation mediates alcohol's rewarding effects; hence, its diminution should be associated with decreased abuse liability. Moreover, in humans, there is solid evidence that individuals with the highest biological predisposition to alcoholism, typically by having an early disease onset, family history, or both, have reduced serotonergic function (Buydens-Branchey et al. 1989; Fils-Aime et al 1996; LeMarquand et al 1994a; LeMarquand et al 1994b; Swann et al 1999). It was, therefore, tempting to predict that alcoholics would benefit from SSRI treatment, and that those with an early onset and/or family history would benefit the most because the SSRI would presumably ameliorate the existing disequilibrium in serotonergic function.

Despite the encouraging results of earlier studies, more rigorous, well controlled, state-of-the-art trials have generally failed to find a therapeutic effect for SSRIs in treating alcoholism (Gorelick and Paredes 1992; Kranzler et al 1996).

In humans, functional control of the serotonergic system also seems to be regulated by genetic differences in SERT expression (Meltzer and Arora 1988). The SERT possesses the only known functional polymorphism regulating the serotonin system (Heils et al 1997; Heils et al 1996; Lesch et al 1997). Basically, the polymorphism of the SERT 5' regulatory promoter region (5'-HTTLPR) on chromosome 17p12 consists of two types (Heils et al 1997; Heils et al 1996; Lesch et al 1997). The long (LL) variant, compared with the short (SS) or heterozygous (SL) form, is associated with three times greater 5-HT uptake from platelets (Greenberg et al 1999) and in lymphoblasts (Lesch et al 1996). Hence, individuals with the LL variant of 5'-HTTLPR can be expected to have increased SERT number and function and reduced levels of intrasynaptic 5-HT.

Recent scientific evidence would support the hypothesis of LL variant of 5'-HTTLPR predominance among EOA (Ishiguro et al 1999; Schuckit et al 1999). Turker et al. (1998) suggested that high ethanol tolerance may be associated with the SS/SL form of 5'-HTTLPR, but their rather informal criteria and the use of controls from a blood bank with uncertain alcohol histories may make their conclusions difficult to substantiate. Furthermore, a study by Sander et al. (1998) did not find a significant relationship (p=0.09) between SS/SL genotype and alcoholics with dissocial personality disorder. Finally, there are conflicting data on the relationship between the SS/SL form of 5'-HTTLPR and alcoholism in general (Edenberg et al. 1998; Hammoumi et al. 1999; Jorm et al. 1998; Sander et al. 1997); however, these studies contain no subtyping information. Moreover, it is difficult to compare these epidemiologic genotyping studies because of differing diagnostic criteria between the studies and different population frequencies across ethnic groups for the allelic forms. Perhaps most importantly, none of these studies have taken into account that it may be the interaction between these subtypes and alcohol consumption which is critical. That is, even though these allelic forms of the SERT may not determine vulnerability to alcoholism per se, the interaction between the allelic forms and alcohol consumption may determine treatment response, particularly to a selective serotonergic agent.

Reduced 5-HT neurotransmission has been reported in those with an increased propensity for drinking and in alcoholics who exhibit antisocial behaviors (i.e., EOA) (LeMarquand et al 1994a; LeMarquand et al 1994b). These results are consistent with: 1) the demonstration of increased 5-HT uptake into presynaptic serotonergic neurons in the brain, in lymphocytes, and in platelets of alcoholics and their descendants (Boismare et al 1987; Ernouf et al 1993; Faraj et al 1997) and 2) SPECT studies in nonhuman primates that had undergone early environmental stress, showing that increased binding of serotonin transporters is associated with greater aggressiveness and reduced sensitivity to ethanol intoxication (Heinz et al 1998). It would, therefore, be tempting to speculate that this hypo-serotonergic state could render individuals more vulnerable to experimentation with alcohol early in life.

Although acute alcohol intake may initially produce some temporary relief by increasing brain 5-HT levels, the residual effect is to reduce serotonin function, thereby setting up a vicious cycle (for a review see LeMarquand et al. (LeMarquand et al 1994a; LeMarquand et al 1994b)). Chronic excessive drinking does not result in sustained increases in 5-HT neurotransmission (Branchey et al 1981; Ledig et al 1982; Pohorecky et al 1978). Reduced SERT density in the raphe nuclei is associated with an early alcoholism onset in violent offenders (Tiihonen et al 1997) and with the combination of having the LL variant of 5'-HTTLPR and chronic drinking in both postmortem brains (Little et al 1998) and living individuals (Heinz et al 2000). The study of Heinz and colleagues (Heinz et al 2000) showed that individuals with the LL form of 5'-HTTLPR are more vulnerable to chronic alcohol-induced reductions in SERT density, but their study requires validation in an adequately powered prospective study that contains an equal number of individuals with the LL and SS/SL variants of 5'-HTTLPR. This would enable confirmation of the differential phenotypic expression of these allelic forms. Although it may, at first, seem paradoxical (i.e., for those with the LL variant of 5'-HTTLPR to have both reduced SERT density and decreased serotonergic function), it is notable that the SERTs in the raphe are associated with the regulation of cell firing rates.

There is a long felt need in the art for compositions and methods useful for diagnosing, treating, and monitoring alcohol disorders and susceptibility to alcohol disorders. The present invention satisfies these needs.

SUMMARY OF THE INVENTION

The present invention discloses several methods and assays useful for determining whether a subject has a predisposition to developing an addictive disease or disorder, determining whether a subject will be responsive to particular treatments, and compositions and methods useful for treating a subject in need of treatment. For example, the present invention encompasses compositions and methods, and combinations thereof, useful for predicting subjects susceptible to increased intensity of drinking and useful for predicting useful treatments.

The present invention encompasses compositions and methods useful for treating subjects who abuse alcohol based on identification of genetic markers indicative of a subject being predisposed to severe drinking or being more susceptible to alcoholism and problem drinking. The assays center on the serotonin system, particularly the serotonin transporter gene SLC6A4, its expression, and various polymorphisms of that gene. In one aspect, the marker is based on measurement of nucleotide polymorphisms. In one aspect, the polymorphism is a single nucleotide polymorphism (SNP). The invention further provides for the use of combinations of assays to help further predict a predisposition to developing an addictive disease or disorder and to help predict treatments based on the results of the assays. In one aspect, at least one drug which regulates part of the serotonin system is administered to the subject. In another aspect, combination therapy can be used by administering additional drugs.

Subjects comprising the G allele of SNP polymorphism rs1042173 of the serotonin transporter gene SLC6A4 were found herein to be associated with significantly lower drinking intensity compared to subjects homozygous for the T allele. This was true for whites but not Hispanics. Additionally, the present application discloses that cells transfected with the G allele of SNP polymorphism rs1042173 of the serotonin transporter gene SLC6A4 had significantly higher levels of both the mRNA and the serotonin transporter protein compared with cells transfected with the T allele. Even among alcohol-dependent G allele carriers for rs1042173, there was less intensity of drinking of compared with alcohol-dependent subject who were homozygous for the T allele. The present application further discloses that alcohol-dependent subjects with the TT genotype respond better to ondansetron treatment than similar subjects with the TG/GG genotype. Therefore, the present invention provides compositions and methods useful for predicting a predisposition to an addictive disease or disorder and the severity of that disorder, as well a compositions and methods useful for predicting suitable treatments and treatment regimens for those subjects. The present invention provides that for those homozygous for T, treatment may be customized to increase expression of the SLC6A4 gene or its protein, or their levels or activity, and that treatments further include compositions and methods useful for decreasing serotonin levels or activity.

The present application discloses that youths with the LL genotype of the functional polymorphism for the 5'-regulatory promoter region of the SERT gene (5-HTTLPR) had higher levels of SERT, as measured by $^3$H-paroxetine binding and had a significantly earlier age of onset of drinking. The present invention therefore encompasses a method of predicting subjects with a predisposition to early onset of drinking as well as methods of treating these subjects, including treatments to reduce expression of SERT and it activity.

The present application further discloses that the "interaction" of treatment (with ondansetron) and genotype (LS vs. LS/SS) is highly significant and that there is a significant effect of age of onset of drinking. The application discloses a significantly higher paroxetine binding (density of SERT) in LL-genotype vs. S-carriers (SS or SL genotypes). The present further application discloses that the LL group had a significantly earlier age of onset of drinking and a longer duration of drinking. These promising data provide the first evidence that alcoholics with the LL genotype, compared with their LS/SS counterparts, experience significantly greater reduction in the severity of drinking following ondansetron treatment.

In one embodiment, the present invention provides for treating alcoholics, as well as subjects with other addictive diseases and disorders, with at least one drug. In one aspect, the subject has the genotype LL. In one aspect, the at least one drug is ondansetron. In one aspect, the treatment reduces DDD. The present invention further encompasses the use of multiple drugs and combinations of drugs for treating subjects described herein.

Furthermore, the present invention provides for the use of combinations of assays to better predict or diagnose a susceptibility to developing an addictive disease or disorder as well as methods of predicting a personalized treatment based on the use of one or more predictive assays. Based on the results of one or more of the assays in a subject, treatments can be designed specifically for that subject.

The present invention encompasses an approach that combines drugs for the treatment or prevention of addictive disorders such as alcohol dependence. Because the reinforcing effects of most abused drugs are also mediated by CMDA neurons, the present invention provides combination therapy with drugs such as topiramate, ondansetron, and naltrexone as efficacious treatments for addictive disorders including (but not limited to) alcohol, eating, cocaine, methamphetamine, marihuana, tobacco abuse and addiction, and other addictive behaviors, including, but not limited to, gambling and sex. Based on the unexpected discoveries described herein, one of ordinary skill in the art will now appreciate that the compounds of the invention useful for combination drug therapy can in some instances be used singly instead of as part of a combination. Additionally, based on the present application, one of ordinary skill in the art will also appreciate that the compounds of the invention useful for combination drug therapy can in some instances be used in any combination.

In one embodiment, the present invention provides compositions and methods for treating or preventing an alcohol-related disease or disorder comprising administering to a subject a therapeutically effective amount of at least two anti-alcohol agents or compounds, and optionally other therapeutic agents. Preferably, at least three anti-alcohol agents or compounds are used in the combination therapy. The present invention further encompasses the adjunctive use of psychosocial management techniques. In one aspect, the drug combination therapy is more effective alone than when combined with psychosocial management techniques. In another aspect, the drug combination therapy combined with psychosocial management techniques is more effective than drug combination therapy alone. In one aspect, the present invention provides methods for treating or preventing an alcohol-related disease or disorder in a subject comprising administering an effective amount of at least two compounds, or preferably at least three compounds, or analogs, homologs, derivatives, modifications, and pharmaceutically acceptable salts thereof, selected from the group consisting of serotonergic agents, serotonin antagonists, selective serotonin re-uptake inhibitors, serotonin receptor antagonists, opioid antagonists, dopaminergic agents, dopamine release inhibitors, dopamine antagonists, norepinephrine antagonists, GABA agonists, GABA inhibitors, GABA receptor antagonists, GABA channel antagonists, glutamate agonists, glutamate antagonists, glutamine agonists, glutamine antagonists, anti-convulsant agents, NMDA-blocking agents, calcium channel antagonists, carbonic anhydrase inhibitors, neurokinins, small molecules, peptides, vitamins, co-factors, anti-orexin agents, regulators of cannabinoid receptor-1, and Corticosteroid Releasing Factor antagonists. In one aspect, the neurokinin is NPY. The present invention further encompasses administering other small molecules and peptides.

In one embodiment, the alcohol-related disease or disorder being treated includes, but is not limited to, early-onset alcoholic, late-onset alcoholic, alcohol-induced psychotic disorder with delusions, alcohol abuse, excessive drinking, heavy drinking, problem drinking, alcohol intoxication, alcohol withdrawal, alcohol intoxication delirium, alcohol withdrawal delirium, alcohol-induced persisting dementia, alcohol-induced persisting amnestic disorder, alcohol dependence, alcohol-induced psychotic disorder with hallucinations, alcohol-induced mood disorder, alcohol-induced or associated bipolar disorder, alcohol-induced or associated posttraumatic stress disorder, alcohol-induced anxiety disorder, alcohol-induced sexual dysfunction, alcohol-induced sleep disorder, alcohol-induced or associated gambling disorder, alcohol-induced or associated sexual disorder, alcohol-related disorder not otherwise specified, alcohol intoxication, and alcohol withdrawal. In one aspect, the alcohol-related disease or disorder is early onset alcoholic. In another aspect, the alcohol-related disease or disorder is late onset alcoholic.

In one embodiment, the present invention provides compositions and methods for reducing the frequency of alcohol consumption compared with the frequency of alcohol consumption before the treatment. One of ordinary skill in the art will appreciate that the frequency can be compared with prior consumption by the subject or with consumption by a control subject not receiving the treatment. In one aspect, the type of alcohol consumption is heavy drinking. In another aspect, it is excessive drinking.

In one embodiment, the present invention provides compositions and methods for reducing the quantity of alcohol consumed in a subject compared with the amount of alcohol consumed before the treatment or compared with the alcohol consumption by a control subject not receiving the treatment.

One of ordinary skill in the art will appreciate that in some instances a subject being treated for and addictive disorder is not necessarily dependent. Such subjects include, for example, subjects who abuse alcohol, drink heavily, drink excessively, are problem drinkers, or are heavy drug users. The present invention provides compositions and methods for treating or preventing these behaviors in non-dependent subjects.

In one embodiment of the invention, the present invention provides compositions and methods for improving the physical or psychological sequelae associated with alcohol consumption compared with a control subject not receiving the treatment.

In one embodiment, the present invention provides compositions and methods for increasing the abstinence rate of a subject compared with a control subject not receiving the treatment.

In one embodiment, the present invention provides compositions and methods for reducing the average level of alcohol consumption in a subject compared with the level of alcohol consumption before the treatment or compared with the level of alcohol consumption by a control subject not receiving the treatment.

In one embodiment, the present invention provides compositions and methods for reducing alcohol consumption and for increasing abstinence compared with the alcohol consumption by the subject before treatment or with a control subject not receiving the treatment.

In one embodiment, the present invention provides compositions and methods for treating a subject with a predisposition to early-onset alcoholism.

In one embodiment, the present invention provides compositions and methods for treating a subject with a predisposition to late-onset alcoholism.

One of ordinary skill in the art will appreciate that there are multiple parameters or characteristics of alcohol consumption which may characterize a subject afflicted with an alcohol-related disease or disorder. It will also be appreciated that combination therapies may be effective in treating more than one parameter, and that there are multiple ways to analyze the effectiveness of treatment. The parameters analyzed when measuring alcohol consumption or frequency of alcohol consumption include, but are not limited to, heavy drinking days, number of heavy drinking days, average drinking days, number of drinks per day, days of abstinence, number of individuals not drinking heavily or abstinent over a given time period, and craving. Both subjective and objective measures can be used to analyze the effectiveness of treatment. For example, a subject can self-report according to guidelines and procedures established for such reporting. The procedures can be performed at various times before, during, and after treatment. Additionally, assays are available for measuring alcohol consumption. These assays include breath alcohol meter readings, measuring serum CDT and GGT levels, and measuring 5-HTOL urine levels.

The present invention further provides adjunctive therapies to be used in conjunction with the combination drug therapies. The present invention further provides adjunctive therapy or treatment wherein the subject is also submitted to a psychosocial management program. Psychosocial management programs are known in the art and include, but are not limited to, Brief Behavioral Compliance Enhancement Treatment, Cognitive Behavioral Coping Skills Therapy, Motivational Enhancement Therapy, Twelve-Step Facilitation Therapy (Alcoholics Anonymous), Combined Behavioral Intervention, Medical Management, psychoanalysis, psychodynamic treatment, and Biopsychosocial, Report, Empathy, Needs, Advice, Direct Advice and Assessment. The present invention further encompasses the use of additional adjunct therapies and treatment, including hypnosis and acupuncture.

The present invention further provides for advice to be provided to subjects in conjunction with drug combination therapy. Advice constitutes a set of instructions pertaining to the potential consequences of excessive drinking, a calendar or other method for monitoring drinking, and instructions or suggestions about how to reduce or stop drinking. Any of these strategies either alone or in any combination, and no matter how brief or lengthy, can constitute advice. The advice can be provided in a format such as written, electronic, or interpersonal. In one embodiment, the drug combination therapy is more effective at treatment or prevention than merely administering a placebo and providing advice, administering no drugs and providing advice, or not administering drugs or providing advice. In one aspect, the combination drug therapy is more effective at treatment or prevention than drug therapy used in combination with a psychosocial management program.

In one embodiment, at least one of the compounds being administered is administered at least once a day. In one aspect, it is administered at least twice a day. In another embodiment, it is administered at least once a week. In yet another embodiment, it is administered at least once a month.

In one embodiment, at least one of the compounds is a serotonin receptor antagonist. In one aspect, the serotonin receptor is the serotonin-3 receptor. In one aspect, the compound is ondanseton.

Various aspects and embodiments of the invention are described in further detail below.

BRIEF DESCRIPTION OF THE DRAWINGS

FIG. 1. Haploview generated LD plots for the five SNPs examined in this study and 5-HTTLPR alleles of SLC6A4 gene. The pooled sample consists of subjects of Caucasian and Hispanic origin. Number in each box represents D' values for each SNP pair.

FIG. 2. Amounts of drinking in 165 Caucasian male and female alcoholics. (A) Amounts of drinking as a function of TT, TG and GG genotypes of rs1042173 (N of subjects in each group is: 47 TT, 77 TG, and 41 GG). Mean drinks per drinking day (±SEM) for the TT, TG and GG subjects were 11.17±0.98 vs. 8.05 f 0.47 and 9.58±0.67, respectively (F=5.63; p=0.004). (B) Drinks per drinking day variance as a function of the TT and G carriers (N of subjects in each genotype is: 47 TT, 118 G carriers). Mean drinks per drinking day (t SEM) for the T homozygotes and G carriers were 11.17±0.98 vs. 8.58±0.39 respectively (t=2.97; p=0.003).

FIG. 3. (A) Serotonin transporter (5-HTT) mRNA expression levels in HeLa cell cultures quantified by quantitative real-time PCR assay. The data shown here are mean±SEM of four replicates for 5-HTT mRNA expressed by the T and G alleles in three separate experiments (Exp.) conducted on separate times. GAPDH=glyceraldehyde-3-phosphate dehydrogenase. (B) Average differences in optical densities of bands seen on immunoblots for serotonin transporter (5-HTT) protein expression in HeLa cell cultures for the T and G allele specific expression in three cell cultures (G: 1.23+0.07; T: 0.28+0.05; N=4).

FIG. 4 is a graphic representation of platelet paroxetine binding (Bmax) for LL and S-carrier genotypes (5-HTTLPR genotype). The ordinate indicates platelet binding (Bmax) and the abscissa indicates the genotype.

DETAILED DESCRIPTION

Abbreviations, Generic Names, and Acronyms

5-HT—serotonin
5-HT—a subtype of serotonin receptor, the serotonin-3 receptor
5-HTOL—5-hydroxytryptophol
5-HTT—serotonin transporter (also referred to as SERT, 5HTT, HTT, and OCD1)
5-HTITLIR—serotonin transporter-linked polymorphic region
ADE—alcohol deprivation effect
ADI—adolescence diagnostic interview
ASPD—antisocial personality disorder
AUD—alcohol use disorder
BBCET—Brief Behavioral Compliance Enhancement Treatment
BED—binge eating disorder
b.i.d.—twice a day
B.—maximum specific paroxetine binding density
BRENDA—Biopsychosocial, Report, Empathy, Needs, Direct advice, and Assessment
CBI—combined behavioral intervention
CBT—Cognitive Behavioral Coping Skills Therapy, also referred to as cognitive behavioral therapy
CDT—carbohydrate-deficient transferrin
ChIPS—children's interview for psychiatric syndrome
CMDA—cortico-mesolimbic dopamine
DA—dopamine
DDD—drinks/drinking day
DSM—Diagnostic and Statistical Manual of Mental Disorders
EOA—early-onset alcoholic(s)
G2651T—a site within a putative polyadenylation signal for a commonly used 3' polyadenylation site of the SLC6A4 gene; also has reference identification number rs1042173 at the GenBank website of the National Center for Biotechnology Information
GABA—γ-amino-butyric acid (also referred to as γ-amino butyric acid and γ-aminobutyric acid)
GGT—γ-glutamyl transferase
ICD—impulse control disorder
IP—intraperitoneal
$K_d$—affinity constant
$K_m$—equilibrium constant
L—long
LOA—late-onset alcoholic(s)
MET—Motivational Enhancement Therapy
miRNA—micro RNA
MM—Medical Management
NAc—nucleus accumbens
Naltrexone—a p opioid receptor antagonist
ncRNA—non-coding RNA
NMDA—N-methyl-D-aspartate
NOS—not otherwise specified
Ondansetron (Zofran®)—a serotonin receptor antagonist
P—alcohol-preferring rats
S—short
SERT—serotonin transporter (also referred to as 5-HTT)
SLC6A4—human 5-HT transporter gene.
SNP—single nucleotide polymorphism
SSRI—selective serotonin re-uptake inhibitor
Topiramate (Topamax®)—an anticonvulsant
TSF—Twelve-Step Facilitation Therapy (e.g., Alcoholics Anonymous)
$V_{max}$—maximum serotonin uptake velocity
VTA—ventral tegmental area

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

"Addictive disorders" include, but are not limited to, eating disorders, obesity-related disorders, impulse control disorders, alcohol-related disorders, nicotine-related disorders, amphetamine-related disorders, methamphetamine-related disorders, cannabis-related disorders, cocaine-related disorders, gambling, sexual disorders, hallucinogen use disorders, inhalant-related disorders, benzodiazepine abuse or dependence related disorders, and opioid-related disorders.

One of ordinary skill in the art will appreciate that addictive disorders such as those related to alcohol or drugs, does mean that a subject is dependent unless specifically defined as such.

The term "additional therapeutically active compound", in the context of the present invention, refers to the use or administration of a compound for an additional therapeutic use other than just the particular disorder being treated. Such a compound, for example, could include one being used to treat an unrelated disease or disorder, or a disease or disorder which may not be responsive to the primary treatment for the addictive disease or disorder being treated. Disease and disorders being treated by the additional therapeutically active agent include, for example, hypertension and diabetes.

As used herein, the term "aerosol" refers to suspension in the air. In particular, aerosol refers to the particlization or atomization of a formulation of the invention and its suspension in the air.

As used herein, the term "affected cell" refers to a cell of a subject afflicted with a disease or disorder, which affected cell has an altered phenotype compared with a subject not afflicted with a disease, condition, or disorder.

Cells or tissue are "affected" by a disease or disorder if the cells or tissue have an altered phenotype relative to the same cells or tissue in a subject not afflicted with a disease, condition, or disorder.

As used herein, an "agonist" is a composition of matter that, when administered to a mammal such as a human, enhances or extends a biological activity of interest. Such effect may be direct or indirect.

The term "alcohol abuser", as used herein, refers to a subject who meets DSM IV criteria for alcohol abuse (i.e., "repeated use despite recurrent adverse consequences") but is not dependent on alcohol.

"Alcohol-related disorders" as used herein refers to diseases and disorder related to alcohol consumption and include, but are not limited to, alcohol-induced psychotic disorder, with delusions; alcohol abuse; excessive drinking; heavy drinking; problem drinking: alcohol intoxication: alcohol withdrawal; alcohol intoxication delirium; alcohol withdrawal delirium; alcohol-induced persisting dementia; alcohol-induced persisting amnestic disorder; alcohol dependence; alcohol-induced psychotic disorder, with hallucinations; alcohol-induced mood disorder; alcohol-induced or associated bipolar disorder; alcohol-induced or associated post traumatic stress disorder; alcohol-induced anxiety disorder; alcohol-induced sexual dysfunction: alcohol-induced sleep disorder; and alcohol-related disorder not otherwise specified (NOS).

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

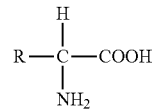

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
    Ala, Ser, Thr, Pro, Gly;
II. Polar, negatively charged residues and their amides:
    Asp, Asn, Glu, Gin;

III. Polar, positively charged residues:
  His, Arg, Lys;
IV. Large, aliphatic, nonpolar residues:
  Met Leu, Ile, Val, Cys
V. Large, aromatic residues:
  Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

An "antagonist" is a composition of matter that when administered to a mammal such as a human, inhibits or impedes a biological activity attributable to the level or presence of an endogenous compound in the mammal. Such effect may be direct or indirect.

As used herein, the term "anti-alcohol agent" refers to any active drug, formulation, or method that exhibits activity to treat or prevent one or more symptom(s) of alcohol addiction, alcohol abuse, alcohol intoxication, and/or alcohol withdrawal, including drugs, formulations and methods that significantly reduce, limit, or prevent alcohol consumption in mammalian subjects.

The term "appetite suppression", as used herein, is a reduction, a decrease or, in cases of excessive food consumption, an amelioration in appetite. This suppression reduces the desire or craving for food. Appetite suppression can result in weight loss or weight control as desired.

The term "average drinking," as used herein, refers to the mean number of drinks consumed during a one week period. The term "average drinking" is used interchangeably herein with the term "average level of drinking."

A "biomarker" is a specific biochemical in the body which has a particular molecular feature that makes it useful for measuring the progress of disease or the effects of treatment, or for measuring a process of interest.

A "compound," as used herein, refers to any type of substance or agent that is commonly considered a drug, or a candidate for use as a drug, as well as combinations and mixtures of the above.

A "control" subject is a subject having the same characteristics as a test subject, such as a similar type of dependence, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated.

As used herein, a "derivative" of a compound refers to a chemical compound that may be produced from another compound of similar structure in one or more steps, as in replacement of H by an alkyl, acyl, or amino group.

As used herein, the term "diagnosis" refers to detecting a risk or propensity to an addictive related disease disorder. In any method of diagnosis exist false positives and false negatives. Any one method of diagnosis does not provide 100% accuracy.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. However, the definitions of "disease" and "disorder" as described above are not meant to supersede the definitions or common usage related to specific addictive diseases or disorders.

A disease, condition, or disorder is "alleviated" if the severity of a symptom of the disease or disorder, the frequency with which such a symptom is experienced by a patient, or both, are reduced.

As used herein, an "effective amount" means an amount sufficient to produce a selected effect, such as alleviating symptoms of a disease or disorder. In the context of administering two or more compounds, the amount of each compound, when administered in combination with another compound(s), may be different from when that compound is administered alone. The term "more effective" means that the selected effect is alleviated to a greater extent by one treatment relative to the second treatment to which it is being compared.

The term "elixir," as used herein, refers in general to a clear, sweetened, alcohol-containing, usually hydroalcoholic liquid containing flavoring substances and sometimes active medicinal agents.

"Ethnic and Racial Categories" are defined herein according to NIH guidelines (1997 OMB Directive 15).

Ethnic Categories:

Hispanic or Latino: A person of Cuban, Mexican, Puerto Rican, South or Central American, or other Spanish culture or origin, regardless of race. The term "Spanish origin" can also be used in addition to "Hispanic or Latino."

Not Hispanic or Latino

Racial Categories:

American Indian or Alaska Native: A person having origins in any of the original peoples of North, Central, or South America, and who maintains tribal affiliations or community attachment.

Asian: A person having origins in any of the original peoples of the Far East. Southeast Asia, or the Indian subcontinent including, for example, Cambodia, China, India, Japan, Korea, Malaysia, Pakistan, the Philippine Islands, Thailand, and Vietnam. (Note: Individuals from the Philippine Islands have been recorded as Pacific Islanders in previous data collection strategies.)

Black or African American: A person having origins in any of the black racial groups of Africa. Terms such as "Haitian" or "Negro" can be used in addition to "Black or African American."

Native Hawaiian or Other Pacific Islander: A person having origins in any of the original peoples of Hawaii, Guam, Samoa, or other Pacific Islands.

White: A person having origins in any of the original peoples of Europe, the Middle East, or North Africa.

The term "excessive drinker," as used herein, refers to men who drink more than 21 alcohol units per week and women who consume more than 14 alcohol units per week. One standard drink is 0.5 oz of absolute alcohol, equivalent to 10 oz of beer, 4 oz of wine, or 1 oz of 100-proof liquor. These individuals are not dependent on alcohol but may or may not meet DSM IV criteria for alcohol abuse.

As used herein, a "functional" molecule is a molecule in a form in which it exhibits a property or activity by which it is characterized. A functional enzyme, for example, is one that exhibits the characteristic catalytic activity by which the enzyme is characterized.

The term "heavy drinker," as used herein, refers to men who drink more than 14 alcohol units per week and women who consume more than 7 alcohol units per week. One standard drink is 0.5 oz of absolute alcohol, equivalent to 10 oz of beer, 4 oz of wine, or 1 oz of 100-proof liquor. These individuals are not dependent on alcohol but may or may not meet DSM IV criteria for alcohol abuse.

The term "heavy drinking", as used with respect to the alcohol-dependent population of Example 1, refers to drinking at least 21 standard drinks/week for women and at least 30 drinks/week for men during the 90 days prior to enrollment in the study and is more fully described therein.

A "heavy drinking day," as used herein, refers to the consumption by a man or woman of more than about five or four standard drinks per drinking day, respectively.

The term "heavy drug use," as used herein, refers to the use of any drug of abuse, including, but not limited to, cocaine, methamphetamine, other stimulants, phencyclidine, other hallucinogens, marijuana, sedatives, tranquilizers, hypnotics, opiates at intervals or in quantities greater than the norm. The intervals of use include intervals such as at least once a month, at least once a week, and at least once a day. "Heavy drug use" is defined as testing "positive" for the use of that drug on at least 2 occasions in any given week with at least 2 days between testing occasions.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound or any agent to reduce or impede a described function, level, activity, synthesis, release, binding, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a subject. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

"Intensity of drinking" refers to the number of drinks, which can be equated with values such as drinks/day, drinks/drinking day, etc. Therefore, greater intensity of drinking means more drinks/day, or drinks/drinking day, etc.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

A "receptor" is a compound or molecule that specifically binds to a ligand.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self administration.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is also meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Obesity" is commonly referred to as a condition of increased body weight due to excessive fat. Drugs to treat obesity are generally divided into three groups: (1) those that decrease food intake, such as drugs that interfere with monoamine receptors, such as noradrenergic receptors, serotonin receptors, dopamine receptors, and histamine receptors; (2) those that increase metabolism: and (3) those that increase thermogenesis or decrease fat absorption by inhibiting pancreatic lipase (Bray, 2000, Nutrition, 16:953-960 and Leonhardt et al., 1999, Eur. J. Nutr., 38:1-13). Obesity has been defined in terms of body mass index (BMI). BMI is calculated as weight (kg)/[height (m)]$^2$, according to the guidelines of the U.S. Centers for Disease Control and Prevention (CDC), and the World Health Organization (WHO). Physical status: The use and interpretation of anthropometry. Geneva, Switzerland: World Health Organization 1995. WHO Technical Report Series), for adults over 20 years old, BMI falls into one of these categories: below 18.5 is considered underweight, 18.5-24.9 is considered normal, 25.0-29.9 is considered overweight, and 30.0 and above is considered obese.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A "recombinant polypeptide" is one which is produced upon expression of a recombinant polynucleotide.

A peptide encompasses a sequence of two or more amino acids wherein the amino acids are naturally occurring or synthetic (non-naturally occurring) amino acids. Peptide mimetics include peptides having one or more of the following modifications:
1. peptides wherein one or more of the peptidyl —C(O) NR— linkages (bonds) have been replaced by a non-peptidyl linkage such as a —CH2-carbamate linkage (—CH2OC(O)NR—), a phosphonate linkage, a —CH2-sulfonamide (—CH2-S(O)2NR—) linkage, a urea (—NHC(O)NH—) linkage, a —CH2-secondary amine linkage, or with an alkylated peptidyl linkage (—C(O)NR—) wherein R is C1-C4 alkyl;
2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;
3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl.

The term "per application" as used herein refers to administration of a drug or compound to a subject.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, and which is not deleterious to the subject to which the composition is to be administered.

A "predisposition" to an addictive disease or disorder refers to situations a subject has an increased chance of abusing a substance such as alcohol or a drug or becoming addicted to alcohol or a drug or other addictive diseases or disorders.

The term "prevent," as used herein, means to stop something from happening, or taking advance measures against something possible or probable from happening. In the context of medicine, "prevention" generally refers to action taken to decrease the chance of getting a disease or condition.

The term "problem drinker," as used herein, encompasses individuals who drink excessively and who report that their alcohol consumption is causing them problems. Such problems include, for example, driving while intoxicated, problems at work caused by excessive drinking, and relationship problems caused by excessive drinking by the subject.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl: aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl, or other acceptable groups linked to the terminal carboxyl group through an ester or ether bond.

The term "psychosocial management program," as used herein, relates to the use of various types of counseling and management techniques used to supplement the combination pharmacotherapy treatment of addictive and alcohol-related diseases and disorders.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Reduce"—see "inhibit".

The term "reduction in drinking", as used herein, refers to a decrease in drinking according to one or more of the measurements of drinking such as heavy drinking, number of drinks/day, number of drinks/drinking day, etc.

The term "regulate" refers to either stimulating or inhibiting a function or activity of interest.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest as interpreted in the context of the claim and the type of assay to be performed using that sample.

By "small interfering RNAs (siRNAs)" is meant, inter alia, an isolated dsRNA molecule comprising both a sense and an anti-sense strand. In one aspect, it is greater than 10 nucleotides in length. siRNA also refers to a single transcript that has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

By the term "specifically binds," as used herein, is meant a molecule which recognizes and binds a specific molecule, but does not substantially recognize or bind other molecules in a sample, or it means binding between two or more molecules as in part of a cellular regulatory process, where said molecules do not substantially recognize or bind other molecules in a sample.

The term "standard," as used herein, refers to something used for comparison. For example, it can be a known standard agent or compound which is administered or added and used for comparing results when adding a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

The term "one standard drink," as used herein, is 0.5 oz of absolute alcohol, equivalent to 10 oz of beer, 4 oz of wine, or 1 oz of 100-proof liquor.

A "subject" of diagnosis or treatment is a mammal, including a human.

The term "subject comprises a predisposition to the early onset of alcoholism," as used herein, refers to a subject who has, or is characterized by, a predisposition to the early onset of alcoholism.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" may include prophylaxis of the specific disease, disorder, or condition, or alleviation of the symptoms associated with a specific disease, disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from two to the specified number of carbon atoms and at least one triple bond. Examples of such groups include, but are not limited to, 1-propynyl, 2-propynyl, I-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" refers to from zero to four substituents, wherein the substituents are each independently selected. Each of the independently selected substituents may be the same or different than other substituents.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term ($C_5$-$C_8$ alkyl)aryl refers to any aryl group which is attached to the parent moiety via the alkyl group.

The term "heterocyclic group" refers to an optionally substituted mono- or bicyclic carbocyclic ring system containing from one to three heteroatoms wherein the heteroatoms are selected from the group consisting of oxygen, sulfur, and nitrogen. As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

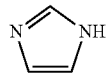

is understood to represent a mixture of the structures:

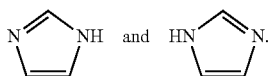

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

EMBODIMENTS

The number of serotonin transporter protein molecules in cells is affected by the amount of mature (secondary) scrotonin transporter mRNA molecules expressed in that cell. The expression levels of mRNA are controlled by the 5'-HTTLPR and 3'-UTR of the SLC6A4 gene via two different mechanisms. The 5'-HTTLPR region controls the transcription rate of SLC6A4 (Heils et al., (1996) J. Neurochem. 66:2621-2624), while rs1042173 SNP in the 3'-UTR of SLC6A4 affects mature mRNA levels via post-transcriptional mechanisms (Battersby et al., (1999), J. Neurochem. 72:1384-1388; Beaudoing et al., (2000), Genome Res 10:1001-1010; Chen et al., (2006), Nat. Genet. 38:1452-145).

The 5'-HTTLPR is found to harbor several binding sites for different transcription factor molecules necessary for the regulation of transcription initiation (Hu et al., (2005), Alcohol Clin. Exp. Res. 29:8-16). Therefore, the number of nascent (primary) mRNA copies transcribed by the SLC6A4 gene and the subsequent mature mRNA copies is affected by 5'-HTTLPR polymorphisms. The rs1042173 allelic differences are reported to be regulated by Micro RNA (miRNA) binding to at/near the rs1042173 site (for examples, miR-15a and miR-16 binding), degrading primary mRNA molecules and differential polyadenylation and resulting in altered mature mRNA levels. Therefore, the combined effects of 5'-HTTLPR and rs1042173 polymorphisms may modulate each other's individual effects on determining the overall availability of mature mRNA for translation into serotonin transporter protein molecules.

Without wishing to be bound by any particularly, it is hypothesized herein that, considering these factors, the combined genetic effect of 5'-HTTLPR and rs1042173 polymorphisms can result in differences in serotonergic function and regulation. Since alcohol consumption affects serotonergic function, this gene-gene interaction (5'-HTTLPR and rs1042173) may lead to a serotonergic dysregulation that either provokes, aggravates, or maintains further drinking behavior and alcoholism. These states of serotonergic dysregulation or alterations in function can be stabilized or ameliorated in excessive drinking or alcoholic populations by the compositions and methods of the present invention such as administration of serotonergic medications including the serotonin-3 (5-HT-3) antagonist, ondansetron.

In one embodiment, 5-HT-3 receptor antagonists (including ondansetron) can improve the drinking outcomes of those with certain polymorphisms of 5'-HTTLPR and/or rs1042173, either alone or combined. Because abused drugs are predicted to work through similar mechanisms, the present invention therefore encompasses the use of 5-HT3 antagonists (including ondansetron) to ameliorate or stabilize these serotonergic states and produce a therapeutic effect that improves clinical outcome for these disorders and diseases. The addictive diseases and disorders encompassed by the present compositions and methods include, but are not limited to, alcohol-related diseases and disorders, obesity-related diseases and disorders, eating disorders, impulse control disorders, nicotine-related disorders, amphetamine-related disorders, methamphetamine-related disorders, cannabis-related disorders, cocaine-related disorders, hallucinogen use disorders, inhalant-related disorders, benzodiazepine abuse or dependence related disorders, opioid-related disorders, gambling, and computer or electronic addictions.

Because the serotonin system has intimate connections and is modulated in the brain by other neurotransmitters, particularly dopamine, GABA, glutamate, opioids, and cannabinoid, the present invention encompasses the use of medications and drugs that affect the structure and function of these other neurotransmitters when combined with any serotonergic agent (including ondansetron). In one aspect, the combination is efficacious for individuals with polymorphisms at the 5'-HTTLPR and rs1042173 described herein or anywhere else in the serotonergic system. In another aspect, the present invention provides compositions, compounds and methods that are associated with these co-modulating neurotransmitters (i.e., dopamine, GABA, glutamate, opioids, and cannabinoid), including, but not limited to, topiramate, baclofen, gabapentin, naltrexone, nalmefene, and rimonabant—in combination with any serotonergic agent (including but not limited to ondansetron, selective serotonin re-uptake blockers, and other agonists or antagonists of other serotonin receptors or moieties) can produce a therapeutic effect to improve the clinical outcomes for individuals who use, abuse, misuse, or are dependent on alcohol. Because abused drugs are predicted to work through similar mechanisms, the present invention further provides combinations of these co-modulating drugs with any other serotonergic agent to be used to treat individuals with any substance use, abuse, misuse, dependence, or habit-forming behavior with polymorphisms at 5'-HTTLPR and rs1042173, or anywhere else in the serotonergic or co-modulating neurotransmitter systems (i.e., dopamine, GABA, glutamate, opioids, and cannabinoid), either alone or in combination.

The present invention encompasses compositions and methods for treatment or prevention where 5'-HTTLPR polymorphisms are associated with vulnerability or can sustain, provoke, or govern alcohol consumption. 5'-HTTLPR polymorphisms or related miRNA, mRNA, protein expression, levels, or states of function, or other biochemical products or chemical associations may themselves serve as a biomarker for alcohol consumption. Such a biomarker (i.e., blood test) can be used to provide a means or a test to determine whether, and how much, alcohol has been consumed by an individual. 5'-HTTLPR polymorphisms or related miRNA, mRNA, protein expression, levels, or states of function, or other biochemical products or chemical associations may themselves serve as a biomarker for alcohol use, misuse, or dependence. Such a biomarker (i.e., blood test) can be used to provide a means or a test to determine, evaluate, or support a diagnosis of alcohol use, misuse, or dependence.

The present invention encompasses compositions and methods for treatment or prevention where rs1042173 polymorphisms are associated with vulnerability or can sustain, provoke, or govern alcohol consumption. rs1042173 polymorphisms or related miRNA, mRNA, protein expression, levels, or states of function, or other biochemical products or chemical associations may themselves serve as a biomarker for alcohol consumption. Such a biomarker (i.e., blood test) can be used to provide a means or a test to determine whether, and how much, alcohol has been consumed by an individual. rs1042173 polymorphisms or related miRNA, mRNA, protein expression, levels, or states of function, or other biochemical products or chemical associations may themselves serve as a biomarker for alcohol use, misuse, or dependence. Such a biomarker (i.e., blood test) can be used to provide a means or a test to determine, evaluate, or support a diagnosis of alcohol use, misuse, or dependence.

The present invention encompasses compositions and methods for treatment or prevention where the combination of 5'-HTTLPR and rs1042173 polymorphisms is associated with vulnerability or can sustain, provoke, or govern alcohol consumption. The combination of 5'-HTTLPR and rs1042173 polyrmorphisms or related miRNA, mRNA, or protein expression, levels, or states of function, or other biochemical products or chemical associations, may itself serve as a biomarker for alcohol consumption. Such a biomarker can be used to provide a means or a test to determine whether, and how much, alcohol has been consumed by an individual. The combination of 5'-HTTLPR and rs1042173 polymorphisms or related miRNA, mRNA, or protein expression, levels, or states of function, or other biochemical products or chemical associations, may itself serve as a biomarker for alcohol use, abuse, or dependence. Such a biomarker can be used to determine, evaluate, or support a diagnosis of alcohol use, misuse, or dependence.

The present invention further provides for the use of any 5-HT-3 antagonist (including ondansetron) at any dose or dosage form to individuals with 5'-HTTLPR polymorphisms can ameliorate, improve, treat, or aid in recovery from alcohol use, abuse, or dependence, or substance use, abuse, or dependence.

The present invention encompasses providing any agent or drug that has an effect on the serotonin system, at any dose or dosage form, either directly or indirectly to individuals with 5'-HTTLPR polymorphisms can ameliorate, improve, treat, or aid in recovery from alcohol use, abuse, or dependence.

The present invention encompasses providing any 5-HT-3 antagonist (including ondansetron), at any dose or any dosage form, to individuals with rs1042173 polymorphisms can ameliorate, improve, treat or aid in recovery from alcohol use, abuse, or dependence, or substance use, abuse, or dependence.

The present invention encompasses providing any agent or drug that has an effect on the serotonin system, at any dose or dosage form, either directly or indirectly to individuals with rs1042173 polymorphisms can ameliorate, improve, treat, or aid in recovery from substance use, misuse, abuse, or dependence or any habit-forming behavior.

The present invention encompasses providing any 5-HT-3 antagonist (including ondansetron), at any dose or dosage form, to individuals with rs1042173 and 5'-HTTLPR polymorphisms combined can ameliorate, improve, treat, or aid in recovery from alcohol use, abuse, or dependence.

The present invention encompasses providing any agent or drug that has an effect on the serotonin system, at any dose or dosage form, either directly or indirectly to individuals with rs1042173 and 5'-HTTLPR polymorphisms can ameliorate, improve, treat, or aid in recovery from substance use, abuse, or dependence or habit-forming behavior.

The present invention encompasses providing any agent or drug or chemical entity that has an effect, at any dose or dosage form, either directly or indirectly to modulate, regulate, or alter the structural, functional, molecular, or biochemical effects of rs1042173 and 5'-HTTLPR polymorphisms, either alone or combined, can ameliorate, improve, treat, or aid in recovery from alcohol use, abuse, or dependence.

The present invention encompasses providing any agent or drug or chemical entity that has an effect, at any dose or dosage form, either directly or indirectly to modulate, regulate, or alter the structural, functional, molecular, or biochemical effects of rs1042173 and 5'-HTTLPR polymorphisms, either alone or combined, can ameliorate, improve, treat, or aid in recovery from substance use, abuse, or dependence or habit-forming behavior.

5'-HTTLPR and rs1042173 polymorphisms, either alone or in combination, or combined with any other polymorphisms within the serotonin system, or their related miRNA, mRNA, ncRNA, or protein expression, levels, or states of function or other biochemical products or chemical associations, may themselves serve as a biomarker for alcohol consumption. In one aspect, the use of 5'-H1-HTTLPR and rs1042173 as biomarkers can provide a means or a test to determine whether, and how much, alcohol has been consumed by an individual.

5'-HTTLPR and rs1042173 polymorphisms, either alone or in combination, or combined with any other polymorphisms within the serotonin system, or their related miRNA, mRNA, ncRNA, or protein expressions, levels, or states of function or other biochemical products or chemical associations, may themselves serve as a biomarker for alcohol use, misuse, or dependence. In one aspect, the use of 5'-HTTLPR and rs1042173 as biomarkers can provide a means or a test to determine, evaluate, or support a diagnosis of alcohol use, misuse, abuse, or dependence.

5'-HTTLPR and rs1042173 polymorphisms, either alone or in combination, or combined with any other polymorphisms within the serotonin system, or their related miRNA, mRNA, ncRNA, or protein expressions, levels, or states of function or other biochemical products or chemical associations, may themselves serve as a biomarker for substance use or a habit-forming behavior. In one aspect, the use of 5'-HTTLPR and rs1042173 as biomarkers can provide a means or a test to determine whether, and how much, substance has been consumed, or a habit-forming behavior has been performed, by an individual.

5'-HTTLPR and rs1042173 polymorphisms, either alone or in combination, or combined with any other polymorphisms within the serotonin system, or their related miRNA, mRNA, ncRNA, or protein expressions, levels, or states of function or other biochemical products or chemical associations, may themselves serve as a biomarker for substance use, abuse, misuse, dependence, or any habit-forming behavior. In one aspect, the use of 5'-HTTLPR and rs1042173 as biomarkers can provide a means or a test to determine whether, and how much, a substance has been consumed, or a habit-forming behavior has been performed, by an individual.

In one aspect, providing any agent or drug or chemical entity, at any dose or dosage form, either directly or indirectly to modulate, regulate, or alter the structural, functional, molecular, or biochemical effects of the serotonin system can be used to predict the response of a treatment effect toward any genetic polymorphism, either alone or combined, to ameliorate, improve, treat, or aid in recovery from alcohol use, abuse, or dependence, substance use, abuse, or dependence, or any habit-forming behavior.

In another aspect, providing any 5-HT-3 antagonist (including ondansetron), at any dose or dosage form, either directly or indirectly to modulate, regulate, or alter the structural, functional, molecular, or biochemical effects of any polymorphism, either alone or combined, within the serotonin system can ameliorate, improve, treat, or aid in recovery from alcohol use, abuse, or dependence or substance use, abuse, or dependence The present invention further encompasses a method whereby genetic screening is used to identify polymorphisms within the serotonin system or their related miRNA, mRNA, ncRNA, or protein expression, levels, or states of function, or other biochemical products or chemical associations, may serve as a biomarker for alcohol consumption. Such a biomarker (including a blood test) can be used to provide a means or a test to determine whether, and how much, alcohol has been consumed by an individual.

The present invention further encompasses a method whereby genetic screening is used to identify polymorphisms within the serotonin system or their related miRNA, mRNA, ncRNA, or protein expression, levels, or states of function, or other biochemical products or chemical associations, may serve as a biomarker to determine, evaluate, or support the diagnosis of alcohol use, misuse, abuse, or dependence.

The present invention further encompasses a method whereby genetic screening is used to identify polymorphisms within the serotonin system or their related miRNA, mRNA, ncRNA, or protein expression, levels, or states of function, or other biochemical products or chemical associations, may serve as a biomarker for the consumption of any substance, or any substance with abuse- or dependence-forming capability. Such a biomarker (including a blood test) can be used to provide a means or a test to determine whether, and how much of, any substance (including addictive substances) has been consumed, or a habit-forming behavior has been performed, by an individual.

The present invention further encompasses a method whereby genetic screening is used to identify polymorphisms within the serotonin system or their related miRNA, mRNA, ncRNA, or protein expression, levels, or states of function, or other biochemical products or chemical associations, may serve as a biomarker to determine, evaluate, or support the diagnosis of substance use, misuse, abuse, or dependence or any habit-forming behavior.

The present invention further encompasses a method whereby genetic screening is used to identify polymorphisms within the serotonin system or their related miRNA, mRNA, ncRNA, or protein expression, levels, or states of function, or other biochemical products or chemical associations, in order to identify individuals who use, abuse, misuse, or are dependent on alcohol or any other substance or habit-forming behavior, may be a basis for identifying treatment. Such a test (including a blood test) can be anticipated to determine individuals who will respond to any treatment (i.e., pharmacological, behavioral, genetic, biochemical, or any other combinations).

The present invention further encompasses a method whereby genetic screening is used to identify any polymorphisms within the serotonin system or their related miRNA, mRNA, ncRNA, or protein expressions, levels, or states of function, or other biochemical products or chemical associations, in order to identify individuals who use, abuse, misuse, or are dependent on any substance or have a habit-forming behavior, may be a basis for identifying adverse events or side effects or optimizing any treatment (i.e., pharmacological, behavioral, genetic, biochemical, or any other combinations) at any dose, dosage form, or treatment regimen. Such a test can be anticipated to determine individuals who will not respond to a treatment or individuals who will need additional measures to optimize the success of any treatment (i.e., pharmacological, behavioral, genetic, biochemical, or any other combinations).

The present invention further encompasses a method whereby genetic screening is used to identify any polymorphisms within the serotonin system or their related miRNA, mRNA, ncRNA, or protein expression, levels, or states of function, or other biochemical products or chemical associations, in order to identify individuals who use, abuse, misuse, or are dependent on alcohol or any other substance or have a habit-forming behavior (including but not limited to obesity, gambling, or computer or electronic addictions), may be a basis for identifying adverse events or side effects or optimizing treatment with any 5-HT-3 antagonist (including ondansetron) at any dose or dosage form. Such a test can be anticipated to determine individuals who will respond to treatment with any 5-HT-3 antagonist (including ondansetron).

The present invention further encompasses a method whereby genetic screening is used to identify 5'-HTTLPR and rs1042173 polymorphisms or their related miRNA, mRNA, or protein expressions, levels, or states of function, or other biochemical products or chemical associations, either alone or in any combination, in order to identify individuals who use, abuse, misuse, or are dependent on alcohol or any other substance or have a habit-forming behavior, may be a basis for identifying adverse events or side effects or optimizing treatment with any 5-HT-3 antagonist (including ondansetron) at any dose or dosage form. Such a test (including a blood test) can be anticipated to determine individuals who will not respond to treatment with a 5-HT-3 antagonist (including ondansetron) or individuals who will need additional measures to optimize the success of treatment with any 5-HT-3 antagonist (including ondansetron).

The present invention further encompasses a method whereby genetic screening is used to identify 5'-HTTLPR and rs1042173 polymorphisms or their related miRNA, mRNA, or protein expressions, levels, or states of function, or other biochemical products or chemical associations, either alone or in any combination, in order to identify individuals who use, abuse, misuse, or are dependent on alcohol or any other substance or have a habit-forming behavior (including but not limited to obesity, gambling, or computer or electronic addictions), may be a basis for identifying those who will respond to treatment with any 5-HT-3 antagonist (including ondansetron) at any dose or dosage form. Such a test (including a blood test) can be anticipated to determine individuals who will respond to treatment with a 5-HT-3 antagonist (including ondansetron). Such diseased individuals can be identified by means of the genetic screening and then provided with ondansetron.

The present invention further encompasses a method whereby genetic screening is used to identify 5'-HTTLPR and rs1042173 polymorphisms or their related miRNA, mRNA, or protein expressions, levels, or states of function, or other biochemical products or chemical associations, either alone or in any combination, in order to identify individuals who use, abuse, misuse, or are dependent on alcohol, may be a basis for identifying those who will respond to treatment with any 5-HT-3 antagonist (including ondansetron) at any dose or dosage form. Such a test (including a blood test) can be anticipated to determine individuals with an alcohol use, abuse, or dependence disorder who will respond to treatment with a 5-HT-3 antagonist (including ondansetron). Such individuals can be identified by means of the genetic screening and then provided with ondansetron.

The present invention further encompasses a method whereby genetic screening is used to identify any polymorphisms within the serotonin system or their related miRNA, mRNA, ncRNA, or protein expressions, levels, or states of function, or other biochemical products or chemical associations, either alone or in any combination, in order to identify individuals who use, abuse, misuse, or are dependent on alcohol or any other substance or have a habit-forming behavior (including but not limited to obesity, gambling, or computer or electronic addictions), may be a basis for identifying individuals who will respond to treatment with any serotonergic agent, compound, or drug at any dose or dosage form. Such a test (including a blood test) can be anticipated to determine individuals who will respond to treatment for any addictive behavior with any serotonergic agent, compound, or drug.

The present invention further encompasses a method whereby genetic screening is used to identify 5'-HTTLPR and rs1042173 polymorphisms or their related miRNA, mRNA, or protein expressions, levels, or states of function, or other biochemical products or chemical associations, either alone or in any combination, in order to identify individuals who use, abuse, misuse, or are dependent on alcohol or any other substance or have a habit-forming behavior (including but not limited to obesity, gambling, or computer or electronic addictions), may be a basis for identifying those susceptible to adverse events or side effects or optimizing treatment with any serotonergic agent, compound, or drug at any dose or dosage form. Such a test (including a blood test) can be anticipated to determine individuals who will not respond to treatment with a serotonergic agent, compound, or drug, or individuals who will need additional measures to optimize the success of treatment with any serotonergic agent, compound, or drug.

The present invention further encompasses a method whereby genetic screening is used to identify 5'-HTTLPR and rs1042173 polymorphisms, or any other polymorphisms in co-modulating neurotransmitter systems (i.e., dopamine, GABA, glutamate, opioids, and cannabinoids) or their related miRNA, mRNA, ncRNA, or protein expressions, levels, or states of function, or other biochemical products or chemical associations, either alone or in any combination, in order to identify individuals who use, abuse, misuse, or are dependent on alcohol, may be a basis for identifying those who will respond to treatment with any 5-HT-3 antagonist (including ondansetron) in combination with any drug that affects these co-modulating systems (including but not limited to topiramate, baclofen, gabapentin, naltrexone, nalmefene, and rimonabant) at any dose or dosage form. Such a test (including a blood test) can be anticipated to determine individuals with an alcohol use, abuse, or dependence disorder who will respond to treatment with a 5-HT-3 antagonist (including ondansetron) plus any of these co-modulating agents or drugs. Individuals with alcohol use, abuse, or dependence who have these polymorphisms identified by this genetic screening can than be provided with ondansetron plus the co modulating medication or drug, with the prediction that these combinations will be expected to be efficacious.

The present invention further encompasses a method whereby genetic screening is used to identify 5'-HTTLPR and rs1042173 polymorphisms, or any other polymorphisms in co-modulating neurotransmitter systems (i.e., dopamine, GABA, glutamate, opioids, and cannabinoids) or their related miRNA, mRNA, ncRNA, or protein expressions, levels, or states of function, or other biochemical products or chemical associations, either alone or in any combination, in order to identify individuals who use, abuse, misuse, or are dependent on alcohol, may be a basis for identifying those who will be susceptible to adverse events or not respond to treatment with any 5-HT-3 antagonist (including ondansetron) in combination with any drug that affects these co-modulating systems (including but not limited to topiramate, baclofen, gabapentin, naltrexone, nalmefene, and rimonabant) at any dose or dosage form. Such a test (including a blood test) can be anticipated to determine individuals who will not respond to treatment with a 5-HT-3 antagonist (including ondansetron) plus any of these co-modulating agents or drugs, or who will need additional measures to optimize treatment to these compounds. Individuals with substance use, abuse, dependence or any habit-forming behavior who have these polymorphisms identified by this genetic screening can either be screened out of being provided the combined treatment or be given additional measures to optimize their treatment.

The present invention further encompasses a method whereby genetic screening is used to identify 5'-HTTLPR and rs1042173 polymorphisms, or any other polymorphisms in co-modulating neurotransmitter systems (i.e., dopamine, GABA, glutamate, opioids, and cannabinoids) or their related miRNA, mRNA, ncRNA, or protein expressions, levels, or states of function, or other biochemical products or chemical associations, either alone or in any combination, is used to produce a biomarker (including a blood test) to determine, ascertain, or evaluate consumption level or diagnosis of alcohol use, abuse, misuse, or dependence.

The present invention further encompasses a method whereby genetic screening is used to identify 5'-HTTLPR and rs1042173 polymorphisms, or any other polymorphisms in co-modulating neurotransmitter systems (i.e., dopamine, GABA, glutamate, opioids, and cannabinoids) or their related miRNA, mRNA, ncRNA, or protein expressions, levels, or states of function, or other biochemical products or chemical associations, either alone or in any combination, is used to produce a biomarker (including a blood test) to determine, ascertain, or evaluate consumption level or diagnosis of substance use, abuse, misuse, or dependence or habit-forming behavior.

The present invention further encompasses a method whereby genetic screening is used to identify 5'-HTTLPR and rs1042173 polymorphisms, or any other polymorphisms in co-modulating neurotransmitter systems (i.e., dopamine, GABA, glutamate, opioids, and cannabinoids) or their related miRNA, mRNA, ncRNA, or protein expressions, levels, or states of function, or other biochemical products or chemical associations, either alone or in any combination, in order to identify individuals with substance use, abuse, misuse, or dependence or any habit-forming behavior, may be a basis for identifying those who will respond to treatment with any 5-HT-3 antagonist (including ondansetron) in combination with any drug that affects these co-modulating systems (including but not limited to topiramate, baclofen, gabapentin, naltrexone, nalmefene, and rimonabant) at any dose or dosage form. Such a test (including a blood test) can be anticipated to determine individuals with substance use, misuse, abuse, or dependence or any habit-forming disorder who will respond to treatment with a 5-HT-3 antagonist (including ondansetron) plus any of these co-modulating agents or drugs. Individuals with substance use, abuse, or dependence or any habit-forming behavior who have these polymorphisms identified by this genetic screening can than be provided with ondansetron plus the co modulating medication or drug, with the prediction that these combinations will be expected to be efficacious.

The present invention further encompasses a method whereby genetic screening is used to identify 5'-HTTLPR and rs1042173 polymorphisms, or any other polymorphisms in co-modulating neurotransmitter systems (i.e., dopamine, GABA, glutamate, opioids, and cannabinoids) or their related miRNA, mRNA, ncRNA, or protein expressions, levels, or states of function, or other biochemical products or chemical associations, either alone or in any combination, in order to identify individuals with substance use, abuse, misuse, or dependence or any habit-forming behavior, may be a basis for identifying those who will be susceptible to adverse events or side effects or who will not respond to treatment with any 5-HT-3 antagonist (including ondansetron) in combination with any drug that affects these co-modulating systems (including but not limited to topiramate, baclofen, gabapentin, naltrexone, nalmefene, and rimonabant) at any dose or dosage form. Such a test (including a blood test) can be anticipated to determine individuals with substance use, misuse, abuse, or dependence or any habit-forming disorder who will not respond to treatment with a 5-HT-3 antagonist (including ondansetron) plus any of these co-modulating agents or drugs, or who will require additional measures to optimize treatment. Individuals with substance use, abuse, dependence, or any habit-forming behavior who have these polymorphisms identified by this genetic screening can either be screened out of being provided the combined treatment or be given additional measures to optimize their treatment.

The present invention encompasses the use of ondansetron as well as other drugs. In one aspect, combinations of drugs are used. The present invention encompasses the use of combinations of drugs or compounds to treat addictive and compulsive diseases and disorders, particular alcohol-related diseases and disorders. The present invention further encompasses the use of adjunctive treatments and therapy such as psychosocial management regimes, hypnosis, and acupuncture.

In one embodiment, the present invention provides compositions and methods for treating alcohol-related diseases and disorders using pharmaceutical compositions comprising effective amounts of ondansetron, topiramate and/or naltrexone.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present invention has application for both human and veterinary use.

For example, in one embodiment relating to oral administration to humans, a dosage of between approximately 0.1 and 300 mg/kg/day, or between approximately 0.5 and 50 mg/kg/day, or between approximately 1 and 10 mg/kg/day, is generally sufficient, but will vary depending on such things as the disorder being treated, the length of treatment, the age, sex, weight, and/or health of the subject, etc. The drugs can be administered in formulations that contain all drugs being used, or the drugs can be administered separately. In some cases, it is anticipated that multiple doses/times of administration will be required or useful. The present invention further provides for varying the length of time of treatment.

Topiramate is disclosed herein as a drug useful in combination drug therapy. In one embodiment, topiramate is provided at a dosage ranging from about 15 mg/day to about 2500 mg/day. In one aspect, topiramate is administered at a dosage ranging from about 25 mg/day to about 1000 mg/day. In yet another aspect, topiramate is administered at a dosage ranging from about 50 mg/day to about 500 mg/day. In one aspect, topiramate is administered at a dosage of about 400 mg/day. In another aspect, topiramate is administered at a dosage of 400 mg/day. In a further aspect, topiramate is administered at a dosage of about 300 mg/day. In yet a further aspect, topiramate is administered at a dosage of about 275 mg/day. In one aspect, topiramate is administered at a dose of about 1 mg/day. In one aspect, up to about 300 mg/day is administered.

In one embodiment, topiramate is provided at a dose of about 1 mg/kg. In one aspect, topiramate is provided at a dose of about 10 mg/kg. In one aspect, topiramate is provided at a dose of about 100 mg/kg. In one embodiment, topiramate is administered at a dosage ranging from about 0.1 mg/kg/day to about 100 mg/kg/day.

Topiramate ($C_{12}H_{21}NO_8S$; IUPAC name: 2,3:4,5-Bis-O-(1-methylethylidene)-beta-D-fructopyranose sulfamate; CAS Registry No. 97240-79-4) has the following structure:

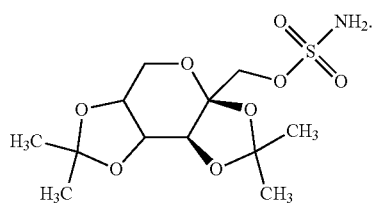 [SMILES: CC1(C)OC2CO[C@@]3(COS(N)(=O)=O)OC(C)(C)O[C@H]3C2O1]

An important aspect of psychotropic drugs is to produce weight gain. These increases in weight gain can induce a range of metabolic problems including abnormal sugar, fat, and carbohydrate metabolism. Because topiramate can cause weight loss and improve endocrine function, it is proposed herein that topiramate may be used to ameliorate weight gain caused by other psychotropic drugs with which it is combined as well as alcohol and any other abused drugs.

An important adverse event of topiramate is cognitive impairment. In the general population, this is reported by 2.4% of individuals who take topiramate (Johnson & Johnson Pharmaceutical Research & Development. Investigator's Brochure: Topiramate (RWJ-17021-000), 10th ed.; December 2005). In the substance abuse field, the occurrence rate of cognitive impairment is about 18.7% (Johnson B A, Ait-Daoud N, Bowden C L et al. Oral topiramate for treatment of alcohol dependence: a randomized controlled trial. Lancet 2003, 361:1677-1685). Topiramate-associated cognitive effects are due to its anti-glutaminergic properties. It is, therefore, not obvious that ondansetron, a serotonin-3 receptor antagonist, will alleviate these complaints of cognitive impairment. Ondansetron appears to have cholinergic effects, perhaps though interactions with the GABA system, that seem to ameliorate topiramate-associated cognitive impairment. Hence, it is to be expected that the rate of cognitive impairment reported by this triple combination would be less than that for topiramate on its own.

Ondansetron is disclosed herein as a drug useful alone or as part of combination drug therapy. Ondansetron is a 5-HT$_3$ receptor antagonist and has functionally opposite effects to SSRIs and blocks serotonin agonism at the 5-HT$_3$ receptor. The dosage and treatment regimen for administering ondansetron when it is being used as one compound of a combination therapy can be varied based on the other drug or drugs with which it is being administered, or based on other criteria such as the age, sex, health, and weight of the subject. The present invention therefore provides for the use of ondansetron at varying doses such as about 0.01 μg/kg, about 0.1 μg/kg, about 1.0 μg/kg, about 5.0 μg/kg, about 10.0 μg/kg, about 0.1 mg/kg, about 1.0 mg/kg, about 5.0 mg/kg, and about 10.0 mg/kg. In another embodiment, ondansetron is administered at a dosage ranging from about 0.01 μg/kg to about 100 μg/kg per application. In one aspect, ondansetron is administered at a dosage ranging from about 0.1 μg/kg to about 10.0 μg/kg per application. In yet another aspect, ondansetron is administered at a dosage ranging from about 1.0 μg/kg to about 5.0 μg/kg per application. In a further aspect, ondansetron is administered at a dosage of about 4.0 μg/kg per application. In another aspect, ondansetron is administered at a dosage of about 3.0 μg/kg per application. In one aspect, ondansetron is administered at a dose of about 4 μg/kg twice daily (about 0.25 to 0.6 mg twice daily for body weights between about 50 kg and 150 kg).

Ondansetron ($C_{18}H_{19}N_3O$; CAS Registry No. 99614-02-5; IUPAC name: 9-methyl-3-[(2-methyl-1H-imidazol-1-yl)methyl]-1,2,3,9-tetrahydrocarbazol-4-one) has the following structure:

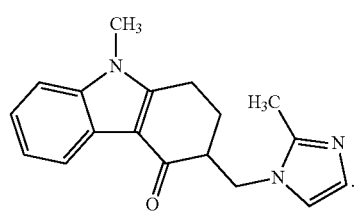 [SMILES: Cc1nccn1CC1CCc2c(c3ccccc3n2C)C1=O]

The present invention further provides for the use of other drugs such as naltrexone as part of the drug combination therapy disclosed herein. In one embodiment, naltrexone is administered at a dose of about 10 mg/day. In one aspect, naltrexone is administered at a dosage at a dosage of about 50 mg/day. In one aspect, naltrexone is administered at a dosage of about 100 mg/day. In one aspect, naltrexone is administered at a dosage ranging from about 1 mg to about 300 mg per application. In another aspect, naltrexone is administered at a dosage ranging from about 10 mg to about 50 mg per application. In a further aspect of the invention, naltrexone is administered at a dosage of about 25 mg per application. In one embodiment, naltrexone is administered at least once a month. In a further embodiment, naltrexone is administered once a month. In one embodiment, naltrexone is administered at least once a week. In another embodiment, naltrexone is administered at least once a day. In a further embodiment, naltrexone is administered at least twice a day. In one aspect, naltrexone is administered twice a day.

Naltrexone ($C_{20}H_{23}NO_4$; 17-(Cyclopropylmethyl)-4,5a-epoxy-3,14-dihydroxymorphinan-6-one hydrochloride; CAS Registry No. 16590-41-3) has the following structure:

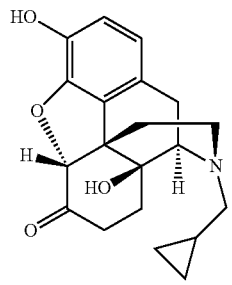

Naltrexone also has important adverse events—nausea and vomiting—that reduce compliance to it. Indeed, about 15% of individuals in alcohol trials are unable to tolerate a naltrexone dose of 50 mg/day. This has led to the development of depot formulations that release naltrexone slowly to reduce the incidence of nausea and vomiting. Nevertheless, these depot formulation(s) appear to have similar compliance rates to the oral form of the medication. Importantly, ondansetron reduces nausea and decreases vomiting by slowing gut motility. Therefore, a combination that adds ondansetron to naltrexone will diminish the nausea and vomiting caused by naltrexone. This is an important therapeutic advance because many more people will be able to tolerate the treatment due to increased compliance, and higher doses than the typically administered naltrexone dose of 50 mg/day can be given to improve the therapeutic response.

In one embodiment, the alcohol-related disease or disorder being treated includes, but is not limited to, early-onset alcoholic, late-onset alcoholic, alcohol-induced psychotic disorder with delusions, alcohol abuse, excessive drinking, heavy drinking, problem drinking, alcohol intoxication, alcohol withdrawal, alcohol intoxication delirium, alcohol withdrawal delirium, alcohol-induced persisting dementia, alcohol-induced persisting amnestic disorder, alcohol dependence, alcohol-induced psychotic disorder with hallucinations, alcohol-induced mood disorder, alcohol-induced or associated bipolar disorder, alcohol-induced or associated posttraumatic stress disorder, alcohol-induced anxiety disorder, alcohol-induced sexual dysfunction, alcohol-induced sleep disorder, alcohol-induced or associated gambling disorder, alcohol-induced or associated sexual disorder, alcohol-related disorder not otherwise specified, alcohol intoxication, and alcohol withdrawal. In one aspect, the alcohol-related disease or disorder is early onset alcoholic. In another aspect, the alcohol-related disease or disorder is late onset alcoholic.

In one embodiment, the present invention provides compositions and methods for reducing the frequency of alcohol consumption compared with the frequency of alcohol consumption before the treatment. One of ordinary skill in the art will appreciate that the frequency can be compared with prior consumption by the subject or with consumption by a control subject not receiving the treatment. In one aspect, the type of alcohol consumption is heavy drinking. In another aspect, it is excessive drinking.

In one embodiment, the present invention provides compositions and methods for reducing the quantity of alcohol consumed in a subject compared with the amount of alcohol consumed before the treatment or compared with the alcohol consumption by a control subject not receiving the treatment.

One of ordinary skill in the art will appreciate that in some instances a subject being treated for and addictive disorder is not necessarily dependent. Such subjects include, for example, subjects who abuse alcohol, drink heavily, drink excessively, are problem drinkers, or are heavy drug users. The present invention provides compositions and methods for treating or preventing these behaviors in non-dependent subjects.

In one embodiment of the invention, the present invention provides compositions and methods for improving the physical or psychological sequelae associated with alcohol consumption compared with a control subject not receiving the treatment.

In one embodiment, the present invention provides compositions and methods for increasing the abstinence rate of a subject compared with a control subject not receiving the treatment.

In one embodiment, the present invention provides compositions and methods for reducing the average level of alcohol consumption in a subject compared with the level of alcohol consumption before the treatment or compared with the level of alcohol consumption by a control subject not receiving the treatment.

In one embodiment, the present invention provides compositions and methods for reducing alcohol consumption and for increasing abstinence compared with the alcohol consumption by the subject before treatment or with a control subject not receiving the treatment.

In one embodiment, the present invention provides compositions and methods for treating a subject with a predisposition to early-onset alcoholism.

In one embodiment, the present invention provides compositions and methods for treating a subject with a predisposition to late-onset alcoholism.

One of ordinary skill in the art will appreciate that there are multiple parameters or characteristics of alcohol consumption which may characterize a subject afflicted with an alcohol-related disease or disorder. It will also be appreciated that combination therapies may be effective in treating more than one parameter, and that there are multiple ways to analyze the effectiveness of treatment. The parameters analyzed when measuring alcohol consumption or frequency of alcohol consumption include, but are not limited to, heavy drinking days, number of heavy drinking days, average drinking days, number of drinks per day, days of abstinence, number of individuals not drinking heavily or abstinent over a given time period, and craving. Both subjective and objective measures can be used to analyze the effectiveness of treatment. For example, a subject can self-report according to guidelines and procedures established for such reporting. The procedures can be performed at various times before, during, and after treatment. Additionally, assays are available for measuring alcohol consumption. These assays include breath alcohol meter readings, measuring serum CDT and GGT levels, and measuring 5-HTOL urine levels.

In some embodiments, a first compound and a second compound are administered nearly simultaneously. In other embodiments, a first compound is administered prior to the second compound. In yet other embodiments, the first compound is administered subsequent to the second compound. If three or more compounds are administered, one of ordinary skill in the art will appreciate that the three or more compounds can be administered simultaneously or in varying order.

In certain embodiments disclosed herein, an individual is given a pharmaceutical composition comprising a combination of two or more compounds to treat or prevent an addiction-related disease or disorder or impulse control-related disease or disorder. In some of these embodiments, each compound is a separate chemical entity. However, in other embodiments, the at least two compounds can be joined together by a chemical linkage, such as a covalent bond, so that the at least two different compounds form separate parts of the same molecule. In one aspect, the chemical linkage is selected such that after entry into the body, the linkage is broken, such as by enzymatic action, acid hydrolysis, base hydrolysis, or the like, and the two separate compounds are then formed.

Data from previous structure-activity relationship (SAR) studies within the art may be used as a guide to determine which compounds to use and the optimal position or positions on the molecules to attach the tether such that potency and selectivity of the compounds will remain high. The tether or linker moiety is chosen from among those of demonstrated utility for linking bioactive molecules together. Disclosed herein are representative compounds that can be attached together in different combinations to form heterobivalent therapeutic molecules.

Examples of linkers reported in the scientific literature include methylene (CH$_2$), linkers (Hussey et al., J. Am. Chem. Soc., 2003, 125:3692-3693; Tamiz et al., J. Med. Chem., 2001, 44:1615-1622), oligo ethyleneoxy O(—CH$_2$CH$_2$O—)$_n$ units used to link naltrexamine to other opioids, glycine oligomers of the formula —NH—(COCH$_2$NH)$_n$COCH$_2$CH$_2$CO—(NHCH$_2$CO)$_n$NH— used to link opioid antagonists and agonists together ((a) Portoghese et al., Life Sci., 1982, 31:1283-1286. (b) Portoghese et al., J. Med. Chem., 1986, 29:1855-1861), hydrophilic diamines used to link opioid peptides together (Stepinski et al., Internat. J. of Peptide & Protein Res., 1991, 38:588-92), rigid double stranded DNA spacers (Paar et al., J. Immunol., 2002, 169:856-864) and the biodegradable linker poly(L-lactic acid) (Klok et al., Macromolecules, 2002, 35:746-759). The attachment of the tether to a compound can result in the compound achieving a favorable binding orientation. The linker itself may or may not be biodegradable. The linker may take the form of a prodrug and be tunable for optimal release kinetics of the linked drugs. The linker may be either conformationally flexible throughout its entire length or else a segment of the tether may be designed to be conformationally restricted (Portoghese et al., J. Med. Chem., 1986, 29:1650-1653).

With respect to alcohol-related disorders, including but not limited to alcohol abuse and alcohol dependence, at least two compounds selected from the group consisting of topiramate, ondansetron, and naltrexone, and analogs, derivatives, and modifications thereof, and pharmaceutically acceptable salts thereof, can be used to decrease ethanol consumption associated with such alcohol-related disorders. In one aspect, topiramate and ondansetron are used. Accordingly, the present invention provides a method for treating or preventing alcohol-related disorders based on ethanol consumption, comprising administering to a subject in need of such treatment or prevention an effective amount of at least two compounds selected from the group consisting of topiramate, ondansetron, and naltrexone, and analogs, derivatives, and modifications thereof or a pharmaceutically acceptable salt thereof. In a further aspect, the combination pharmacotherapy treatment is used in conjunction with behavioral modification or therapy.

Additional types of compounds can be administered to treat further the addiction-related diseases and disorders or to treat other diseases and disorders. The additional types of compounds include, but are not limited to, adrenergics, adrenocortical steroids, adrenocortical suppressants, aldosterone antagonists, amino acids, analeptics, analgesics, anorectic compounds, anorexics, anti-anxiety agents, antidepressants, antihypertensives, anti-inflammatories, antinauseants, antineutropenics, antiobsessional agents, antiparkinsonians, antipsychotics, appetite suppressants, blood glucose regulators, carbonic anhydrase inhibitors, cardiotonics, cardiovascular agents, choleretics, cholinergics, cholinergic agonists, cholinesterase deactivators, cognition adjuvants, cognition enhancers, hormones, memory adjuvants, mental performance enhancers, mood regulators, neuroleptics, neuroprotectives, psychotropics, relaxants, sedative-hypnotics, stimulants, thyroid hormones, thyroid inhibitors, thyromimetics, cerebral ischemia agents, vasoconstrictors, and vasodilators.

In one embodiment, the present invention provides methods and compositions useful for decreasing mesocorticolimbic dopamine activity.

In one embodiment, the present invention provides methods and compositions useful for regulating mesocorticolimbic dopamine activity.

In one embodiment, the present invention provides methods and compositions useful for inhibiting glutamate function.

In one embodiment, the present invention provides methods and compositions useful for facilitating γ-amino-butyric acid activity.

In one embodiment, the present invention provides methods and compositions useful for regulating γ-amino-butyric acid activity.

The present invention provides for multiple methods for delivering the compounds of the invention. The compounds may be provided, for example, as pharmaceutical compositions in multiple formats as well, including, but not limited to, tablets, capsules, pills, lozenges, syrups, ointments, creams, elixirs, suppositories, suspensions, inhalants, injections (including depot preparations), and liquids.

The present invention further encompasses biologically active analogs, homologs, derivatives, and modifications of the compounds of the invention.

Methods for the preparation of such compounds are known in the art. In one aspect, the compounds are topiramate, naltrexone, and ondansetron.

The compositions and methods described herein for treating or preventing alcohol-related diseases and disorders are also useful for treating or preventing other addiction-related diseases and disorders and impulse control disorders. In one aspect, the compositions and methods elicit an indirect effect on CMDA neurons. Such effects may be elicited, for example, by regulating serotonergic, opiate, glutamate, or γ-amino-butyric acid receptors. In one aspect, the addictive diseases and disorders include eating disorders, impulse control disorders, nicotine-related disorders, methamphetamine-related disorders amphetamine-related disorders, cannabis-related disorders, cocaine-related disorders, hallucinogen use disorders, inhalant-related disorders, benzodiazepine abuse or dependence related disorders, and opioid-related disorders.

A list of types of drugs, and specific drugs within categories which are encompassed within the invention is provided below.

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate: Epinephryl Borate; Esproquin Hydrochloride; Etafedrine Hydrochloride: Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; Tipredane.

Adrenocortical suppressant: Aminoglutethimide; Trilostane.

Alcohol deterrent: Disulfiram.

Aldosterone antagonist: Canrenoate Potassium; Canrenone: Dicirenone; Mexrenoate Potassium; Prorenoate Potassium: Spironolactone.

Amino acid: Alanine; Aspartic Acid; Cysteine Hydrochloride; Cystine; Histidine; Isoleucine; Leucine; Lysine; Lysine Acetate; Lysine Hydrochloride; Methionine; Phenylalanine; Proline; Serine; Threonine; Tryptophan; Tyrosine; Valine.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazcpine; Carbaspirin Calcium: Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride: Epirizole; Ergotamine Tartrate; Ethoxazene Hydrochloride; Etofenamate; Eugenol; Fenoprofen; Fenoprofen Calcium; Fentanyl Citrate; Floctafenine: Flufenisal; Flunixin; Flunixin Meglumine; Flupirtine Maleate; Fluproquazone; Fluradoline Hydrochloride; Flurbiprofen; Hydromorphone Hydrochloride; lbufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate: Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol: Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac: Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propirarn Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride: Volazocinc; Xorphanol Mcsylate; Xylazinc Hydrochloride; Zenazocine Mesylate; Zomepirac Sodium; Zucapsaicin.

Anorectic compounds including dexfenfluramine.

Anorexic: Aminorex; Amphecloral; Chlorphentermine Hydrochloride; Clominorex; Clortennine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phenmetrazine Hydrochloride; Phentermine; Sibutramine Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; Zalospirone Hydrochloride.

Anti-cannabis agent: Rimonabant and other useful drugs, including drugs regulating the cannabinoid receptors.

Antidepressant: Adatanserin Hydrochloride; Adinazolam; Adinazolam Mesylate; Alaproclate; Aletamine Hydrochloride; Amedalin Hydrochloride; Amitriptyline Hydrochloride; Amoxapine; Aptazapine Maleate; Azaloxan Fumarate; Azepindole; Azipramine Hydrochloride; Bipenarnol Hydrochloride; Bupropion Hydrochloride; Butacetin; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fehmetozole Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Milacemide Hydrochloride; Minaprine Hydrochloride; Mirtazapine; Moclobemide; Modaline Sulfate; Napactadinc Hydrochloride; Napamezolc Hydrochloride; Ncfazodonc Hydrochloride; Nisoxetine; Nitrafudam Hydrochloride; Nomifensine Maleate; Nortriptyline Hydrochloride; Octriptyline Phosphate: Opipramol Hydrochloride; Oxaprotiline Hydrochloride; Oxypertine; Paroxetine; Phenelzine Sulfate; Pirandamine Hydrochloride; Pizotyline; Pridefine Hydrochloride; Prolintane Hydrochloride; Protriptyline Hydrochloride; Quipazine Maleate; Rolicyprine; Seproxetine Hydrochloride; Sertraline Hydrochloride; Sibutramine Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine; Trimipramine Maleate; Venlafaxine Hydrochloride; Viloxazine Hydrochloride; Zimeldine Hydrochloride; Zometapine.

Antihypertensive: Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril;

Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide: Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan: Fosinopril Sodium; Fosinoprilat; Guanabenz; Guanabenz Acetate; Guanacline Sulfate; Guanadrel Sulfate: Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Mctipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Irimoxamine Hydrochloride; Tripamide; Xipamide; Zankiren Hydrochloride; Zofenoprilat Arginine.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprcdnisolonc Suleptanatc; Momiflumatc; Nabumetonc; Naproxen; Naproxen Sodium; Naproxol; Nimazone; OLsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antinauseant: Buclizine Hydrochloride; Cyclizine Lactate: Naboctate Hydrochloride.

Antineutropenic: Filgrastim; Lenograstim; Molgramostim; Regramostim; Sargramostim.

Antiobsessional agent: Fluvoxamine Maleate.

Antiparkinsonian: Benztropine Mesylate; Biperiden; Biperiden Hydrochloride; Biperiden Lactate; Cannantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Quinetorane Hydrochloride; Ropinirole Hydrochloride; Selegiline Hydrochloride; Tolcapone; Trihexyphenidyl Hydrochloride. Antiperistaltic: Difenoximide Hydrochloride; Difenoxin; Diphenoxylate Hydrochloride; Fluperamide; Lidamidine Hydrochloride; Loperamide Hydrochloride; Malethamer: Nufenoxole; Paregoric.

Antipsychotic: Acetophenazine Maleate; Alentemol Hydrobromide; Alpertine; Azaperone; Batelapine Maleate; Benperidol; Benzindopyrine Hydrochloride; Brofbxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Dccanoatc; Fluphcnazinc Enanthatc; Fluphenazine Hydrochloride; Fluspiperonc; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palniitate; Piquindone Hydrochloride; Prochlorperazine Edisylate; Prochlorperazine Maleate; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; Ziprasidone Hydrochloride.

Appetite suppressant: Dexfenfluramine Hydrochloride; Phendimetrazine Tartrate; Phentermine Hydrochloride.

Blood glucose regulators: Human inaulin; Glucagon; Tolazamide; Tolbutamide; Chloropropamide; Acetohexamide and Glipizide.

Carbonic anhydrase inhibitor: Acetazolamide; Acetazolamide Sodium, Dichlorphenamide; Dorzolamide Hydrochloride; Methazolamide; Sezolarmide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Butoprozine Hydrochloride; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride: Recainam Tosylate; Risotilide Hydrochloride; Ropitoin Hydrochloride; Sematilide Hydrochloride; Suricainide Maleate; Tocainide; Tocainide Hydrochloride; Transcainide.

Cardiotonic: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Peirinone Hydrochloride; Pimobendan; Piroximone; Prinoxodan; Proscillaridin; Quazinone; Tazolol Hydrochloride; Vesnarinone.

Cardiovascular agent: Dopexamine; Dopexamine Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Cholinergic agonist: Xanomeline; Xanomeline Tartrate.

Cholinesterase Deactivator: Obidoxime Chloride; Pralidoxime Chloride; Pralidoxime Iodide: Pralidoxime Mesylate.

Coccidiostat: Arprinocid; Narasin; Semduramicin; Semduramicin Sodium.

Cognition adiuvant: Ergoloid Mesylates; Piracetam; Pramiracetam Hydrochloride; Pramiracetam Sulfate; Tacrine Hydrochloride.

Cognition enhancer: Besipirdine Hydrochloride; Linopirdine; Sibopirdine.

Dopamine receptor agonist: cabergoline (Dostinex)

Hormone: Diethylstilbestrol; Progesterone; 17-hydroxy progesterone; Medroxyprogesterone; Norgestrel; Norethynodrel; Estradiol; Megestrol (Megace); Norethindrone; Levonorgestrel; Ethyndiol; Ethinyl estradiol; Mestranol; Estrone; Equilin; 17-alpha-dihydroequilin; equilenin; 17-alpha-dihydroequilenin; 17-alpha-estradiol; 17-beta-estradiol; Leuprolide (lupron); Glucagon; Testolactone; Clomiphene; Han memopausal gonadotropins; Human chorionic gonadotropin; Urofollitropin; Bromocriptine; Gonadorelin; Luteinizing hormone releasing hormone and analogs: Gonadotropins; Danazol; Testosterone; Dehydroepiandrosterone: Androstenedione; Dihydroestosterone; Relaxin; Oxytocin; Vasopressin; Folliculostatin; Follicle regulatory protein; Gonadoctrinins; Oocyte maturation inhibitor; Insulin growth factor; Follicle Stimulating Hormone; Luteinizing hormone; Tamoxifen.; Corticorelin Ovine Triftutate; Cosyntropin; Metogest; Pituitary, Posterior; Seractide Acetate; Somalapor; Somatrem; Somatropin; Somenopor; Somidobove.

Memory adjuvant: Dimoxamine Hydrochloride: Ribaminol.

Mental performance enhancer: Aniracetam.

Mood regulator: Fengabine.

Neuroleptic: Duoperone Fumarate; Risperidone.

Neuroprotective: Dizocilpine Maleate.

Psychotropic: Minaprine.

Relaxant: Adiphenine Hydrochloride; Alcuronium Chloride; Aminophylline; Azumolene Sodium; Baclofen: Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalanide; Fenyripol Hydrochloride; Fetoxylate Hydrochloride; Flavoxate Hydrochloride; Fletazepam; Flumetramide; Flurazepam Hydrochloride; Hexafluorenium Bromide; Isomylamine Hydrochloride; Lorbamate; Mebeverine Hydrochloride; Mesuprine Hydrochloride; Metaxalone; Methocarbamol; Methixene Hydrochloride; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; Xilobam.

Sedative-hypnotic: Allobarbital; Alonimid: Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam; Ethchlorvynol; Etomidate; Fenobam; Flunitrazepam; Fosazepam; Glutethimide; Halazepam; Lormetazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Thalidomide; Tracazolate; Trepipam Maleate; Triazolam; Tricetamide; Triclofos Sodium; Trimctozinc; Uldazcpam; Zaleplon; Zolazcpam Hydrochloride; Zolpidem Tartrate.

Serotonin antagonist: Altanserin Tartrate; Amesergide; Kctanscrin; Ritanserin.

Serotonin inhibitor: Cinanserin Hydrochloride; Fenclonine; Fonazine Mesylate; Xylamidine Tosylate.

Serotonin receptor antagonist: Tropanserin Hydrochloride.

Stimulant: Amfonelic Acid; Amphetamine Sulfate; Ampyzine Sulfate; Arbutamine Hydrochloride; Azabon; Caffeine; Ceruletide; Ceruletide Diethylamine; Cisapride; Dazopride Fumarate; Dextroamphetamine; Dextroamphetamine Sulfate; Difluanine Hydrochloride; Dimefline Hydrochloride; Doxapram Hydrochloride; Etryptamine Acetate; Ethamivan; Fenethylline Hydrochloride; Flubanilate Hydrochloride; Flurothyl; Histamine Phosphate; Indriline Hydrochloride; Mefexamide; Methamphetamine Hydrochlo ride;

Methylphenidate Hydrochloride; Pemoline; Pyrovalerone Hydrochloride; Xamoterol; Xamoterol Fumarate. Synergist; Proadifen Hydrochloride.

Thyroid hormone: Levothyroxine Sodium; Liothyronine Sodium; Liotrix.

Thyroid inhibitor: Methimazole; Propyithiouracil.

Thyromimetic: Thyromedan Hydrochloride.

Cerebral ischemia agents: Dextrorphan Hydrochloride.

Vasoconstrictor: Angiotensin Amide; Felypressin; Methysergide; Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Diltiazem Hydrochloride; Dipyridamole; Droprenilamine; Erythrityl Tetranitrate; Felodipinc; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride; Mixidine; Nafronyl Oxalate; Nicardipine Hydrochloride; Nicergoline; Nicorandil; Nicotinyl Alcohol; Nifedipine; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; Xanthinol Niacinate.

Assays and methods for testing compounds of the invention are described herein or are known in the art. For example, see Lippa et al., U.S. Pat. Pub. No. 2006/0173-64, published Aug. 3, 2006.

The invention further encompasses treating and preventing obesity, i.e., for affecting weight loss and preventing weight gain. Obesity is a disorder characterized by the accumulation of excess fat in the body. Obesity has been recognized as one of the leading causes of disease and is emerging as a global problem. Increased instances of complications such as hypertension, non-insulin-dependent diabetes mellitus, arteriosclerosis, dyslipidemia, certain forms of cancer, sleep apnea, and osteoarthritis have been related to increased instances of obesity in the general population In one aspect, the invention encompasses administering to a subject in need thereof a combination therapy to induce weight loss. For example, subjects having a BMI of greater than about 25 (25.0-29.9 is considered overweight) are identified for treatment. In one aspect, the individuals have a BMI of greater than 30 (30 and above is considered obese). In another aspect, a subject may be targeted for treatment to prevent weight gain. In one embodiment, an individual is instructed to take at least one compound of the invention at least once daily and at least a second compound of the invention at least once daily. The compound may be in the form of, for example, a tablet, a lozenge, a liquid, etc. In one aspect, a third compound is also taken daily. In one embodiment, compounds may be taken more than once daily. In another embodiment, compounds are taken less than once daily. The dosages can be determined based on what is known in the art or what is determined to be best for a subject of that age, sex, health, weight, etc. Compounds useful for treating obesity according to the methods of the invention, include, but are not limited to, topiramate, naltrexone, and ondansetron. See Weber (U.S. Pat. Pub. No. 20070275970) and McElroy (U.S. Pat. No. 6,323,236) for additional information and techniques for administering drugs useful for treating obesity, addictive disorders, and impulse control disorders, and for determining dosage schemes.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Psychosocial Intervention and Management

The drug combination treatments of the present invention can be further supplemented by providing to subjects a form of psychosocial intervention and/or management, such as Brief Behavioral Compliance Enhancement Treatment (BBCET). BBCET, a standardized, manual-guided, brief (i.e., delivered in about 15 minutes), psychosocial adherence enhancement procedure, emphasizes that medication compliance is crucial to changing participants' drinking behavior (Johnson et al., Brief Behavioral Compliance Enhancement Treatment (BBCET) manual. In: Johnson B A, Ruiz P. Galanter M, eds. Handbook of clinical alcoholism treatment. Baltimore, Md.: Lippincott Williams & Wilkins; 2003, 282-301). Brief interventions (Edwards et al., J. Stud. Alcohol. 1977, 38:1004-1031) such as BBCET, have been shown to benefit treatment of alcohol dependence. BBCET was modeled on the clinical management condition in the National Institute of Mental Health collaborative depression trial, which was used as an adjunct to the medication condition for that study (Fawcett et al. Psychopharmacol Bull. 1987, 23:309-324). BBCET has been used successfully as the psychosocial treatment platform in the single-site and multi-site efficacy trials of topiramate for treating alcohol dependence (Johnson et al., Lancet. 2003, 361:1677-1685; Johnson et al., JAMA, 2007, 298:1641-1651). It is delivered by trained clinicians, including nurse practitioners and other non-specialists. Uniformity and consistency of BBCET delivery are ensured by ongoing training and supervision. BBCET is copyrighted material (Johnson et al., Brief Behavioral Compliance Enhancement Treatment (BBCET) manual. In: Johnson B A, Ruiz P, Galanter M, eds. Handbook of clinical alcoholism treatment. Baltimore, Md.: Lippincott Williams & Wilkins; 2003, 282-301).

The present invention further encompasses the use of psychosocial management regimens other than BBCET, including, but not limited to, Cognitive Behavioral Coping Skills Therapy (CBT) (Project MATCH Research Group. Matching Alcoholism Treatments to Client Heterogeneity: Project MATCH posttreatment drinking outcomes. J Stud Alcohol. 1997; 58:7-29), Motivational Enhancement Therapy (MET) (Project MATCH Research Group. Matching Alcoholism Treatments to Client Heterogeneity: Project MATCH posttreatment drinking outcomes. J. Stud. Alcohol. 1997, 58:7-29), Twelve-Step Facilitation Therapy (TSF) (Project MATCH Research Group. Matching Alcoholism Treatments to Client Heterogeneity: Project MATCH posttreatment drinking outcomes. J. Stud. Alcohol. 1997, 58:7-29), Combined Behavioral Intervention (CBI), (Anton et al., JAMA, 2006, 295:2003-2017) Medical Management (MM) (Anton et al., JAMA, 2006, 295:2003-2017), or the Biopsychosocial, Report, Empathy, Needs, Direct advice, and Assessment (BRENDA) model (Garbutt et al., JAMA, 2005, 293:1617-1625). The present invention further encompasses the use of alternative interventions such as hypnosis or acupuncture to assist in treating an addictive disease or disorder.

The psychosocial management programs can be used before, during, and after treating the subject with the combination drug therapy of the invention.

One of ordinary skill in the art will recognize that psychosocial management procedures, as well as alternative interventions such as hypnosis or acupuncture, can also be used in conjunction with combination drug therapy to treat addictive and impulse-related disorders other than alcohol-related diseases and disorders.

The present invention further encompasses the use of combination pharmacotherapy and behavioral (psychosocial) intervention or training to treat other addictive and/or impulse control disorders.

For example, binge eating disorder (BED) is characterized by discrete periods of binge eating during which large amounts of food are consumed in a discrete period of time and a sense of control over eating is absent. Persons with bulimia nervosa have been reported to have electroencephalographic abnormalities and to display reduced binge eating in response to the anti-epileptic drug phenytoin. In addition, in controlled trials in patients with epilepsy, topiramate was associated with suppression of appetite and weight loss unrelated to binge eating. Ondansetron has been shown to reduce binge eating.

BED is a subset of a larger classification of mental disorders broadly defined as Impulse Control Disorders (ICDs) characterized by harmful behaviors performed in response to irresistible impulses. It has been suggested that ICDs may be related to obsessive-compulsive disorder or similarly, maybe forms of obsessive-compulsive disorders. It has also been hypothesized that ICDs may be related to mood disorder or may be forms of affective spectrum disorder, a hypothesized family of disorders sharing at least one common physiologic abnormality with major depression. In the Diagnostic and Statistical Manual of Mental Disorders (DSM-IV), the essential feature of an ICD is the failure to resist an impulse, drive, or temptation to perform an act that is harmful to the person or to others. For most ICDs, the individual feels an increasing sense of tension or arousal before committing the act, and then experiences pleasure, gratification, or release at the time of committing the act. After the act is performed, there may or may not be regret or guilt. ICDs are listed in a residual category, the ICDs Not Elsewhere Classified, which includes intermittent explosive disorder (IED), kleptomania, pathological gambling, pyromania, trichotillomania, and ICDs not otherwise specified (NOS). Examples of ICDs NOS are compulsive buying or shopping, repetitive self-mutilation, nonparaphilic sexual addictions, severe nail biting, compulsive skin picking, personality disorders with impulsive features, attention deficit/hyperactivity disorder, eating disorders characterized by binge eating, and substance use disorders.

Many drugs can cause physical and/or psychological addiction. Those most well known drugs include opiates, such as heroin, opium and morphine; sympathomimetics, including cocaine and amphetamines; sedative-hypnotics, including alcohol, benzodiazepines, and barbiturates; and nicotine, which has effects similar to opioids and sympathomimetics. Drug addiction is characterized by a craving or compulsion for taking the drug and an inability to limit its intake. Additionally, drug dependence is associated with drug tolerance, the loss of effect of the drug following repeated administration, and withdrawal, the appearance of physical and behavioral symptoms when the drug is not consumed. Sensitization occurs if repeated administration of a drug leads to an increased response to each dose. Tolerance, sensitization, and withdrawal are phenomena evidencing a change in the central nervous system resulting from continued use of the drug. This change motivates the addicted individual to continue consuming the drug despite serious social, legal, physical, and/or professional consequences.

Attention-deficit disorders include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder, and Disruptive Behavior Disorder not otherwise specified (NOS).

Depressive disorders include, but are not limited to, Major Depressive Disorder, Recurrent; Dysthymic Disorder; Depressive Disorder not otherwise specified (NOS); and Major Depressive Disorder, Single Episode.

Parkinson's disease includes, but is not limited to, neuroleptic-induced parkinsonism.

Addictive disorders include, but are not limited to, eating disorders, impulse control disorders, alcohol-related disorders, nicotine-related disorders, amphetamine-related disorders, cannabis-related disorders, cocaine-related disorders, gambling, sexual disorders, hallucinogen use disorders, inhalant-related disorders, and opioid-related disorders, all of which are further subclassified as listed below.

Eating disorders include, but are not limited to, Bulimia Nervosa, Nonpurging Type; Bulimia Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication. Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

Cannabis-related disorders include, but are not limited to, Cannabis Dependence; Cannabis Abuse; Cannabis Intoxication; Cannabis Intoxication Delirium; Cannabis-Induced Psychotic Disorder, with delusions; Cannabis-Induced Psychotic Disorder with hallucinations; Cannabis-Induced Anxiety Disorder; Cannabis-Related Disorder not otherwise specified (NOS); and Cannabis Intoxication.

Cocaine-related disorders include, but are not limited to, Cocaine Dependence, Cocaine Abuse, Cocaine Intoxication. Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction. Cocaine-Induced Sleep Disorder, Cocaine-Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorder with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant-Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder, with delusions, Opioid-Induced Psychotic Disorder with hallucinations, Opioid-Induced Anxiety Disorder, Opioid-Related Disorder not otherwise specified (NOS), Opioid Intoxication, and Opioid Withdrawal.

Tic disorders include, but are not limited to, Tourette's Disorder, Chronic Motor or Vocal Tic Disorder, Transient Tic Disorder, Tic Disorder not otherwise specified (NOS), Stuttering, Autistic Disorder, and Somatization Disorder.

The present invention further encompasses the treatment of at least two addictive diseases or disorders or impulse control disorders simultaneously. For example, the present invention provides for the simultaneous treatment of alcohol related disorders and weight control (see Examples).

The present invention also encompasses the use of the compounds and combination therapies of the invention in circumstances where mandatory treatment may be applicable. For example, a court may require that a subject be treated or take part in a treatment program using compounds or combination therapies of the invention as part of a mandated therapy related to alcohol abuse, excessive drinking, drug use, etc. More particularly, the invention encompasses forensic uses where a court would require a subject who has been convicted of driving under the influence to be subjected to the methods of the invention as part of a condition of bail, probation, treatment, etc.

The invention also encompasses the use of pharmaceutical compositions comprising compounds of the invention to practice the methods of the invention, the compositions comprising at least one appropriate compound and a pharmaceutically-acceptable carrier.

Other methods useful for the practice of the invention can be found, for example, in U.S. Pat. Pub. No. 2006/0173064 (Lippa et al.), U.S. Pat. No. 6,323,236 (McElroy), U.S. Pat. Pub. No. 2007/0275970, PCT application PCT/US/2008/052628 (Johnson et al.) filed Jan. 31, 2008, and PCT application PCT/US/2007/088100 (Johnson and Tiouririne), filed Dec. 19, 2007.

In one embodiment, a composition of the invention may comprise one compound of the invention. In another embodiment, a composition of the invention may comprise more than one compound of the invention. In one embodiment, additional drugs or compounds useful for treating other disorders may be part of the composition. In one embodiment, a composition comprising only one compound of the invention may be administered at the same time as another composition comprising at least one other compound of the invention. In one embodiment, the different compositions may be administered at different times from one another. When a composition of the invention comprises only one compound of the invention, an additional composition comprising at least one additional compound must also be used.

The pharmaceutical compositions useful for practicing the invention may be, for example, administered to deliver a dose of between 1 ng/kg/day and 100 mg/kg/day.

Pharmaceutical compositions that are useful in the methods of the invention may be administered, for example, systemically in oral solid formulations, or as ophthalmic, suppository, aerosol, topical or other similar formulations. In addition to the appropriate compounds, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound, or an analog, modification, or derivative thereof according to the methods of the invention.

Compounds which are identified using any of the methods described herein may be formulated and administered to a subject for treatment of the diseases disclosed herein. One of ordinary skill in the art will recognize that these methods will be useful for other diseases, disorders, and conditions as well.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to provide the active moiety.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

One type of administration encompassed by the methods of the invention is parenteral administration, which includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques Pharmaceutical compositions that are useful in the methods of the invention may be prepared, packaged, or sold in formulations suitable for oral, rectal, vaginal, parenteral, topical, pulmonary, intranasal, inhalation, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject, or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Lactulose can also be used as a freely erodible filler and is useful when the compounds of the invention are prepared in capsule form.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In one aspect, a preparation in the form of a syrup or elixir or for administration in the form of drops may comprise active ingredients together with a sweetener, which is preferably calorie-free, and which may further include methylparaben or propylparaben as antiseptics, a flavoring and a suitable color.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents including naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier.

As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, and intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute about 50% to about 99.9% (w/w) of the composition, and the active ingredient may constitute about 0.1% to about 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to about 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as about 0.1% (w/w) and as much as about 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, comprise about 0.1% to about 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1% to 1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention may be prepared, packaged, or sold in a formulation suitable for intramucosal administration. The present invention provides for intramucosal administration of compounds to allow passage or absorption of the compounds across mucosa. Such type of administration is useful for absorption orally (gingival, sublingual, buccal, etc.), rectally, vaginally, pulmonary, nasally, etc.

In some aspects, sublingual administration has an advantage for active ingredients which in some cases, when given orally, are subject to a substantial first pass metabolism and enzymatic degradation through the liver, resulting in rapid metabolization and a loss of therapeutic activity related to the activity of the liver enzymes that convert the molecule into inactive metabolites, or the activity of which is decreased because of this bioconversion.

In some cases, a sublingual route of administration is capable of producing a rapid onset of action due to the considerable permeability and vascularization of the buccal mucosa. Moreover, sublingual administration can also allow the administration of active ingredients which are not normally absorbed at the level of the stomach mucosa or digestive mucosa after oral administration, or alternatively which are partially or completely degraded in acidic medium after ingestion of, for example, a tablet.

Sublingual tablet preparation techniques known from the prior art are usually prepared by direct compression of a mixture of powders comprising the active ingredient and excipients for compression, such as diluents, binders, disintegrating agents and adjuvants. In an alternative method of preparation, the active ingredient and the compression excipients can be dry- or wet-granulated beforehand. In one aspect, the active ingredient is distributed throughout the mass of the tablet. WO 00/16750 describes a tablet for sublingual use that disintegrates rapidly and comprises an ordered mixture in which the active ingredient is in the form of microparticles which adhere to the surface of water-soluble particles that are substantially greater in size, constituting a support for the active microparticles, the composition also comprising a mucoadhesive agent. WO 00/57858 describes a tablet for sublingual use, comprising an active ingredient combined with an effervescent system intended to promote absorption, and also a pH-modifier.

The compounds of the invention can be prepared in a formulation or pharmaceutical composition appropriate for administration that allows or enhances absorption across mucosa. Mucosal absorption enhancers include, but are not limited to, a bile salt, fatty acid, surfactant, or alcohol. In specific embodiments, the permeation enhancer can be sodium cholate, sodium dodecyl sulphate, sodium deoxycholate, taurodeoxycholate, sodium glycocholate, dimethylsulfoxide or ethanol. In a further embodiment, a compound of the invention can be formulated with a mucosal penetration enhancer to facilitate delivery of the compound. The formulation can also be prepared with pH optimized for solubility, drug stability, and absorption through mucosa such as nasal mucosa, oral mucosa, vaginal mucosa, respiratory, and intestinal mucosa.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compounds include polyol compounds, such as oligo-, di- and monosaccharides such as sucrose, mannitol, lactose, L-arabinose, D-erythrose, D-ribose, D-xylose, D-mannose, D-galactose, lactulose, cellobiose, gentibiose, glycerin, and polyethylene glycol. Other examples of hydrophilic low molecular weight compounds useful as carriers within the invention include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

When a controlled-release pharmaceutical preparation of the present invention further contains a hydrophilic base, many options are available for inclusion. Hydrophilic polymers such as a polyethylene glycol and polyvinyl pyrrolidone, sugar alcohols such as D-sorbitol and xylitol, saccharides such as sucrose, maltose, lactulose, D-fructose, dextran, and glucose, surfactants such as polyoxyethylene-hydrogenated castor oil, polyoxyethylene polyoxypropylene glycol, and polyoxyethylene sorbitan higher fatty acid esters, salts such as sodium chloride and magnesium chloride, organic acids such as citric acid and tartaric acid, amino acids such as glycine, beta-alanine, and lysine hydrochloride, and aminosaccharides such as meglumine are given as examples of the hydrophilic base. Polyethylene glycol, sucrose, and polyvinyl pyrrolidone are preferred and polyethylene glycol are further preferred. One or a combination of two or more hydrophilic bases can be used in the present invention.

The present invention contemplates pulmonary, nasal, or oral administration through an inhaler. In one embodiment, delivery from an inhaler can be a metered dose.

An inhaler is a device for patient self-administration of at least one compound of the invention comprising a spray inhaler (e.g., a nasal, oral, or pulmonary spray inhaler) containing an aerosol spray formulation of at least one compound of the invention and a pharmaceutically acceptable dispersant. In one aspect, the device is metered to disperse an amount of the aerosol formulation by forming a spray that contains a dose of at least one compound of the invention effective to treat a disease or disorder encompassed by the invention. The dispersant may be a surfactant, such as, but not limited to, polyoxyethylene fatty acid esters, polyoxyethylene fatty acid alcohols, and polyoxyethylene sorbitan fatty acid esters. Phospholipid-based surfactants also may be used.

In other embodiments, the aerosol formulation is provided as a dry powder aerosol formulation in which a compound of the invention is present as a finely divided powder. The dry powder formulation can further comprise a bulking agent, such as, but not limited to, lactose, sorbitol, sucrose, and mannitol.

In another specific embodiment, the aerosol formulation is a liquid aerosol formulation further comprising a pharmaceutically acceptable diluent, such as, but not limited to, sterile water, saline, buffered saline and dextrose solution.

In further embodiments, the aerosol formulation further comprises at least one additional compound of the invention in a concentration such that the metered amount of the aerosol formulation dispersed by the device contains a dose of the additional compound in a metered amount that is effective to ameliorate the symptoms of disease or disorder disclosed herein when used in combination with at least a first or second compound of the invention.

Thus, the invention provides a self administration method for outpatient treatment of an addiction related disease or disorder such as an alcohol-related disease or disorder. Such administration may be used in a hospital, in a medical office, or outside a hospital or medical office by non-medical personnel for self administration.

Compounds of the invention will be prepared in a formulation or pharmaceutical composition appropriate for nasal administration. In a further embodiment, the compounds of the invention can be formulated with a mucosal penetration enhancer to facilitate delivery of the drug. The formulation can also be prepared with pH optimized for solubility, drug stability, absorption through nasal mucosa, and other considerations.

Capsules, blisters, and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

For administration by inhalation, the compounds for use according to the methods of the invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the drugs and a suitable powder base such as lactose or starch.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics: antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compounds of the invention which may be administered to an animal, preferably a human, range in amount from about 1.0 μg to about 100 g per kilogram of body weight of the animal. The precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compounds may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising the compounds of the invention and an instructional material that describes administration of the compounds. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression that can be used to communicate the usefulness of the compounds of the invention in the kit for effecting alleviation of the various diseases or disorders recited herein. Optionally, or alternately, the instructional material may describe one or more methods of alleviating the diseases or disorders. The instructional material of the kit of the invention may, for example, be affixed to a container that contains a compound of the invention or be shipped together with a container that contains the compounds. Alternatively, the instructional material may be shipped separately from the container with the intention that the instructional material and the compound be used cooperatively by the recipient.

Relevant nucleic acid and amino sequences encompassed by the present invention include, but are not limited to:

```
Human serotonin transporter (SLC6A4), nucleic acid sequence
(GenBank Accession No. NM_001045-2775 bp mRNA)-
                                                  SEQ ID NO: 1
acagccagcgccgccgggtgcctcgagggcgcgaggccagcccgcctgcccagcccggga ccagcctccccgcgcagcctggcaggtctcctggaggcaaggcgaccttgcttgccctct cttgcagaataacaaggggcttagccacaggagttgctggcaagtggaagaagaacaaa tgagtcaatcccgacgtgtcaatcccgacgatagagagctcggaggtgatccacaaatcc aagcacccagagatcaattgggatccttggcagatggacatcagtgtcatttactaacca gcaggatggagacgacgcccttgaattctcagaagcagctatcagcgtgtgaagatggag aagattgtcaggaaaacggagttctacagaaggttgttcccaccccaggggacaaagtgg agtccgggcaaatatccaatgggtactcagcagttccaagtcctggtgcgggagatgaca cacggcactctatcccagcgaccaccaccacccctagtggctgagcttcatcaagggggaac gggagacctggggcaagaaggtggatttccttctctcagtgattggctatgctgtggacc tgggcaatgtctggcgcttcccctacatatgttaccagaatggagggggggcattcctcc tccctacaccatcatggccattttggggggaatcccgctcttttacatggagctcgcac tgggacagtaccaccgaaatggatgcatttcaatatggaggaaaatctgcccgattttca aagggattggttatgccatctgcatcattgccttttacattgcttcctactacaacacca tcatggcctgggcgctatactacctcatctcctccttcacggaccagctgccctggacca gctgcaagaactcctggaacactggcaactgcaccaattacttctccgaggacaacatca cctggaccctccattccacgtcccctgctgaagaattttacacgcgccacgtcctgcaga tccaccggtctaaggggctccaggacctggggggcatcagctggcagctggccctctgca tcatgctgatcttcactgttatctacttcagcatctggaaaggcgtcaagacctctggca aggtggtgtgggtgacagccaccttcccttatatcatcctttctgtcctgctggtgagg gtgccacccctccctggagcctggaggggtgttctcttctacttgaaacccaattggcaga aactcctggagacaggggtgtggatagatgcagccgctcagatcttcttctctcttggtc cgggctttggggtcctgctggcttttgctagctacaacaagttcaacaacaactgctacc aagatgccctggtgaccagcgtggtgaactgcatgacgagcttcgtttcgggatttgtca tcttcacagtgctcggttacatggctgagatgaggaatgaagatgtgtctgaggtggcca aagacgcaggtcccagcctcctcttcatcacgtatgcagaagcgatagccaacatgccag cgtccactttctttgccatcatcttctttctgatgttaatcacgctgggcttggacagca cgtttgcaggcttggaggggggtgatcacggctgtgctggatgagttcccacacgtctggg ccaagcgccgggagcggttcgtgctcgccgtggtcatcacctgcttctttggatccctgg tcaccctgacttttggaggggcctacgtggtgaagctgctggaggagtatgccacggggc ccgcagtgctcactgtcgcgctgatcgaagcagtcgctgtgtcttggttctatggcatca
```

-continued

```
ctcagttctgcagggacgtgaaggaaatgctcggcttcagcccggggtggttctggagga tctgctgggtggccatcagccctctgtttctcctgttcatcatttgcagttttctgatga gcccgccacaactacgacttttccaatataattatccttactggagtatcatcttgggtt actgcataggaacctcatctttcatttgcatccccacatatatagcttatcggttgatca tcactccagggacatttaaagagcgtattattaaaagtattaccccagaaacaccaacag aaattccttgtggggacatccgcttgaatgctgtgtaacacactcaccgagaggaaaaag gcttctccacaacctcctcctccagttctgatgaggcacgcctgccttctcccctccaag tgaatgagtttccagctaagcctgatgatggaagggccttctccacagggacacagtctg gtgcccagactcaaggcctccagccacttatttccatggattcccctggacatattccca tggtagactgtgacacagctgagctggcctattttggacgtgtgaggatgtggatggagg tgatgaaaaccaccctatcatcagttaggattaggtttagaatcaagtctgtgaaagtct cctgtatcatttcttggtatgatcattggtatctgatatctgtttgcttctaaaggtttc actgttcatgaatacgtaaactgcgtaggagagaacagggatgctatctcgctagccata tattttctgagtagcatatataattttattgctggaatctactagaaccttctaatccat gtgctgctgtggcatcaggaaaggaagatgtaagaagctaaaatgaaaaatagtgtgtcc atgcaaaaaaaaaa
```

Human serotonin transporter (SLC6A4), amino acid sequence (GenBank Accession No. NP_001036; 630 residues)-
SEQ ID NO: 2

```
mettplnsqkqlsacedgedcqengvlqkvvptpgdkvesgqisngysavpspgagddtr hsipattttlvaclhqgeretwgkkvdfllsvigyavdlgnvwrfpyicyqngggafllp ytimaifggiplfymelalgqyhrngcisiwrkicpifkgigyaiciiafyiasyyntim awalyylissftdqlpwtscknswntgnctnyfsednitwtlbstspaecfytrhvlqih rskglqdlggiswqlalcimliftviyfsiwkgvktsgkvvwvtatfpyiilsvllvrga tlpgawrgvlfylkpnwqklletgvwidaaaqiffslgpgfgvllafasynkfnancyqd alvtsvvncmtsfvsgfviftvlgymaemrnedvsevakdagpsllfityaeaianmpas tffaiifflmlitlgldstfaglegvitavldefphvwakrrerfvlavviteffgslvt ltfggayvvklleeyatgpavltvalieavavswfygitqfcrdvkemlgfspgwfwric wvaisplfllfiicsflmsppqlrifqynypywsiilgyeigtssficiptyiayrliit pgtfkeriiksitpetpteipcgdirlnav
```

SNP rs25531 forward primer-
SEQ ID NO: 3
5'-TCCT CCGCTTTGGCGCCTCTTCC-3' (forward)

SNP rs25531 reverse primer-
SEQ ID NO: 4
5'-TGGGGGTTGCAGGGGAGATCCTG-3' (reverse)

rs2891483 forward primer-
SEQ ID NO: 5
GCAGAAGCGATAGCCAACATG rs2891483 reverse primer-
SEQ ID NO: 6
CAAGCCCAGCGTGATTAACATC -continued

```
rs2891483 probe-
                                                   SEQ ID NO: 7
CTTTCTTTGCC[C/A]TCATCT
(represented by CTTTCTTTGCCNTCATCT in the sequence listing)

First primer for amplifying the 5'-HTTLPR 44 bp promoter
region repeat polymorphism-
                                                   SEQ ID NO: 8
5'-CGT TGC CGC TCT GAA TGC CAG-3'

Second primer for amplifying the 5'-HTTLPR 44 bp promoter
region repeat polymorphism-
                                                   SEQ ID NO: 9
5'-GGA TTC TGG TGC CAC CTA GAC GCC-3'

SNP polymorphism site of SLC6A4 rs1042173-
                                                   SEQ ID NO: 10
GCCATATATTTTCTGAGTAGCATATA[G/T]AATTTTATTGCTGGAATCTAC
TAGA-
(represented by
GCCATATATTTTCTGAGTAGCATATANAATTTTATTGCTGGAATCTACTAGA
in the sequence listing)
```

Other methods and techniques useful for the practice of the invention that are not described are known in the art, for example, see International application no. PCT/US2008/064232.

Without further description, it is believed that one of ordinary skill in the art can, using the preceding description and the following illustrative examples, make and utilize the compounds of the present invention and practice the claimed methods. The following working examples, therefore, specifically point out embodiments of the present invention, and are not to be construed as limiting in any way the remainder of the disclosure.

EXAMPLES

Example 1—Correlation of a Functional Polymorphism in the 3'UTR of the Serotonin Transporter Gene SLC6A4 and its Association with Drinking Activity It was determined whether allelic variation at a single nucleotide polymorphism (SNP) within a putative polyadenylation signal for a commonly used 3' polyadenylation site G2651T SNP (National Center for Biotechnology Information reference ID #rs1042173) of SLC6A4, the serotonin transporter gene, is associated with differences in the severity of drinking among treatment-seeking alcoholics. To determine the functional significance of the G2651T/rs1042173 SNP, we examined whether allelic variation at this site was associated with quantifiable changes in mRNA expression level and 5-HTT protein expression. The human serotonin transporter gene (SLC6A4) is found at position 17q11.1-q12 of chromosome 17. G2651T/rs1042173 is in exon 15 position 25,549,137. Additionally, the 5-HTTLPR is in the promoter at chromosome position ~25,588,500. The sequence of the 5'-flanking region of the gene corresponds to GenBank Accession No. X76753 (see Heils et al., J. Neurochem., 66:2621, 1996).

Materials and Methods

Subjects

A total of two hundred seventy-five alcohol-dependent subjects (78.5% male) aged between 18 and 66 years were used in this study, in which 198 of them were included in our previous study (Johnson et al., 2008). All subjects were considered to be alcohol-dependent (see below for details) and enrolled as part of a pharmacotherapy trial for the treatment of alcohol dependence at both the University of Texas Health Science Center at San Antonio and at University of Virginia. Participants were recruited by newspaper or radio advertisements, and written informed consent—approved by review boards of all participating institutes, was obtained from all participants.

Alcohol dependence was diagnosed using the Structured Clinical Interview for Diagnostic and Statistical Manual of Mental Disorders, 4th edition (American Psychiatric Association, 1994) Axis I Disorders, by a trained psychologist. All subjects had a score of ≥8 on the Alcohol Use Disorders Identification Test (AUDIT) (Babor et al., 1992) that screened for individuals with alcohol use and related problems: reported heavy drinking which was defined as drinking of ≥21 standard drinks/week for women and ≥30 standard drinks/week for men during the 90 days prior to enrollment. Absence of other substance use was confirmed by negative urine toxicological screen for narcotics, amphetamines, or sedative hypnotics at enrollment. The Subjects who met the following criteria were excluded from the study: current axis I psychiatric diagnoses other than alcohol or nicotine dependence; significant alcohol withdrawal symptoms based on the revised clinical institute withdrawal assessment for alcohol scale (Sullivan et al., 1989) score >15]; clinically significant physical abnormalities based on physical examination, electrocardiogram recording, hematological assessment, biochemistry including serum bilirubin concentration, and urinalysis; pregnant or lactating state; treatment for alcohol dependence ≤30 days prior to enrollment, and mandated incarceration or employment loss for not receiving alcohol treatment.

Drinking Measurements

Self-reported drinking (measured in standard drinks) in the 90 days prior to study enrollment was quantified using the timeline follow-back method. One standard drink was defined as 0.35 L of beer, 0.15 L of wine, or 0.04 L of 80-proof liquor. The intensity of drinking was assessed by measurement of the mean drinks per drinking day and mean drinks per day. Drinks per drinking day was defined as the total number of drinks divided by the number of drinking days within the 90 days; drinks per day was defined as the total number of drinks divided by 90 days.

DNA Extraction and Genotyping

Ten milliliters of blood was drawn from each subject at baseline to obtain white blood cells for the determination of 5-HTT genotypes. DNA was extracted using a Gentra Puregene® kit (QIAGEN Inc., Valencia, Calif.). SNPs for association analyses were selected using the National Center for Biotechnology Information (NCBI) dbSNP database (http://www.ncbi.nlm.nih.gov/SNP/) based on their functional potential and minor allele frequency (MAF) ≥0.05. The average SNP density is ~7 kb. Detailed information on SNP locations, chromosomal positions, allelic variants, MAF, and primer/probe sequences is summarized in Table 1. Four of the five SNPs (rs6354, rs6355, rs28914832, and rs1042173) were genotyped with TaqMan® SNP genotyping assays (Applied Biosystems, Foster City, Calif.). Polymerase chain reaction (PCR) conditions were 50° C. for 2 min, 95° C. for 10 min, 30 cycles of 95° C. for 25 s, and 60° C. for 1 min. Alleles of each SNP were determined with an ABI PRISM® 7900HT instrument (Applied Biosystems) and analyzed using sequence detection system (SDS) software.

The DNA samples from the 77 subjects that were not included in our previous study were genotyped for 5'-HTTLPR L/S alleles as described previously (Johnson et al., 2008).

Assays for SNP rs25531 were carried out as described by Wendland et al (2006). Each assay had a total assay volume of 20 µl, and the PCR conditions were 15 min at 95° C., 35 cycles of 94° C. for 30 s, 65.5° C. for 90 s, and 72° C. for 60 s, with a final extension step of 10 min at 72° C. Afterwards, 10 µl of PCR product was double-digested with HpaII and BccI (5 U each; New England Biolabs, Ipswich, Mass.) in a 20-µl reaction assay containing NEBuffer 1 and bovine serum albumin at 37° C. for 5 h. Finally, 10 µl of remaining PCR product and 20 µl of restriction enzyme assay solution were electrophoresed with 3.5% UltraPure™ agarose gel (Invitrogen™, Carlsbad, Calif.) for 1.5-2 h at 100 V in Tris/Borate/ethylenediaminetetraacetic acid buffer and visualized by ethidium bromide staining (Sigma-Aldrich, St Louis, Mo.). The uncut PCR product in the lanes loaded with restriction enzyme-digested PCR products were detected as the "A" allele of rs25531, and the cut product at 402 bp were detected as the "G" allele of rs25531.

Association Analyses with Drinking Intensity

Associations of individual SNPs with the intensity of drinking (i.e., drinks per drinking day and drinks per day) were analyzed using the analysis of variance test in SAS version 9.1 (SAS Institute Inc., Cary, N.C.). Three genetic models (additive, dominant, and recessive) were tested using gender and age as covariates. Pair-wise linkage disequilibrium (LD) among all 6 polymorphisms was assessed using the Haploview program (Barrett et al., 2005). All associations found to be significant were corrected for multiple testing according to Bonferroni correction by dividing the significance level by the number of polymorphisms studied.

Cloning, Cell Culture, and Transfection

Allelic expression differences of the SNP (rs1042173) that showed a significant association with drinking intensity were studied using an in vitro system. The human 5-HTT containing the G allele of rs1042173 in pBluescript II KS (−) was a generous gift from Prof. Randy D. Blakely (Vanderbilt University School of Medicine, Nashville, Tenn.). This 5-HTT cDNA/Bluescript construct contained the coding region as well as both 5'- and 3'-untranslated regions of the gene with a total length of 2508 bp. The human 5-HTT construct was digested with HindIII/XbaI and subcloned into pcDNA3.1(−) (Invitrogene™) pre-digested with HindIII/XbaI as described by Qian et al (Qian et al., 1997). To produce plasmid with the T allele of rs1042173, a DNA plasmid carrying the G allele was mutated using the GeneTailor™ site-directed mutagenesis system (Invitrogen™). Both constructs were DNA sequence verified.

HeLa cells were cultured in complete medium [Dulbecco's modified Eagle's medium (HyClone, Logan, Utah), 10% GIBCO® fetal bovine serum (Invitrogen™), 100 U/mi penicillin, and 100 µg/ml streptomycin (Mediatech, Inc., Manassas, Va.)] in 6-well plates and maintained in a humidified incubator at 37° C. and 5% CO2. After the cells reached approximately 80% confluence, they were transfected with one of the two alleles (4 µg of plasmids per well) in 6-well culture plates using Lipofectamine™ 2000 (Invitrogen™) according to the manufacturer's guidelines. RNA and proteins were extracted from HeLa cells 24 h after transfection.

RNA Isolation, Reverse Transcription, and Quantitative Real-Time Polymerase Chain Reaction (qRT-PCR)

Total RNA was extracted from HeLa cells with TRIZOL® reagent (Invitrogen™). Potential DNA contaminations were removed by treating the RNA samples with RNase-free DNase I at 37° C. for 30 min. Each RNA sample was reverse transcribed in vitro using SuperScript®) II RT (Invitrogen™) to obtain cDNA. These cDNA samples were transcribed with TaqMan® Gene Expression Assays (Applied Biosystems) specific for 5-HTT mRNA, and the resulting 5-HTT mRNA was quantified by the ABI PRISM® 7900HT sequence detection system. TaqMan® primer/probe sets for glyceraldehyde-3-phosphate dehydrogenase (G3PDH) were used as an internal control to normalize the expression of 5-HTT. For each qRT-PCR experiment, four samples with the G allele, four samples with the T allele, and four controls with the pcDNA3.1 (−) vector only were used in cell cultures from transfections carried out on different days.

Western Blotting Analysis

Radioimmunoprecipitation assay buffer [Tris-HCl (pH 7.4), 1% NP-40, 150 mM NaCl, 0.25% Na-deoxycholate, and 1 mM EDTA] was added to HeLa cells after washing the cells once with ice-cold phosphate-buffered saline. The protein concentration of the cell lysates was determined using the Bio-Rad assay (Bio-Rad Laboratories, Hercules, Calif.). Fifteen micrograms of samples were loaded onto 10% sodium dodecyl sulfate-polyacrylamide gels (30% acrylamide) in Tris-glycine buffer containing sodium dodecyl sulfate. The separated proteins were then electrophoretically transferred to nitrocellulose membranes (PerkinElmer, Waltham, Mass.) overnight at 25 mA. The membranes were blocked for 1 h at room temperature with 2% non-fat dry milk diluted in Tris-buffered saline with Tween® 20 (TBST) buffer and washed three times for 10 min each in TBST buffer; then they were incubated overnight with primary antibody (1:200) at 4° C. [rabbit polyclonal immunoglobulin G (IgG) corresponding to the C-terminus of a sodium-dependent 5-HTT of human origin (200 µg/ml stock solution) (Santa Cruz Biotechnology, Inc., Santa Cruz, Calif.)]. Membranes then were washed three times for 10 min each in TBST buffer and incubated with secondary antibodies (1:5,000) [anti-rabbit IgG (goat), horseradish peroxidase labeled (PerkinElmer)] for 1.5 h at room temperature. The hybridized membranes were washed with TBST buffer four times for 10 min each, and the immunoreactivity of the proteins was detected using Western Lightning® Chemiluminescence Reagent Plus (PerkinElmer) and exposure to X-ray film. Tubulin protein was used as an internal control to control for discrepancies in the loading of proteins in each lane. A monoclonal antibody (mouse monoclonal antibody to α-tubulin) was used as the primary antibody (1:2,000), and an anti-mouse IgG was used as the secondary antibody in western blotting for tubulin.

Densitometric and Statistical Analysis

Western blotting films were scanned on a UMAX scanner (Techville, Inc., Dallas, Tex.) using Adobe Photoshop (v. 6.0; Adobe Systems Inc., San Jose, Calif.), and the optical densities of the G and T alleles and tubulin were measured using NIH Image software (v. 1.61). The optical densities of bands of the G and T alleles and of tubulin were quantified using densitometry. The background (the area surrounding each band) optical density values were quantified the same way as for the protein bands, and the values were subtracted from the measured optical density values for the protein bands. The ratios of the optical density values of the G and T alleles to the optical density values of tubulin in the corresponding samples were calculated to normalize the expression of the G and T alleles of the 5-HTT. Student's t-test was used to analyze protein data to determine the significance of expression differences between the G and T alleles.

Results

Genotyping and LD Analysis

DNA samples from 275 alcohol-dependent subjects were genotyped in this study. Of these subjects, 165 were Caucasians (43 females and 122 males) and 110 were Hispanics (16 females and 94 males). Genotypic distributions of all 5 SNPs and 5-HTTLPR L/S alleles, conformed to the Hardy-Weinberg equilibrium (Table 1). Further, the LD analyses using Haploview revealed no haplotype blocks among the 5 SNPs and the 5'-HTTLPR L/S polymorphism according to the criteria of Gabriel et al. (2002), in Caucasian, Hispanic or pooled populations, respectively (FIG. 1).

Associations with Self-Reported Drinking Measures

To exclude potential variations caused by ethnic differences on drinking intensity, subgroups of subjects based on ethnicity were analyzed separately for all polymorphisms studied here. Among the polymorphisms analyzed individually using SAS (version 9.1) program for associations with drinking intensity, only SNP rs1042173 in the 3' UTR of SLC6A4 showed a significant association with intensity of drinking. Table 2 shows demographic and drinking parameters of the cohort analyzed for rs1042173 association studies. No significant association was detected for other genetic polymorphisms with intensity of drinking in Caucasian, Hispanic or pooled populations (data not shown).

Among Caucasian subjects, mean drinks per drinking day differed significantly among TT, TG, and GG genotypes (F=5.625; p=0.004). Using Tukey's post-hoc multiple comparison test, the differences between TG heterozygotes and TT homozygotes were statistically significant (d=4.721; p=0.002); however, the differences between TG heterozygotes and GG homozygotes were not (d=2.175; p=0.20). When TT and TG were combined and compared with GG using Student's t-test, the means did not differ significantly (t=0.32; p=0.75). The combined means of TG and GG (FIG. 2A) were significantly lower than the mean of TT (t=2.97; p=0.003). This suggests a dominant effect of the G allele over the T allele. The difference between the means of drinks per drinking day in G-carriers and TT genotypic group was 2.59+0.87 (95% CI—0.879 to 4.297).

Estrogen has been shown to modulate the synthesis, release, and metabolism of 5-HT (Bethea et al., 2002; Frackiewicz et al., 2000; Pivac et al., 2004). Thus, to examine the impact of gender on these associations, we repeated the analyses on male subjects only. In Caucasian males, the mean difference of standard drinks per drinking day between G-carriers and TT genotypic group, was 2.89+ 1.07 (95% CI—0.771 to 5.009), which was similar to the mean difference in combined Caucasian male and female subjects. Therefore, we did not find a significant effect of gender on the associations between rs1042173 genotypes and drinks per drinking day.

However, among Hispanic subjects, we did not detect a significant effect of rs1042173 genotypes on both measures of drinking intensity, drinks per drinking day (F=0.935; p=0.397) and drinks per day (F=0.299; p=0.74).

Considering that 5'-HTTLPR L/S polymorphism has implicated as functional in many reported studies, we examined potential interactive effect of 5'-HTTLPR L/S and rs1042173 alleles on drinking intensity by using a newly developed algorithm for detecting gene-gene interaction, called generalized multifactor dimensionality reduction (GMDR) method (Lou et al. 2007). Our GMDR analyses revealed no significant interaction between these two functional SNPs (P=0.623).

5-HTT mRNA Expression in Cells Transfected with Plasmid Carrying Either T or G Alleles To study whether the T and G alleles of rs1042173 leads to differential expression levels of 5-HTTs, we transfected plasmids carrying the T and G alleles of rs1042173 into HeLa cells and quantified mRNA levels by using the qRT-PCR assay. Results were analyzed for allelic differences using the $\Delta\Delta Ct$ method described by Winer et al (1999). FIG. 3A depicts the mean 5-HTT mRNA expression levels for the T and G alleles from three independent transfection experiments. The G allele yielded significantly higher mRNA expression level compared with the T allele. In the three independent experiments, the G allele-transfected HeLa cells, compared with their T allele-transfected counterparts, always produced a >50% higher 5-HTT mRNA level, an effect that was significant statistically (p<0.0001).

5-HTT Protein Expression in the T and G Alleles of the Rs1042173 SNP

To determine if the allele-associated RNA difference can be translated into protein, we measured allele-specific differences in 5-HTT protein levels between the two alleles. After normalization with tubulin for the loading difference, we found that the 5-HTT protein level with G allele (0.137±0.006) is significantly higher than that of T allele (0.104±0.002) (t=5.53; p=0.005; See FIG. 3B). These results were reproduced in western blotting experiments from several independent replications. Notably, the expression of both mRNA and 5-HTT proteins was in the same direction—the G allele being associated with higher mRNA and protein expression levels than the T allele.

Discussion

The data provide evidence that rs1042173, a SNP in the 3' UTR of the SLC6A4 gene, is associated with intensity of drinking among Caucasians dependent on alcohol. Using a site-directed mutagenesis approach, it was shown that rs1042173 is a functional polymorphism that resulted in a difference in 5-HTT expression levels in HeLa cell cultures, with G allele associated with higher 5-HTT mRNA and protein expression levels than the T allele. Of multiple approaches used to determine whether a polymorphism is a function one, a direct comparison of expression level between two alleles through an in vitro expression system as used in this study represents one of the most convenient molecular techniques in the field.

Alcohol-dependent individuals who were G-allele carriers for rs1042173 showed less intensity of drinking compared with those who were homozygous for the T allele. Importantly, the average intensity of drinking for both of these allelic groups exceeded the threshold for heavy drinking (i.e., 5 and 4 standard drinks/day for men and women, respectively), and all were dependent on alcohol. At the time of entry, subjects in both allelic groups were not statistically significantly different in average chronological age and duration of alcohol dependency. It is, therefore, reasonable to propose that alcohol-dependent individuals with the TT genotype might constitute a subtype of more intense drinkers among heavy-drinking alcoholics of European descent.

This is the first study to investigate the function of the rs1042173 SNP in an alcohol-dependent population. The rs1042173 polymorphism is not only located at a putative polyadenylation signal site in the 3' UTR of the 5-HTT gene but also near a potential binding site for microRNA miRNA-135 according to a bioinformatics prediction with PicTar program (Chen et al., 2006). It has been hypothesized that a variant at this location may change expression levels by affecting the stability of mRNA (Battersby et al., 1999; Beaudoing et al., 2000; Chen et al., 2006). Our findings have been further supported by two recent reports. The first study reported by Vallender et al. (2008) revealed that a functional haplotype containing T allele of rs1042173 was associated with higher mRNA expression in HEK293 cells compared to the haplotype consisting of G allele. Another study reported by Lim et al. (2006) showed that G-allele had increased allelic expression imbalance (AEI) in Epstein-Barr virus transformed lymphoblast cells while human pons tissue showed a decreased AEI for G-allele. Although the expression levels associated with each allele of rs1042173 are inconsistent among these studies (likely due to different reporter genes and/or cell lines used among them), they all reveal that rs1042173 is a functional one.

The finding of no association between rs1042173 genotype and intensity of drinking in Hispanics, which differed from that of an association among Caucasians, while the allelic frequencies for T and G alleles in Caucasians and Hispanics were not significantly different, does suggest the possibility of differential regulation of gene expression by ethnic group. Due to the relatively small sample size of the cohort, such a premise needs to be treated as preliminary and confirmed by larger studies.

The data show that the association between the intensity of drinking and the genotype remained significant in the same manner even if we varied the drinking period prior to enrollment within a range of 14 to 90 days (data not shown). The consistency of these results strengthened our findings.

The findings suggest the possibility that two different subgroups of treatment-seeking alcoholics with allelic differences at the 3' UTR SNP rs1042173 can differ in their intensity of drinking, an effect that might be associated with underlying differences in expression of 5-HTT.

TABLE 1

Biological Information of the 5 SNPs Examined in the Study

| NCBI dbSNP ID | Physical position | Chromosome position | Alleles | CEU[a] | MAF Caucasian[b] | Hispanic[b] |
|---|---|---|---|---|---|---|
| 5-HTTLPR | Promoter | ~25,588,500 | L (long) S (short) | — | 0.451 | 0.430 |
| rs25531 | Promoter | 25,588,472 | A/G | 0.100 | 0.065 | 0.079 |
| rs6354 | Exon 2 (5' UTR) | 25,574,024 | T/G | 0.295 | 0.202 | 0.158 |
| rs6355 | Exon 3 | 25,572,936 | C/G (Ala/Gly) | 0.025 | 0.022 | 0.026 |
| rs28914832 | Exon 10 | 25,562,500 | A/C (Leu/Ile) | 0.008 | 0.003 | 0.009 |
| rs1042173 | Exon 15 (3' UTR) | 25,549,137 | G/T | 0.433 | 0.419 | 0.455 |

| NCBI dbSNP ID | p-values for the deviation from HWE[b] Caucasian | Hispanic | Primers and probe sequences/context sequence ID of ABI primers and probes |
|---|---|---|---|
| 5-HTTLPR | 0.814 | 0.624 | Forward: TCCT CCGCTTTGGCG CCTCTTCC Reverse: TGGGGGTTGCAGGGGA GATCCTG |
| rs25531 | 0.999 | 1.000 | Forward: TCCT CCGCTTTGGCG CCTCTTCC Reverse: TGGGGGTTGCAGGGGA GATCCTG The two alleles were determined using restriction enzymes HpaII and bccI |

TABLE 1-continued

Biological Information of the 5 SNPs Examined in the Study

| | | | |
|---|---|---|---|
| rs6354 | 0.319 | 1.000 | C_1841706_10 |
| rs6355 | 1.000 | 1.000 | C_11414113_20 |
| rs28914832 | 1.000 | 1.000 | [Custom Taqman(R) SNP Genotyping Assay]<br>Forward:<br>GCAGAAGCGATAGCCAACATG<br>Reverse<br>CAAGCCCAGCGTGATTAACATC<br>Probe: CTTTCTTTGCC [C/A]TCATCT |
| rs1042173 | 0.138 | 1.000 | C_7473190_10 |

MAF, minor allele frequency; HWE, Hardy-Weinberg equilibrium; ABI, Applied Biosystems (Foster City, CA).
[a] European sample from HapMap project
[b] Data from this study.

Demographics and Drinking Parameters in the Cohort Analyzed for rs1042173

| | Caucasian | | | | Hispanic | | | |
|---|---|---|---|---|---|---|---|---|
| | TT | TG | GG | p-value | TT | TG | GG | p-value |
| Number of subjects | 47 | 77 | 41 | — | 26 | 56 | 28 | — |
| Gender (% male) | 82.97 | 64.93 | 80.49 | — | 88.46 | 85.71 | 82.14 | — |
| Age (years) | 41.6 ± 1.66 | 42.36 ± 1.23 | 40.98 ± 1.52 | 0.62 | 37.08 ± 2.01 | 40.05 ± 1.22 | 38.82 ± 1.76 | 0.33 |
| Age of onset of problem drinking | 29.74 ± 1.72 | 30.61 ± 1.25 | 28.37 ± 1.87 | 0.69 | 26.44 ± 1.67 | 26.82 ± 1.23 | 26.36 ± 1.87 | 0.91 |
| Baseline drinks per drinking day | 11.17 ± 0.98 | 8.05 ± 0.47 | 9.58 ± 0.67 | 0.0043 | 9.99 ± 0.71 | 10.66 ± 0.67 | 9.76 ± 0.58 | 0.65 |
| Baseline drinks per day | 8.99 ± 0.96 | 6.48 ± 0.44 | 7.72 ± 0.58 | 0.02 | 8.23 ± 0.75 | 7.52 ± 0.59 | 7.92 ± 0.55 | 0.74 |
| Years of lifetime drinking | 11.86 ± 1.32 | 11.75 ± 1.04 | 12.6 ± 1.4 | 0.56 | 10.63 ± 1.68 | 13.23 ± 1.2 | 12.64 ± 1.51 | 0.35 |

Values are means ± SEM. Significant p-values after correction for multiple testing are given in bold. "Years of lifetime drinking" was calculated by subtracting the age at which the subject began experiencing symptoms of alcohol dependence from their age at study enrollment. The adjusted p-value at the 0.05 significance level is 0.010.

BIBLIOGRAPHY FOR EXAMPLE 1

American Psychiatric Association (1994) Diagnostic and statistical manual of mental disorders, 4th ed. American Psychiatric Association, Washington. D.C.
Babor T. F., de la Fuente J. R., Saunders J., Grant M. (1992) AUDIT: The alcohol use disorders identification test, World health organization, Geneva, Switzerland.
Barrett et al., Bioinformatics, 2005, 21:263-265.
Battersby et al., J Neurochem, 1999, 72:1384-1388.
Beaudoing et al., (2000), Genome Res 10:1001-1010.
Bethea et al. (2002), Front Neuroendocrinol 23:41-100.
Bradley et al. (1997), J Neurochem 69:1356-1367.
Cargiulo T. (2007) Am J Health Syst Pharm 64(5 Suppl 3):55-11.
Chen et al. (2006) Hum Genet 120:1-21.
Chen et al. (2006) Nature Genetics 38: 1452-1456
Dundon et al. (2004) Alcohol Clin Exp Res 28(7):1065-73.
Feinn et al., (2005). Am J Med Genet B Neuropsychiatr Genet 133B(1):79-84.
Frackiewicz et al., (2000), Ann Pharmacother 34:80-88.
Gastfriend et al., (2007), J Subst Abuse Treat 33(1):71-80.
Goldman et al. (2005) Nature Reviews Genetics 6:521-532.
Gill K, Amit Z. (1989) Recent Dev Alcohol 7:225-48.
Heils et al. (19%) J Neurochem 66:2621-2624.
Hu et al. (2005) Alcohol Clin Exp Res 29(1): 8-16.
Hu et al. (2006) Am J Hum Genet 78(5):815-26.
Johnson et al. (2004) Alcohol Clin Exp Res 28(2):295-301.
Javors et al. (2005) Prog Neuropsychopharmacol Biol Psychiatry 29(1):7-13.
Johnson et al. (2008) Can serotonin transporter genotype predict serotonergic function, chronicity, and severity of drinking? Prog Neuropsychopharmacol Biol Psychiatry 32(1):209-16.
Kweon Y S, Lee H K, Lee C T, Lee K U, Pae C U. (2005) Association of the serotonin transporter gene polymorphism with Korean male alcoholics. Journal of Psychiatric Research 39:371-376.
LeMarquand et al. (1994) Biol Psychiatry 36:326-337.
Lim et al. (2006) Allelic expression of serotonin transporter (SERT) mRNA in human pons: lack of correlation with the polymorphism SERTLPR. Mol Psychiatry 11(7): 649-662.
Little et al. (1998) Am J Psychiatry 155:207-213.
Lou et al. (2007) Am J Hum Genet 80(6):1125-1137.
Makela P. Mustonen H. (2007) Alcohol Alcohol 42(6):610-7.
Mynett-Johnson et al. (2000) Am J Med Genet 96(6):845-9.
Ozaki et al. (2003) Mol Psychiatry 8(11):933-6.
Pivac et al. (2004) Life Sci 76:521-531.
Prasad et al. (2005) Human scrotonin transporter variants display altered sensitivity to protein kinase G and p38 mitogen-activated protein kinase. PNAS 102(32):11545-11550.
Qian et al. (1997) Protein kinase C activation regulates human serotonin transporters in HEK-293 cells via altered cell surface expression. J Neurosci 17:45-57.

Ramamoorthy et al. (1993) Antidepressant- and cocaine-sensitive human serotonin transporter: molecular cloning, expression, and chromosomal localization. Proc Natl Acad Sci USA 90:2542-2546.

Sullivan et al. (1989) Br J Addict 84:1353-1357.

Talvenheimo et al. (1980). J Biol Chem 255:8606-8611.

Vallender et al. (2008) Functional variation in the 3' untranslated region of the serotonin transporter in human and rhesus macaque. Genes, Brain Behav. 2008 August; 7(6): 690-7

Wendland et al. (2006) Simultaneous genotyping of four functional loci of human SLC6A4, with a reappraisal of 5-HTTLPR and rs25531. Mol Psych. 11:224-226.

Winer et al. (1999) Anal Biochem 270:41-49.

Wrase et al. (2006) Cogn Affect Behav Neurosci 6:53-61.

Example 2—Drinking Histories in Alcohol-Use-Disordered Youth: Relationship of Platelet Serotonin Transporter Expression with Genotypes of the Serotonin Transporter Functional control of the serotonin system is hypothesized to be regulated in part by differences in SERT (5-HTT) expression [15]. The gene responsible for encoding SERT expression has a functional polymorphism at the 5'-regulatory promoter region [16, 17]. The polymorphism contains an insertion/deletion mutation with the long (L) variant having 44 base pairs that are absent in the short (S) variant. In normal controls, the LL genotype, compared to S-carriers (i.e., SS and SL genotypes), has greater 5-HT uptake in human platelets [18], lymphoblasts [19], and greater numbers (e.g., reflecting either greater expression or less turnover) of SERT in human raphe nuclei [20]. Assuming that individuals with the LL genotype have greater SERT expression rates, these individuals would be hypothesized to have greater 5-HT uptake, lower intra-synaptic 5-HT levels, and, therefore, reduced intra-synaptic 5HT neurotransmission in vivo and in vitro [16, 19].

Differential expression of the serotonin transporter, in interaction with chronic alcohol use, may play an important role in the etiology and pathogenesis of alcoholism [15, 21], especially for early-onset alcoholism. For example, adolescents with the LL genotype may have specific vulnerabilities that increase the risk of developing alcoholism [1, 22]. Family risk and population studies provide support for this hypothesis. In a sample of men at risk for alcohol dependence, the LL genotype was more prevalent among those who developed alcohol dependence [23]. Ernouf and colleagues [24] have shown that platelet serotonin (5-HT) uptake was higher in alcohol dependent parents and their children, compared to age-matched controls. Rausch and colleagues [25] showed that adult males with alcohol-dependent fathers had higher mean Vmax for platelet 5-HT uptake, compared to FH-controls. In a Japanese sample, alcoholics with the L allele (e.g., LL and LS genotypes) had a significantly earlier onset of alcohol dependence, compared those with the SS genotype [26]. In a Korean male sample, the frequency of the L-allele was significantly higher in alcohol dependent individuals compared to controls [27]. However, in European and Mexican-American samples, the SS genotype, not the LL genotype, has been associated with an antisocial-type of alcoholism [28, 29], so the genetic risk is clearly not as simple as a single allelic variant increasing risk for alcohol dependence. Our group has reported previously that 5-HT uptake into platelets was greater among EOA males, compared to LOA males and healthy controls [30]. Although in adult normal samples, platelet 5-HT uptake is greater among L-carriers compared to individuals with the SS genotype [18], we recently found that among adults with chronic alcohol dependence, both 5-HT uptake and 3H-paroxetine binding to SERT were reduced among L-carriers (e.g., LL and LS) compared to SS homozygotes [31], and these reductions in platelet 5-HT function were related to years of drinking. Together, the above findings from family risk and population studies support the hypothesis that chronic alcohol use may be "toxic" to SERT and diminish SERT activity expressed in individuals who are L-carriers [15, 20, 22].

The aims were to determine whether SERT genotype (LL vs. S-carriers) differentiated Early Onset adolescents with AUD with respect to their drinking patterns or their serotonergic activity measured by SERT density and function in platelets. Relationships of platelet SERT measures to current and lifetime drinking also were examined. It was hypothesized that platelet measures of SERT binding and function would be related to SERT genotype, in part due to the relatively short histories of alcohol use. Specifically it was predicted that adolescents with AUD would show higher SERT function and SERT density in the LL genotype compared to the S-genotypes (LS, SS). It was also tested whether history of drinking, current amount of drinking, or both, determine how SERT genotype alters SERT function in adolescents with alcohol use disorder.

Materials and Methods

Participants—Participants were youths aged 18-20 with a current alcohol use disorder who were not seeking treatment. Participants were diagnosed with alcohol abuse or alcohol dependence, using criteria from the Diagnostic and Statistical Manual of Mental Disorders, 4th edition (DSM-IV; American Psychiatric Association, 1994). All volunteers were in good physical health (determined by a complete physical examination, electrocardiogram (EKG) within normal limits, and laboratory screening tests within acceptable parameters); were consuming at least 3 Standard Drinks/Drinking Day; had breath-alcohol level of zero at screen; and were literate in English. Exclusionary criteria included current or lifetime Axis I DSM-IV Substance Use Disorder other than to alcohol or cannabis use disorder. Illicit substance use in the past 30 days other than marijuana use was exclusionary. Psychiatric exclusionary criteria included current major depressive disorder, bipolar disorder, post-traumatic stress disorder, psychosis, or attention deficit hyperactivity (ADHD) that was medicated within the previous 30 days. Medical exclusionary criteria included elevated liver enzymes greater than 4 times the normal range, and/or elevated bilirubin (>110% per limits of normal); serious medical co-morbidity requiring medical intervention or close supervision; clinically significant alcohol withdrawal; treatment for alcohol abuse or dependence within the last 30 days; or, if female, pregnant. All participants gave written informed consent. The study was approved by the University of Texas Health Science Center Institutional Review Board.

Diagnostic Measures—Trained therapists used the Children's Interview for Psychiatric Syndromes (ChIPS), which adheres strictly to DSM-IV criteria for psychiatric disorders and has been shown to be accurate and provide valid diagnoses of psychiatric disorders in adolescents and young adults to 20 years of age [32]. Current and lifetime substance use disorders were diagnosed in a structured clinical interview using the Adolescent Diagnostic Interview (ADI) [33, 34]. The principal investigator clarified discrepancies and established reliability of interviews, using the Best Estimate Diagnostic Procedure [35, 36], and monitored for consistency of participant's self-report throughout the study.

Recent reported drinking and lifetime drinking were determined by patient interview using time-line follow back procedures [37].

General design and procedures—The experimental design was a cross-sectional retrospective study. After initial screening, eligible participants gave blood for assay of platelet 5HT function and genotyping. Fifty milliliters of blood was drawn from each participant to obtain platelets for the measurement of 5-HT uptake into intact platelets and paroxetine binding to platelet membranes. Additionally, a 10 ml sample of blood was drawn for the determination of SERT genotype.

Platelet Suspension and Platelet Membrane Preparation—Fifty ml blood was drawn into 60 ml polypropylene syringes containing 10 ml of Acid-Citrate-Dextrose (ACD) buffer. The blood was then centrifuged at 150 g at 23° C. for 20 min in a Beckman TJ-6 centrifuge to obtain platelet-rich plasma (PRP). Platelet count in PRP was determined with a Coulter counter model S-plus VI and adjusted to 3×108 platelets/ml with the addition of platelet buffer (137 mM KCl, 1 mM $MgCl_2$, 5.5 mM glucose, 5 mM HEPES, pH 7.4) to prepare adjusted PRP for the serotonin uptake experiments only. Three ml of adjusted PRP was used for platelet serotonin uptake experiments, which were performed on the day of the blood draw. To prepare platelet membranes for paroxetine binding experiments, the remainder of the PRP was used. One ml of prostaglandin 12 solution (300 ng/ml) per ml of PRP was added to prevent loss of platelets during centrifugation, and then the sample was centrifuged at 550 g. The resulting platelet pellet was resuspended in platelet buffer and then centrifuged at 35,000 g. The platelet membrane pellet was resuspended in 1 ml of platelet buffer and then stored at 80° C. until the day of the assay to measure paroxetine binding.

Serotonin Uptake into Intact Platelets—Platelet 5-HT uptake experiments were performed in 21 participants. The adjusted PRP suspension was used to determine platelet 5-HT uptake. Assay tubes were prepared in duplicate and contained $^3$[H] 5-HT at six different concentrations (62.5 nM to 2000 nM), and 100 μM pargyline with or without 50 μM fluoxetine. These tubes were incubated at 37° C. for 5 min; then the reaction was started by the addition of 100 μl of adjusted PRP that contained 107 platelets. The assay tubes were incubated at 37° C. for an additional 5 min; then the reaction was quenched by rapid filtering through Whatman GF/B filters using a Brandel Cell Harvester. The filters were washed three times with 5 ml of ice-cold wash buffer (50 mM Tris-HCl, 150 mM NaCl, and 20 mM ethylene diamine tetra-acetic acid (EDTA)). Filters were placed in scintillation vials containing 5 ml of Beckman Ready Protein+ scintillation counting fluid and immediately counted. Specific uptake was calculated by subtracting total uptake from nonspecific uptake (fluoxetine tubes). Maximum 5-HT uptake rate (Vmax) in platelets was expressed as fmol 5-HT/min-$10^7$ platelets, and the equilibrium constant (Km) as nM. Km and Vmax were calculated using the one-site hyperbolic function in Prism 4 software by Graph Pad™.

Paroxetine Binding to Platelet Membranes—Platelet membranes were used to determine platelet paroxetine binding. Assay tubes were prepared in duplicate containing incubation buffer (50 mM Tris-HCl, 5 mM KCl and 120 mM NaCl) and $^3$[H] paroxetine at 6 different concentrations (0 to 2 nM) with and without 150 mM fluoxetine. The actual concentration of paroxetine in each tube was determined using a 40 ml aliquot taken from each tube prior to the addition of platelet membranes. The experiment was started by the addition of 80 mg of platelet membrane protein then the assay tubes were incubated for 1 hr at 23° C. The reaction was quenched by addition of ice-cold wash buffer (50 mM Tris HCl, 150 mM NaCl, 20 mM EDTA) and rapid filtering through Whatman GF/B filters treated with 0.3% polyethylenimine using a Brandel Cell Harvester. Filters were washed 3 times with ice-cold wash buffer, dried over-night, placed in scintillation vials containing 5 ml of Beckman Ready Protein+ scintillation counting fluid and counted in a Beckman LS-6500 liquid scintillation counter. Disintegrations per minute (DPM) from the 40 ml aliquots were converted into nM of paroxetine to obtain the actual concentrations in each tube. Total and non-specific binding of paroxetine was plotted against each actual concentration. Specific binding was calculated by subtracting non-specific binding from total binding. Kd and Bmax of paroxetine binding were calculated using Prism4 software (Graphpad). Paroxetine binding (Bmax) was expressed as fmol/mg of platelet membrane protein and Kd as nM. Protein concentrations were measured using the BioRad method and a SPECTRAmax PLUS384 Micro-plate spectrophotometer.

Genotyping—The blood sample for the determination of SERT genotype was drawn at enrollment. White blood cells were separated from plasma and re-suspended, and DNA was isolated using PUREGENE, Gentra systems according to the manufacturer's protocol. The 5'-HTTLPR 44 bp promoter region repeat polymorphism was amplified by polymerase chain reaction (PCR) from ~50 ng of DNA using two primers: 5'-CGT TGC CGC TCT GAA TGC CAG-3' AND 5'-GGA TTC TOG TGC CAC CTA GAC GCC-3' and in a 25-ul final volume consisting of 0.5 U of Tfl DNA polymerase (Epicentre), 1×PCR buffer, 1.5 ml $MgCl_2$, 200 uM dNTPs, 1× enhancer, and 0.6 uM of each primer. The PCR conditions were as follows: 94° for 30 s; 70° C. for 30 s, and 72° C. for 30 s); a final extension of 72° C. for 7 min and terminal hold at 4° C. Separation by gel electrophoresis using 4% MetaPhor agarose (Cambrex, Rockland, Me.) allowed visualization by ethidium bromide/UV detection of the two variants (long (L) and short (S): fragment sizes=464 bp and 420 bp, respectively) of the promoter region of the SCL4A gene (−1415 to −951) [16].

Statistical Analyses—Means and standard deviations for outcome variables of platelet variables (Km and Vmax of 5HT uptake into intact platelets, and Kd and Bmax of paroxetine binding on platelet plasma membranes) were examined. Non-normal distributions of outcome variables were transformed. Planned analyses included Pearson correlations to examine the relationships the platelet variables. T-tests were used to determine whether there were group differences in the LL genotypes vs. S-carrier genotypes, in psychiatric disorders, current, and lifetime drinking, for the dependent variables for platelet 5HT function (Bmax Kd. Vmax, and KM).

Results—The distribution of genotypes was the following: LL, n=8, LS, n=9, SS, n=4. Since S-carriers (LS and SS) were the predominant genotypes in the sample, LS and SS were pooled for the analyses of group differences (e.g., LL vs. S-carriers).

There were no statistically significant differences in age or ethnicity between the LL and S-carriers (see Table 1). However, the LL group had a significantly earlier age of onset and longer duration of alcohol use, but did not have significant differences in quantitative measures of recent drinking. The LL group also had significantly higher inattention and motor components of trait impulsivity, and a trend towards significant differences in total BIS-11 trait impulsivity. All participants had a current Alcohol Use Disorder based on DSM-IV criteria. There were no significant differences between genotype groups in other the DSM-IV psychiatric groups.

Table 2 and FIG. 4 present the results of the platelet studies. Participants having the LL genotype had significantly higher Bmax and Kd than did S-carriers, indicating greater amounts of SERT with lower affinity for paroxetine binding. There were no genotype group differences in the platelet functional measures of 5HT uptake.

Discussion—The main finding was that SERT genotype predicted differences in age of onset and duration of drinking, as well as the platelet binding profile of SERT among adolescent subjects with an alcohol use disorder. Specifically, adolescents with the LL genotype began drinking at a younger age and showed greater 3H-paroxetine binding at lower affinity than did S-carriers.

Even though both groups of participants had an onset of alcohol use disorder during adolescence and were of the same current age (i.e., mean=18.7 yrs), participants with an LL-genotype had significantly earlier age of onset of drinking (i.e., 13.5 vs. 15.2 years of age) compared to the S-carriers. This finding is consistent with a hypothesis described by Johnson [22] predicting that the LL genotype would be associated with an earlier age of onset of problem drinking. Also consistent with the Johnson hypothesis, the LL-group also had higher levels of behavioral vulnerability (i.e., trait impulsivity) than did the S-carriers [1, 15, 22]. This latter finding is interesting in light of the literature suggesting LL-genotypes may have lower 5-HT in the synaptic cleft and lower central turnover of 5-IT associated with higher levels of impulsivity [1, 15, 22]. Interestingly, there were no significant group differences in the current levels of drinking, which contrasts with reports in college students, showing that S-carriers had heavier patterns of binge drinking [38].

Results from previous studies in adult populations have generally shown that the SS genotype is associated with antisocial types of alcoholism in European and Mexican-American populations [28], while among Asian populations, LL-genotype has been associated with alcoholism risk [26, 29]. The present study population of adolescents included Caucasian, "white"—Hispanic, biracial or mixed, and American Indian ancestry participants. The results suggest that the LL genotype may be associated with a greater impulsivity, thereby increasing risk to begin encountering problem drinking at an earlier (adolescent) age. Given the association of the SS-genotype with anxiety and stress-related disorders [15, 39], an alternative hypothesis is that by the time that Caucasian adolescents mature into college-age young adults, other environmental factors such as stress, interact with S-carrier genotypes, to produce anxiety or affective distress resulting in greater patterns of drinking and alcoholism risk.

Previous studies in adults have shown that compared to S-carriers, the LL-genotype is associated with increased central SERT binding [20] and increased 5-HT uptake (but not binding) in the platelets of healthy subjects [18]. However, this finding appears not to be the case in adult alcoholics. It is known that adult alcoholics having an L-allele actually have reduced 3H-paroxetine binding and 5-HT uptake into platelets compared to the SS-homozygotes—and hypothesized that this effect is related to years of problem drinking [31]. The current findings suggest that adolescent problem drinkers who have the LL genotype initially have normal patterns of increased SERT binding, but that S-carriers do not have normal SERT binding. Therefore, it is reasonable to speculate that with continued heavy drinking, adolescents who have earlier onset of drinking and longer duration of drinking have an earlier onset of down regulation of SERT than is seen in adult alcoholics.

| | Genotype | | | | |
|---|---|---|---|---|---|
| Variable | LL (n = 8) | | LS/SS (n = 13) | | P value |
| | Mean | (SD) | Mean | (SD) | |
| Age (yrs) | 18.9 | 0.6 | 18.5 | 0.5 | 0.20 |
| Trait Impulsivity (BIS-11) | | | | | |
| Non-planning | 26.0 | 4.7 | 24.4 | 6.9 | 0.57 |
| Inattention | 20.5 | 3.4 | 16.5 | 3.8 | 0.03 |
| Motor | 27.8 | 3.2 | 23.9 | 3.2 | 0.02 |
| Total Lifetime Drinking | 74.3 | 7.4 | 64.9 | 11.3 | 0.05 |
| Age of Onset of Alcohol Use (yrs) | 13.5 | 1.2 | 15.2 | 1.9 | 0.03 |
| Duration of Alcohol Use (yrs) | 5.4 | 0.9 | 3.3 | 1.8 | <0.01* |
| Recent Drinking | | | | | |
| DD | 3.0 | 1.7 | 3.9 | 5.3 | 0.98 |
| DDD | 9.9 | 5.7 | 7.8 | 7.8 | 0.27 |
| PDA | 67.6 | 16.1 | 52.7 | 25.7 | 0.16 |

| | Number | (Percent of LL Participants) | Number | (Percent of LS/SS Participants) | |
|---|---|---|---|---|---|
| Gender | | | | | |
| Male | 5 | 62.5 | 8 | 61.5 | 0.97 |
| Female | 3 | 37.5 | 5 | 38.5 | |

-continued

| Variable | Genotype | | | | P value |
|---|---|---|---|---|---|
| | LL (n = 8) | | LS/SS (n = 13) | | |
| Ethnicity | | | | | |
| Caucasian | 2 | 25.0 | 3 | 23.1 | 0.38 |
| Hispanic | 3 | 37.5 | 9 | 69.2 | |
| Biracial or Mixed | 3 | 37.5 | 0 | 0.0 | |
| American Indian | 0 | 0.0 | 1 | 7.7 | |
| ADHD | 3 | 37.5 | 3 | 25.0 | 0.48 |
| ODD | 1 | 12.5 | 3 | 25.0 | 0.55 |
| CD | 6 | 75.0 | 9 | 75.0 | 0.92 |
| Mood Disorders | 2 | 25.0 | 3 | 23.0 | 0.85 |
| Anxiety Disorders | 0 | 0.0 | 4 | 44.0 | 0.81 |
| Alcohol Use Disorder | 8 | 100.0 | 13 | 100.0 | + |
| Alcohol Dependence | 8 | 100.0 | 10 | 83.3 | 0.14 |
| Alcohol Abuse | 0 | 0.0 | 3 | 16.7 | ** |
| Cannabis Dependence | 1 | 12.5 | 6 | 50.0 | 0.11 |

*Duration of alcohol use remains significant after including Barrett Impulsivity Scale (BIS) total as covariate. DD: Average Drinks per Day in past 90 days; DDD: Average Drinks per Drinking Day in past 90 days; PDA: Percent Days Abinsent in past 90 days; (+) All participants met criteria for a current Alcohol Use Disorder; **Three participants met DSM-IV-TR criteria for Alcohol Abuse. Attention Deficit Hyperactivity Disorder (ADHD); Oppositional Defiant Disorder (ODD), Conduct Disorder (CD)

Example 2, Table 2

Group Differences in Measures of 5HT Uptake and Paroxetine Binding

| Variable | Genotype | | | | P value |
|---|---|---|---|---|---|
| | LL (n = 8) | | LS/SS (n = 13) | | |
| | Mean | (SD) | Mean | (SD) | |
| Paroxetine Binding | | | | | |
| $B_{max}$ (fmol/mg protein) | 802.0 | 254.2 | 504.3 | 199.8 | 0.02 |
| $K_d$ (nM) | 0.7 | 0.5 | 0.4 | .3 | 0.03 |
| Bmax/Kd | 1293.2 | 508.6 | 1861.4 | 1318.0 | 0.18 |
| 5HT Uptake | | | | | |
| Vmax (fmol/min-$10^7$ platelets) | 181.6 | 128.4 | 200.1 | 113.5 | 0.46 |
| $K_m$ (µM) | 445.9 | 409.3 | 323.2 | 136.4 | 0.40 |
| $V_{max}/K_m$ | 0.6 | 0.4 | 0.7 | 0.4 | 0.53 |

Note:
Data were transformed to the natural log scale for t-test analyses.

Conclusion—The present findings provide partial support for the hypothesis that among currently drinking adolescents with an alcohol use disorder, those having an LL-genotype display greater impulsivity, began drinking at an earlier age, and have increased $^3$H-paroxetine binding to platelet SERT. These findings expand our current understanding of the Y-promoter of the SERT gene in regulating the SERT in adolescents with AUD. This study provides preliminary findings that further demonstrate that platelet and genetic measures of SERT function may be useful measures to track the complex interplay of biological and environmental factors in the etiology of vulnerability and risk of either alcoholism onset or toxicity.

EXAMPLE 2 BIBLIOGRAPHY

1. Johnson, B. A. and N. Ait-Daoud, Psychopharmacology, 2000. 149: p. 327-344.
2. LeMarquand et al., Biological Psychiatry, 1994. 36: p. 326-337.
3. LeMarquand et al., American Journal of Psychiatry, 1999. 156: p. 1771-1779.
4. Stoltenberg, S. F., Alcoholism: Clin. Exp. Res., 2003. 27: p. 1853-1859.
5. Linnoila ct al., Life Sciences, 1983. 33: p. 2609-2614.
6. Fils-Aimc, M. L., et al., Archives of General Psychiatry, 1996. 53(3): p. 211-216.
7. Cloninger, C., Science, 1987. 236: p. 410-416.
8. Virkkunen et al., Archives of General Psychiatry, 1987. 44: p. 241-247.
9. Virkkunen et al., Archives of General Psychiatry, 1996. 53: p. 523-529.
10. Swann et al., Psychopharmacology, 1999. 143: p. 380-384.
11. Grunbaum, J. A., et al., Morb. Mort. Wkly Rpt., Surveil. Sum. 2002.51(4): p. 1-62.
12. McBride, et al., Critical Reviews in Neurobiology, 1998. 12: p. 339-369.
13 Virkkunen, et al., Journal of Psychiatry and Neuroscience, 1995. 20: p. 271-275.
14. Virkkunen, et al., Epidemiology, Neurobiology, Psychology, Family Issues., M. Galanter, Editor. 1997, Plenum Press: New York. p. 173-189.
15. Heinz et al., Psychopharmacology, 2004. 174: p. 561-570.
16. Heil et al., Journal of Neurochemistry, 1996. 66: p. 2621-2624.
17. Heils et al., Journal of Neural Transmission, 1997. 104: p. 1005-1014.
18. Greenberg et al., American Journal of Medical Genetics, 1999. 88: p. 83-87.
19. Lesch, et al., Science, 1996. 274: p. 1527-1531.
20. Heinz, et al., Biological Psychiatry, 2000. 47: p. 643-649.

21. Meltzer, et al., Psychiatry Research, 1998. 24: p. 263-269.
22. Johnson, B. A., et al., Alcoholism: Clin. Exp. Res., 2000. 24(10): p. 1597-1601.
23. Schuckit, et al., Biological Psychiatry, 1999. 45: p. 647-651.
24. Ernouf, et al., Life Sciences, 1993. 52: p. 989-995.
25. Rausch, J. L., et al., Neuropsychopharmacology, 1991. 4(2): p. 83-6.
26. Ishiguro, et al., Alcoholism: Clin. Exp. Res., 1999. 23: p. 1281-1284.
27. Kweon, et al., Journal of Psychiatric Research, 2005. 39: p. 371-376.
28. Feinn, et al., American Journal of Medical Genetics Part B (Neuropsychiatric Genetics), 2005. 133B: p. 79-84.
29. Konishi, et al., Alcohol, 2004. 32: p. 45-52.
30. Javors, et al., Alcohol and Alcoholism, 2000. 35: p. 390-393.
31. Johnson, et al., Neuropsychopharmacology and Biological Psychiatry, in press.
32. Rooney, et al., Administration manual of the ChIPS. 1999. Washington, D.C.: American Psychiatry Press.
33. Winters, et al., Adoles. Diagnostic Interview Schedule and Manual. 1993, Los Angeles: Western Psychological Services.
34. Winters, K. C., et al., Psychology of Addictive Disorders, 1993. 7: p. 185-196.
35. Leckman et al., Archives of General Psychiatry, 1982. 39: p. 879-883.
36. Kosten, et al., American Journal of Psychiatry, 1992. 149: p. 1225-1227.
37. Sobell. L. C., Sobell, M. B., Timeline follow-back: A technique for assessing self-reported alcohol consumption., in Measuring Alcohol Consumption: Psychosocial and biochemical methods, E. R. Litten. Allen, J., Editor. 1992, Humana Press Inc.: Totwa, N.J. p. 41-72.
38. Covault et al., Biological Psychiatry, 2007. 61(5): p. 609-16.
39. Lesch, K. P., European Journal of Pharmacology, 2005. 526: p. 113-124.
40. Dawes, et al., Alcohol and Alcoholism, 2004. 39(3): p. 166-177.
41. Pine, et al., Archives of General Psychiatry, 1997. 54: p. 839-846.
42. Soloff et al., Alcoholism: Clin. Exp. Res., 2000. 24(11): p. 1609-1619.
43. Twitchell et al., Alcoholism: Clin. Exp. Res., 2000. 24(7): p. 972-979.
44. Twitchell, et al., Alcoholism: Clin. Exp. Res., 2001. 25(7): p. 953-959.

Example 3—LL Alcoholics Experience Greatest Reduction in Drinking Severity Following Ondansetron Treatment 5-HT3 up-regulation increases the function of DA (Blandina et al 1989; Blandina et al 1988; De Deurwaerdere et al 1998), the principal neurotransmitter mediating alcohol's rewarding effects. This up-regulation may be increased by bouts of binge drinking because the extent to which the 5-HT3 receptor is potentiated is inversely related to the level of basal 5-HT neurotransmission (Lovinger 1991; Lovinger 1999; Lovinger and Zhou 1994; Lovinger and Zhou 1998; Zhou and Lovinger 1996; Zhou et al 1998). Ondansetron may, therefore, be differentially effective in EOA with presumed LL variant predominance by blockade of up-regulated 5-HT3 receptors, thereby ameliorating the serotonergic dysfunction and decreasing alcohol's rewarding effects.

Polymorphic variation of the SERT at 5'-HTTLPR also may explain the therapeutic treatment response to SSRIs among type A alcoholics (similar to LOA) with presumed SS/SL predominance (Pettinati et al 2000). This association is, however, probably not mediated through 5-HT3 mechanisms. It is proposed herein that in Pettinati et al.'s type A alcoholics, predominantly with the SS/SL form, basal serotonergic function was normal. Chronic SSRI treatment, therefore, produced modest facilitation of 5-HT neurotransmission and long-term inhibition of dopaminergic activity, thereby offsetting alcohol's rewarding effects during chronic drinking. Individuals with the SS/SL form of 5'-HTTLPR can be expected to experience a similar modest anti-rewarding effect during acute alcohol intake while receiving chronic SSRI treatment. In contrast, chronic SSRI treatment was probably ineffective at reducing the protracted drinking of type B alcoholics (Kranzler et al 1996) with presumed LL predominance because serotonergic activity would have been increased greatly (as there are relatively fewer SERT transporters in this state), and the ensuing marked hypo-dopaminergic state probably triggered relief drinking to normalize this neurochemical condition. Chronic SSRI treatment probably has little effect on 5-HT neurotransmission among acutely drinking individuals with the LL variant because basal serotonin reuptake already is enhanced greatly.

The present studies were performed to determine if the effective of ondansetron treatment could be correlated with the expression of the LL variant of 5'-HTTLPR and alcohol consumption.

Materials and Methods

In a pre-planned interim analysis, data were examined for the 226 alcohol-dependent individuals (aged 18-65 years) enrolled into the 12-week randomized controlled pharmacotherapy trial to determine the effect of ondansetron on drinking among individuals who varied on allelic difference at the 5-HTT gene and age of alcoholism onset. All these individuals were enrolled at the University of Texas Health Science Center at San Antonio. Briefly, the study design was 2 (LL vs. LS/SS)×2 (early onset vs. late onset)×2 (ondansetron 4 µg/kg b.i.d. vs. placebo). The inferential results below are for the severity of drinking-drinks/drinking day (DDD).

Demographic data were that: 74% were male and 26% female; 48% were early-onset alcoholics and 52% late-onset alcoholics, and 20% were Hispanic and 80% White. There were no significant differences (P>0.05) on demographics between the treatment groups. Baseline mean (SD) DDD (past 90 days) were also similar for the ondansetron 4 µg/kg b.i.d. and placebo groups—9.83 (4.63) vs. 9.85 (4.49), respectively. The inferential analyses were conducted on all randomized subjects according to the intent-to-treat principle. The analytic plan was first to calculate the DDD in each week. We then used the difference between weekly DDD and the baseline DDD (in the past 90 days) as repeat measures. A mixed-model approach (SAS PROC MIXED) was used to study the effect of treatment, genotype (LL vs. LS/SS), treatment and genotype interaction, age, age of onset (early vs. late), gender, and age at onset of problem drinking, adjusting for the baseline DDD level. Also included is a random slope for time to study the variation in the time trend of the weekly DDD.

Results—Example 3

It was observed that DDD for both the ondansetron and placebo groups had a roughly linear decreasing time pattern; thus, all groups improved their drinking outcomes over time (F=32.96; P<0.0001). The table below (Table 1—Example 3) shows the cell contrasts for the different genotypes on DDD for the placebo and treatment (i.e., ondansetron) groups.

There also was a main effect of treatment (F=5.64; P=0.02). The interaction of treatment and genotype was highly significant (F=6.99; P=0.0083). There also was a marginally significant effect of age of onset (F=3.68; P=0.06). There was an overall significant effect for the LL group to reduce DDD (F=5.64; P=0.02) and an effect of time (F=12.69; P=0.0007). From the table, the cell contrasts show that the reduction in DDD for the LL group was driven by the fact that the ondansetron LL group had a significantly greater reduction in DDD compared with the other allelic types. Indeed, the effect size (Cohen's d) for ondansetron's effect in LL individuals to reduce DDD was large (i.e., 0.08). The mean (SEM) DDD reduction from baseline across the treatment period for the different genotypes and treatment conditions was 5.70 (0.64) for ondansetron LL, 3.45 (0.44) for ondansetron LS/SS, 3.54 (0.67) for placebo LL, and 4.25 (0.45) for placebo LS/SS. About 70% of those who entered the double-blind phase completed the trial.

These promising data provide the first evidence that alcoholics with the LL genotype, compared with their LS/SS counterparts, experience significantly greater reduction in the severity of drinking following ondansetron treatment.

TABLE 1

Example 3

| Treatment | Genotype | Estimate | Lower CI | Upper CI | P-Value | Cohen's d |
|---|---|---|---|---|---|---|
| Placebo | LS/SS vs. LL | -0.71 | -2.29 | 0.87 | 0.379 | 0.03 |
| Treatment | LS/SS vs. LL | 2.25 | 0.73 | 3.78 | 0.004 | 0.10 |
| Placebo vs. treatment | LS/SS | -0.80 | -2.03 | 0.43 | 0.203 | 0.04 |
| Placebo vs. treatment | LL | 2.16 | 0.35 | 3.98 | 0.020 | 0.08 |

Critically, these new findings on serotonergic medications revive the concept that alcoholism is a heterogeneous disorder associated with varying neurochemical abnormalities. Medications that specifically target one or more of these underlying abnormalities promise, therefore, to be powerful treatments, and their trials should advance our scientific understanding of the disease.

Example 4—Methods of Predicting Responses to Treatment Based on Different Genotypes of the 5'-HTTLPR and the 3'-UTR of the Serotonin Transporter Gene SLC6A4 and Methods of Treatment Based on the Differences Based on the results of the experiments described in Examples 1-3, a series of studies were performed to determine whether there is a pharmacogenetic effect of ondansetron to differentially treat those with the LL genotype of the 5'-HTTLPR, the TT genotype of the 3'-UTR of rs1042173, or the combination of the genotypes.

Materials and Methods

Subjects: 289 alcohol-dependent men and women enrolled in a 12-week treatment trial in which they received either ondansetron (4 µg/kg) or placebo. All subjects also received weekly cognitive behavioral therapy as their standardized psychosocial treatment. Genotyping was conducted on all subjects.

Statistical Methods: Mixed-effects models were used to study the effect of treatment and genotype and their interaction for each of the primary drinking outcomes. The models included random intercept and random slope and were adjusted for covariates such as participants' average 90-day drinking levels prior to the study, age, gender, ethnicity (Caucasian and Hispanic), and center. A variance-components covariance matrix was used to model different variances for the intercept and slope and a covariance between them. Interactions of treatment, genotype, age, and center were first included in the models. They were excluded from the final models if not significant.

Results: For drinks per drinking day (DDD) outcome, it was found that there were significant rs1042173 main effects in DDD (p=0.003) as well as in the rs1042173-by-5'-HTTLPR L/S alleles (LL, LS/SS) interaction effect (p=0.021) and the 5'-HTTLPR LS alleles-by-treatment interaction effect (p=0.028). Patients with the TT genotype had more than a 1-DDD reduction compared with those with TG/GG (mean difference=-1.16; 95% CI: -1.93 to -0.39; p=0.003). Unexpectedly, in patients with both the LL and TT genotypes (LT), the DDD reduction was much greater than in those with the other genotype combinations of rs1042173 and 5'-HTTLPR L/S alleles (p<0.05), and there was more than a 2-DDD reduction in LT individuals compared with those who had LL, and TG/GG (LG; mean difference=-2.06; 95% CI: -3.27 to -0.85; p=0.001). When treated with ondansetron, TT genotype patients seemed to respond to treatment more effectively than did TG/GG genotype patients (mean difference=-1.31; 95% CI: -2.36 to -0.25; p=0.016). A similar treatment effect was observed when we compared patients with the LL genotype with those who had LS/SS (mean difference=-1.41; 95% CI: -2.46 to -0.36; p=0.009), and among patients with the LL genotype, those in the treatment group had a 1.5-DDD reduction compared with those in the placebo group (mean difference=-1.50; 95% CI: -2.70 to -0.31; p=0.013). Similar effects were observed for other drinking measures.

Conclusion: Ondansetron exerts a preferential treatment effect to reduce severe drinking among alcohol-dependent individuals with the LL, genotype of the 5'-HTTLPR, an effect that is increased among those who also possess the TT allele in the 3'-UTR of rs1042173. These data demonstrate an important pharmacogenetic effect of ondansetron in alcohol-dependent individuals. This study validates a method whereby alcohol-dependent individuals identified as having either of these alleles, or their combination, can be treated effectively with ondansetron.

The data presented in Examples 1 and 4 demonstrate that there is an association with higher severe drinking and susceptibility to ondansetron treatment in alcohol-dependent subjects homozygous for T, relative to alcohol-dependent subjects with a G allele.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A method of treating a patient having one or both of genotypes (a) and (b) and an addictive disease or disorder, comprising:
   (i) performing, on a biological sample from the patient having an addictive disease or disorder, a genetic diagnostic assay to detect the presence of one or both of genotypes (a) and (b) in the patient, wherein genotype (a) is the LL genotype of the functional polymorphism serotonin transporter-linked polymorphic region 5-HTTLPR of gene SLC6A4; and genotype (b) is the TT genotype of rs1042173 of gene SLC6A4; and
   (ii) administering a therapeutically effective amount of ondansetron to the patient having one or both of genotypes (a) and (b); wherein the addictive disease or disorder is an alcohol-related disease or disorder or an opioid-related disorder.

2. The method of claim 1, wherein the patient is determined to have genotype set (a).

3. The method of claim 1, wherein the patient is determined to have genotype set (b).

4. The method of claim 1, wherein the patient is determined to have genotype sets (a) and (b).

5. The method of claim 1, wherein ondansetron is administered at a dosage ranging from 0.1 µg/kg to 10 µg/kg per application.

6. The method of claim 1, wherein the ondansetron is administered at a dosage ranging from about 1.0 µg/kg per application to about 5.0 µg/kg per application.

7. The method of claim 1, wherein ondansetron is administered at a dosage of about 3.0 µg/kg per application.

8. The method of claim 1, wherein ondansetron is administered at a dosage of about 4.0 µg/kg per application.

9. The method of claim 1, wherein ondansetron is administered at least once a day.

10. The method of claim 1, wherein ondansetron is administered at least twice a day.

11. The method of claim 1, wherein the addictive disease or disorder is an alcohol-related disease or disorder.

12. The method of claim 11, wherein the alcohol-related disease or disorder is selected from early-onset alcoholism, late-onset alcoholism, alcohol-induced psychotic disorder with delusions, alcohol abuse, excessive drinking, heavy drinking, problem drinking, alcohol intoxication, alcohol withdrawal, alcohol intoxication delirium, alcohol withdrawal delirium, alcohol-induced persisting dementia, alcohol-induced persisting amnestic disorder, alcohol dependence, alcohol-induced psychotic disorder with hallucinations, alcohol-induced mood disorder, alcohol-induced or associated bipolar disorder, alcohol-induced or associated posttraumatic stress disorder, alcohol-induced anxiety disorder, alcohol-induced sexual dysfunction, alcohol-induced sleep disorder, alcohol-induced or associated gambling disorder, alcohol-induced or associated sexual disorder, alcohol intoxication, and alcohol withdrawal.

13. The method of claim 11, wherein the alcohol-related disease or disorder is early onset alcoholism.

14. The method of claim 11, wherein the alcohol-related disease or disorder is late onset alcoholism.

15. The method of claim 11, wherein the alcohol-related disease or disorder is alcohol dependence.

16. The method of claim 1, wherein the addictive disease or disorder is an opioid-related disorder.

17. The method of claim 16, wherein the opioid-related disorder is selected from the group consisting of: opioid dependence, opioid abuse, opioid intoxication, opioid intoxication delirium, opioid-induced psychotic disorder, with delusions, opioid-induced psychotic disorder with hallucinations, opioid-induced anxiety disorder, opioid-related disorder not otherwise specified (nos), opioid intoxication, and opioid withdrawal.

18. The method of claim 16, wherein the opioid-related disorder is opioid dependence.

19. The method of claim 1, wherein the opioid-related disorder is opioid abuse.

* * * * *

SEQUENCE LISTING

<160> NUMBER OF SEQ ID NOS: 19

<210> SEQ ID NO 1
<211> LENGTH: 2775
<212> TYPE: DNA
<213> ORGANISM: Homo sapiens

<400> SEQUENCE: 1

```
acagccagcg ccgccgggtg cctcgagggc gcgaggccag cccgcctgcc cagcccggga      60
ccagcctccc cgcgcagcct ggcaggtctc ctggaggcaa ggcgaccttg cttgccctct     120
cttgcagaat aacaaggggc ttagccacag gagttgctgg caagtggaaa gaagaacaaa     180
tgagtcaatc ccgacgtgtc aatcccgacg atagagagct cggaggtgat ccacaaatcc     240
aagcacccag agatcaattg ggatccttgg cagatggaca tcagtgtcat ttactaacca     300
gcaggatgga gacgacgccc ttgaattctc agaagcagct atcagcgtgt gaagatggag     360
aagattgtca ggaaaacgga gttctacaga aggttgttcc caccccaggg gacaaagtgg     420
agtccgggca aatatccaat gggtactcag cagttccaag tcctggtgcg ggagatgaca     480
cacggcactc tatcccagcg accaccacca ccctagtggc tgagcttcat caaggggaac     540
gggagacctg gggcaagaag gtggatttcc ttctctcagt gattggctat gctgtggacc     600
tgggcaatgt ctggcgcttc ccctacatat gttaccagaa tggaggggg gcattcctcc      660 tcccctacac catcatggcc attttttgggg gaatcccgct cttttacatg gagctcgcac     720
tgggacagta ccaccgaaat ggatgcattt caatatggag gaaaatctgc ccgattttca     780
aagggattgg ttatgccatc tgcatcattg ccttttacat tgcttcctac tacaacacca     840
tcatggcctg ggcgctatac tacctcatct cctccttcac ggaccagctg ccctggacca     900
gctgcaagaa ctcctggaac actggcaact gcaccaatta cttctccgag gacaacatca     960
cctggaccct ccattccacg tccctgctg aagaattta cacgcgccac gtcctgcaga    1020
tccaccggtc taagggcctc caggacctgg ggggcatcag ctggcagctg gccctctgca    1080
tcatgctgat cttcactgtt atctacttca gcatctggaa aggcgtcaag acctctggca    1140
aggtggtgtg ggtgacagcc accttccctt atatcatcct ttctgtcctg ctggtgaggg    1200
gtgccaccct ccctggagcc tggagggtg ttctcttcta cttgaaaccc aattggcaga    1260
aactcctgga gacaggggtg tggatagatg cagccgctca gatcttcttc tctcttggtc    1320
cgggctttgg ggtcctgctg gcttttgcta gctacaacaa gttcaacaac aactgctacc    1380
aagatgccct ggtgaccagc gtggtgaact gcatgacgag cttcgtttcg ggattgtca    1440 tcttcacagt gctcggttac atggctgaga tgaggaatga agatgtgtct gaggtggcca    1500
aagacgcagg tcccagcctc ctcttcatca cgtatgcaga agcgatagcc aacatgccag    1560
cgtccacttt ctttgccatc atcttctttc tgatgttaat cacgctgggc ttggacagca    1620
cgtttgcagg cttggagggg gtgatcacgg ctgtgctgga tgagttccca cacgtctggg    1680
ccaagcgccg ggagcggttc gtgctcgccg tggtcatcac ctgcttcttt ggatccctgg    1740
tcaccctgac ttttggaggg gcctacgtgg tgaagctgct ggaggagtat gccacggggc    1800
ccgcagtgct cactgtcgcg ctgatcgaag cagtcgctgt gtcttggttc tatggcatca    1860
```

```
ctcagttctg cagggacgtg aaggaaatgc tcggcttcag cccggggtgg ttctggagga    1920
tctgctgggt ggccatcagc cctctgtttc tcctgttcat catttgcagt tttctgatga    1980
gcccgccaca actacgactt ttccaatata attatcctta ctggagtatc atcttgggtt    2040
actgcatagg aacctcatct ttcatttgca tccccacata tatagcttat cggttgatca    2100
tcactccagg gacatttaaa gagcgtatta ttaaaagtat taccccagaa acaccaacag    2160
aaattccttg tggggacatc cgcttgaatg ctgtgtaaca cactcaccga gaggaaaaag    2220
gcttctccac aacctcctcc tccagttctg atgaggcacg cctgccttct ccctccaag     2280 tgaatgagtt tccagctaag cctgatgatg aagggccctt ctccacaggg acacagtctg    2340
gtgcccagac tcaaggcctc cagccactta tttccatgga ttccctgga catattccca     2400 tggtagactg tgacacagct gagctggcct attttggacg tgtgaggatg tggatggagg    2460
tgatgaaaac caccctatca tcagttagga ttaggtttag aatcaagtct gtgaaagtct    2520
cctgtatcat ttcttggtat gatcattggt atctgtatatc tgtttgcttc taaaggtttc   2580
actgttcatg aatacgtaaa ctgcgtagga gagaacaggg atgctatctc gctagccata    2640
tattttctga gtagcatata taattttatt gctggaatct actagaacct tctaatccat    2700
gtgctgctgt ggcatcagga aaggaagatg taagaagcta aatgaaaaa tagtgtgtcc     2760 atgcaaaaaa aaaaa                                                     2775
```

<210> SEQ ID NO 2
<211> LENGTH: 630
<212> TYPE: PRT
<213> ORGANISM: Homo sapiens

<400> SEQUENCE: 2

```
Met Glu Thr Thr Pro Leu Asn Ser Gln Lys Gln Leu Ser Ala Cys Glu
1               5                   10                  15

Asp Gly Glu Asp Cys Gln Glu Asn Gly Val Leu Gln Lys Val Val Pro
            20                  25                  30

Thr Pro Gly Asp Lys Val Glu Ser Gly Gln Ile Ser Asn Gly Tyr Ser
        35                  40                  45

Ala Val Pro Ser Pro Gly Ala Gly Asp Asp Thr Arg His Ser Ile Pro
    50                  55                  60

Ala Thr Thr Thr Thr Leu Val Ala Glu Leu His Gln Gly Glu Arg Glu
65                  70                  75                  80

Thr Trp Gly Lys Lys Val Asp Phe Leu Leu Ser Val Ile Gly Tyr Ala
                85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
    130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205
```

```
Cys Thr Asn Tyr Phe Ser Glu Asp Asn Ile Thr Trp Thr Leu His Ser
    210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
                260                 265                 270

Gly Val Lys Thr Ser Gly Lys Val Trp Val Thr Ala Thr Phe Pro
                275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Gln Ile Phe Phe Ser
                325                 330                 335

Leu Gly Pro Gly Phe Gly Val Leu Leu Ala Phe Ala Ser Tyr Asn Lys
                340                 345                 350

Phe Asn Asn Asn Cys Tyr Gln Asp Ala Leu Val Thr Ser Val Val Asn
                355                 360                 365

Cys Met Thr Ser Phe Val Ser Gly Phe Val Ile Phe Thr Val Leu Gly
    370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415

Met Pro Ala Ser Thr Phe Phe Ala Ile Ile Phe Phe Leu Met Leu Ile
                420                 425                 430

Thr Leu Gly Leu Asp Ser Thr Phe Ala Gly Leu Glu Gly Val Ile Thr
                435                 440                 445

Ala Val Leu Asp Glu Phe Pro His Val Trp Ala Lys Arg Arg Glu Arg
    450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
                500                 505                 510

Ser Trp Phe Tyr Gly Ile Thr Gln Phe Cys Arg Asp Val Lys Glu Met
                515                 520                 525

Leu Gly Phe Ser Pro Gly Trp Phe Trp Arg Ile Cys Trp Val Ala Ile
530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
                580                 585                 590

Ile Ala Tyr Arg Leu Ile Ile Thr Pro Gly Thr Phe Lys Glu Arg Ile
                595                 600                 605

Ile Lys Ser Ile Thr Pro Glu Thr Pro Thr Glu Ile Pro Cys Gly Asp
610                 615                 620

Ile Arg Leu Asn Ala Val
```

<210> SEQ ID NO 3
<211> LENGTH: 23
<212> TYPE: DNA
<213> ORGANISM: Homo sapiens

<400> SEQUENCE: 3
tcctccgctt tggcgcctct tcc                                    23

<210> SEQ ID NO 4
<211> LENGTH: 23
<212> TYPE: DNA
<213> ORGANISM: Homo sapiens

<400> SEQUENCE: 4
tgggggttgc agggagatc ctg                                     23

<210> SEQ ID NO 5
<211> LENGTH: 21
<212> TYPE: DNA
<213> ORGANISM: Homo sapiens

<400> SEQUENCE: 5
gcagaagcga tagccaacat g                                      21

<210> SEQ ID NO 6
<211> LENGTH: 22
<212> TYPE: DNA
<213> ORGANISM: Homo sapiens

<400> SEQUENCE: 6
caagcccagc gtgattaaca tc                                     22

<210> SEQ ID NO 7
<211> LENGTH: 18
<212> TYPE: DNA
<213> ORGANISM: Homo sapiens
<220> FEATURE:
<221> NAME/KEY: misc_feature
<222> LOCATION: 12
<223> OTHER INFORMATION: n = C or A

<400> SEQUENCE: 7
ctttctttgc cntcatct                                          18

<210> SEQ ID NO 8
<211> LENGTH: 21
<212> TYPE: DNA
<213> ORGANISM: Homo sapiens

<400> SEQUENCE: 8
cgttgccgct ctgaatgcca g                                      21

<210> SEQ ID NO 9
<211> LENGTH: 24
<212> TYPE: DNA
<213> ORGANISM: Homo sapiens

<400> SEQUENCE: 9
ggattctggt gccacctaga cgcc                                   24

<210> SEQ ID NO 10
<211> LENGTH: 52

```
<212> TYPE: DNA
<213> ORGANISM: Homo sapiens
<220> FEATURE:
<221> NAME/KEY: misc_feature
<222> LOCATION: 27
<223> OTHER INFORMATION: n = g or t

<400> SEQUENCE: 10
gccatatatt ttctgagtag catatanaat tttattgctg aatctacta ga         52

<210> SEQ ID NO 11
<211> LENGTH: 21
<212> TYPE: DNA
<213> ORGANISM: Homo sapiens

<400> SEQUENCE: 11
cgttgccgct ctgaatgcca g                                          21

<210> SEQ ID NO 12
<211> LENGTH: 24
<212> TYPE: DNA
<213> ORGANISM: Homo sapiens

<400> SEQUENCE: 12
ggattctggt gccacctaga cgcc                                       24

<210> SEQ ID NO 13
<211> LENGTH: 23
<212> TYPE: DNA
<213> ORGANISM: Homo Sapiens

<400> SEQUENCE: 13
tcctccgctt tggcgcctct tcc                                        23

<210> SEQ ID NO 14
<211> LENGTH: 23
<212> TYPE: DNA
<213> ORGANISM: Homo Sapiens

<400> SEQUENCE: 14
tgggggttgc aggggagatc ctg                                        23

<210> SEQ ID NO 15
<211> LENGTH: 23
<212> TYPE: DNA
<213> ORGANISM: Homo Sapiens

<400> SEQUENCE: 15
tcctccgctt tggcgcctct tcc                                        23

<210> SEQ ID NO 16
<211> LENGTH: 23
<212> TYPE: DNA
<213> ORGANISM: Homo Sapiens

<400> SEQUENCE: 16
tgggggttgc aggggagatc ctg                                        23

<210> SEQ ID NO 17
<211> LENGTH: 21
<212> TYPE: DNA
<213> ORGANISM: Homo Sapiens

<400> SEQUENCE: 17
```

```
gcagaagcga tagccaacat g                                        21

<210> SEQ ID NO 18
<211> LENGTH: 22
<212> TYPE: DNA
<213> ORGANISM: Homo Sapiens

<400> SEQUENCE: 18
caagcccagc gtgattaaca tc                                       22

<210> SEQ ID NO 19
<211> LENGTH: 18
<212> TYPE: DNA
<213> ORGANISM: Homo Sapiens
<220> FEATURE:
<221> NAME/KEY: misc_feature
<222> LOCATION: 12
<223> OTHER INFORMATION: n = c or a

<400> SEQUENCE: 19
ctttctttgc cntcatct                                            18
```